(12) United States Patent
Chen et al.

(10) Patent No.: US 10,077,262 B2
(45) Date of Patent: Sep. 18, 2018

(54) THIENOTHIADIAZOLE COMPOUNDS AND RELATED SEMICONDUCTOR DEVICES

(71) Applicant: Flexterra, Inc., Skokie, IL (US)

(72) Inventors: Zhihua Chen, Skokie, IL (US); Antonio Facchetti, Chicago, IL (US)

(73) Assignee: Flexterra, Inc., Skokie, IL (US)

( * ) Notice: Subject to any disclaimer, the term of this patent is extended or adjusted under 35 U.S.C. 154(b) by 0 days.

(21) Appl. No.: 15/348,971

(22) Filed: Nov. 10, 2016

(65) Prior Publication Data
US 2017/0233384 A1    Aug. 17, 2017

Related U.S. Application Data

(60) Provisional application No. 62/253,674, filed on Nov. 10, 2015.

(51) Int. Cl.
| | | |
|---|---|---|
| *C07D 417/14* | (2006.01) | |
| *H01L 51/00* | (2006.01) | |
| *H01L 51/50* | (2006.01) | |
| *H01L 51/05* | (2006.01) | |
| *H01L 51/42* | (2006.01) | |

(52) U.S. Cl.
CPC ........ *C07D 417/14* (2013.01); *H01L 51/0036* (2013.01); *H01L 51/0558* (2013.01); *H01L 51/42* (2013.01); *H01L 51/5056* (2013.01); *H01L 51/5072* (2013.01)

(58) Field of Classification Search
None
See application file for complete search history.

(56) References Cited

U.S. PATENT DOCUMENTS

| | | | |
|---|---|---|---|
| 3,457,073 A | 7/1969 | Delzenne | |
| 4,795,817 A * | 1/1989 | Chenard | A01N 43/90 548/126 |
| 5,616,590 A | 4/1997 | Maetzke | |
| 6,335,539 B1 | 1/2002 | Dimitrakopoulos et al. | |
| 6,569,707 B2 | 5/2003 | Dimitrakopoulos et al. | |
| 7,354,532 B2 | 4/2008 | Hsu et al. | |
| 8,471,249 B2 | 6/2013 | Chiu et al. | |
| 8,586,246 B2 | 11/2013 | Nakai et al. | |
| 8,586,766 B2 | 11/2013 | Kubo et al. | |
| 9,045,477 B2 | 6/2015 | Campbell | |
| 2004/0058232 A1 | 3/2004 | Kim et al. | |
| 2006/0289843 A1 | 12/2006 | Hsu et al. | |
| 2007/0170401 A1 | 7/2007 | Hsu et al. | |
| 2007/0202356 A1 | 8/2007 | Okada | |
| 2007/0298530 A1 | 12/2007 | Feehery | |
| 2008/0061685 A1 | 3/2008 | Chesterfield | |
| 2008/0191172 A1 | 8/2008 | Hsu et al. | |
| 2013/0026459 A1 | 1/2013 | Yoshimura et al. | |
| 2014/0107350 A1 | 4/2014 | Nakamura et al. | |
| 2014/0319509 A1 | 10/2014 | Hattori et al. | |
| 2017/0096523 A1 | 4/2017 | Facchetti et al. | |
| 2017/0110666 A1 | 4/2017 | Facchetti et al. | |
| 2017/0155053 A1 | 6/2017 | Facchetti et al. | |

FOREIGN PATENT DOCUMENTS

| | | | |
|---|---|---|---|
| JP | S56-30264 | 3/1981 | |
| JP | H02-30070 | 1/1990 | |
| WO | 2010077710 A2 | 7/2010 | |
| WO | 2011098113 A2 | 8/2011 | |
| WO | WO-2013102035 A1 * | 7/2013 | ........... C08G 61/123 |
| WO | 2014040572 A1 | 3/2014 | |
| WO | 2016025632 A1 | 2/2016 | |

OTHER PUBLICATIONS

Cimrova', et al., Macromol. Symp., 295:65 (Year: 2010).*
M.E. Trusova et al., A Green Procedure for the Diazotization—Iodination of Aromatic Amines under Aqueous, Strong-Acid-Free Condition, Synthesis, 2011(13), 2154-58 (2011).
U.S. Appl. No. 15/208,303, filed Jul. 12, 2016.
U.S. Appl. No. 15/348,949, filed Nov. 10, 2016.
U.S. Appl. No. 15/430,535, filed Feb. 12, 2017.
D. Boudinet et al., "Modification of gold source and drain electrodes by self-assembled monolayer in staggered n- and p-channel organic thin film transistors," Organic Electronics, 11, 227-37 (2010).
G. Maier et al., "Heterocumulenes. 6. C5OS (5-thioxo-1,2,3,4-pentatetraen-1-one) preparation and spectroscopic properties," Chemical Abstracts Service Accession No. 1991:679381 (1991).
J.-P. Hong, "Tuning of Ag work functions by self-assembled monolayers of aromatic thiols for an efficient hole injection for solution processed triisopropylsilylethynyl pentacene organic thin film transistors," App. Phys. Letts., 92, 143311 (2008).
M. Mirza-Aghayan, "An efficient and improved method for the conversion of oxiranes into thiiranes using graphite oxide," J. Sulfur Chem., 36(1), 30-35 (2014).
R. Eisavi et al., "Magnetically separable nano CuFe2O4: an efficient and reusable heterogeneous catalyst for the green synthesis of thiiranes from epoxides with thiourea," J. Sulfur Chem., 37(5), 537-545 (2016), with supplemental information.
D. J. Darensbourg et al., "Oxygen/Sulfur Scrambling During the Copolymerization of Cyclopentene Oxide and Carbon Disulfide: Selectivity for Copolymer vs Cylic [Thio]carbonates," Macromolecules, 46, 8202-10 (2013), with supplemental information.
N.V. Vereshchagina et al., "Alternative Methods for Production of Alicyclic Epoxides," Petroleum Chemistry (Russia), 54, 207-213 (2014).
R. Eisavi et al., "A green protocol for rapid and efficient of converstion of epoxides to thiiranes using alumina immobilized thiourea at solvent-free conditions," Phosphorus, Sulfur, and Silicon, 191(1), 65-69 (2016).

(Continued)

*Primary Examiner* — Michael Barker
(74) *Attorney, Agent, or Firm* — McDonnell Boehnen Hulbert & Berghoff LLP

(57) ABSTRACT

The present invention relates to new semiconducting compounds having at least one optionally substituted thienothiadiazole moiety. The compounds disclosed herein can exhibit high carrier mobility and/or efficient light absorption/emission characteristics, and can possess certain processing advantages such as solution-processability and/or good stability at ambient conditions.

20 Claims, 4 Drawing Sheets
(3 of 4 Drawing Sheet(s) Filed in Color)

(56) References Cited

OTHER PUBLICATIONS

N. Azizi et al., "Odourless Strategy for Deep Eutectic Solvent-Mediated Ring Opening of Epoxides with In Situ Generated S-Alkylisothiournonium Salts," SYNLETT, 2014(25), 2085-88 (2014).
X. Chen, "Synthesis of 3-acyl-5,6-dihydro-1,4-oxathiines through ring expansion of thiiranes," Tetrahedron Letters, 58, 1651-54 (2017).
J. C. Love et al., "Self-Assembled Monolayers of Thiolates on Metals as a Form of Nanotechnology," Chem. Rev., 105, 1103-69 (2005).

* cited by examiner

| Structures | HOMO (eV) | LUMO (eV) | HOMO | LUMO |
|---|---|---|---|---|
|  | -5.35 | -2.61 |  |  |
| 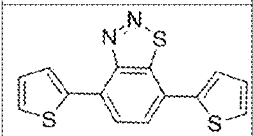 | -5.65 | -2.22 |  |  |
| 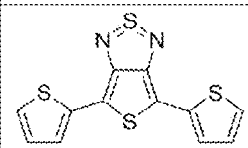 | -4.91 | -3.00 |  |  |
|  | -5.33 | -2.54 |  |  |
|  | -5.33 | -2.54 |  |  |
|  | -5.35 | -2.53 |  |  |
|  | -5.35 | -2.54 |  |  |

| Structures | HOMO (eV) | LUMO (eV) | HOMO | LUMO |
|---|---|---|---|---|
|  | -4.95 | -2.65 |  |  |
| 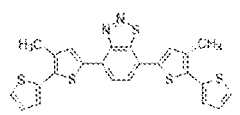 | -5.17 | -2.31 |  |  |
| 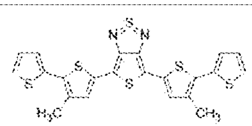 | -4.58 | -3.03 |  |  |
|  | -4.94 | -2.60 |  |  |
|  | -4.94 | -2.61 |  |  |
|  | -4.95 | -2.61 |  |  |
|  | -4.95 | -2.60 |  |  |

THIENOTHIADIAZOLE COMPOUNDS AND RELATED SEMICONDUCTOR DEVICES

CROSS-REFERENCE TO RELATED APPLICATIONS

This application claims priority to and the benefit of U.S. Provisional Patent Application Ser. No. 62/253,674 filed on Nov. 10, 2015, the disclosure of which is incorporated by reference herein in its entirety.

BACKGROUND

A new generation of optoelectronic devices such as organic thin film transistors (OTFTs), organic light emitting transistors (OLETs), organic light emitting diodes (OLEDs), printable circuits, organic photovoltaic (OPV) devices, electrochemical capacitors, and sensors are built upon organic semiconductors as their active components. To enable high device efficiencies such as large charge carrier mobilities (μ) needed for transistor and circuit operations, or efficient exciton formation and splitting necessary for OLED and OPV operations, it is desirable that both p-type (hole-transporting) and n-type (electron-transporting) organic semiconductor materials are available. Furthermore, these organic semiconductor-based devices should exhibit satisfactory stability in ambient conditions and should be processable in a cost-effective manner.

Several p- and n-channel molecular semiconductors have achieved acceptable device performance and stability. For example, OTFTs based on acenes and oligothiophenes (p-channel) and perylenes (n-channel) exhibit carrier mobilities (μ)>0.5 cm²/Vs in ambient conditions. However, molecular semiconductors typically are less easily processable via printing methodologies than polymeric semiconductors due to solution viscosity requirements.

Accordingly, the art desires new molecular and polymeric semiconductors, particularly those having good stability, processing properties, and/or charge transport characteristics in ambient conditions.

SUMMARY

In light of the foregoing, the present teachings provide organic semiconducting compounds that can address various deficiencies and shortcomings of the prior art, including those outlined above. Compounds according to the present teachings can exhibit properties such as optimized optical absorption, good charge transport characteristics and chemical stability in ambient conditions, low-temperature processability, large solubility in common solvents, and processing versatility (e.g., via various solution processes). As a result, optoelectronic devices such as OPV cells that incorporate one or more of the present compounds as a photoactive layer can exhibit high performance in ambient conditions, for example, demonstrating one or more of low band-gap, high fill factor, high open circuit voltage, and high power conversion efficiency; while field effect devices such as thin film transistors that incorporate one or more of the present compounds as the semiconductor layer can demonstrate one or more of large electron mobilities, low threshold voltages, and high current on-off ratios. Similarly, other organic semiconductor-based devices such as OLETs and OLEDs can be fabricated efficiently using the semiconducting compounds described herein.

Generally, the present teachings provide semiconducting compounds that include (a) one or more moieties represented by formula (I):

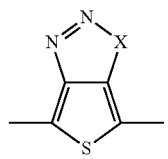

(I)

where X is a chalcogen; and (b) one or more linear conjugated moieties and/or one or more cyclic conjugated moieties other than the moieties represented by formula (I). For example, the present compounds may include a moiety of formula (I) in combination with two or more monocyclic conjugated moieties, which collectively can be represented by formula (II):

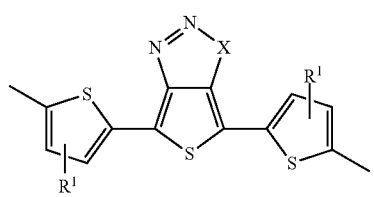

(II)

where each $R^1$ independently can be H or a substituent.

In some embodiments, the present compound can be a polymer having one or more repeating units $M_1$ each of which includes at least one moiety represented by formula (I). In certain embodiments, the repeating unit $M_1$ can further include one or more monocyclic conjugated moieties (Ar), one or more polycyclic conjugated moieties (pi-2) other than the moieties represented by formula (I), and/or one or more linear (noncyclic) conjugated moieties (Z). In particular embodiments, the repeating unit $M_1$ can include a moiety represented by formula (II).

In some embodiments, the present compound can be a molecular semiconductor including one or more moieties represented by formula (I) and one or more monocyclic conjugated moieties (Ar), one or more polycyclic conjugated moieties (pi-2) other than the moieties represented by formula (I), and/or one or more linear (noncyclic) conjugated moieties (Z). In certain embodiments, the present compound can be a molecular semiconductor including one or more moieties represented by formula (II).

The present teachings also provide methods of preparing such semiconducting compounds and related semiconductor materials, as well as various compositions, composites, and devices that incorporate the semiconducting compounds and semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purpose only. The drawings are not necessarily to scale, with emphasis generally being placed upon illustrating the principles of the present teachings. The drawings are not intended to limit the scope of the present teachings in any way.

The patent file contains at least one drawing executed in color. Copies of this patent with color drawing(s) will be provided by the Patent and Trademark Office upon request and payment of the necessary fee.

DETAILED DESCRIPTION

Figure 1:
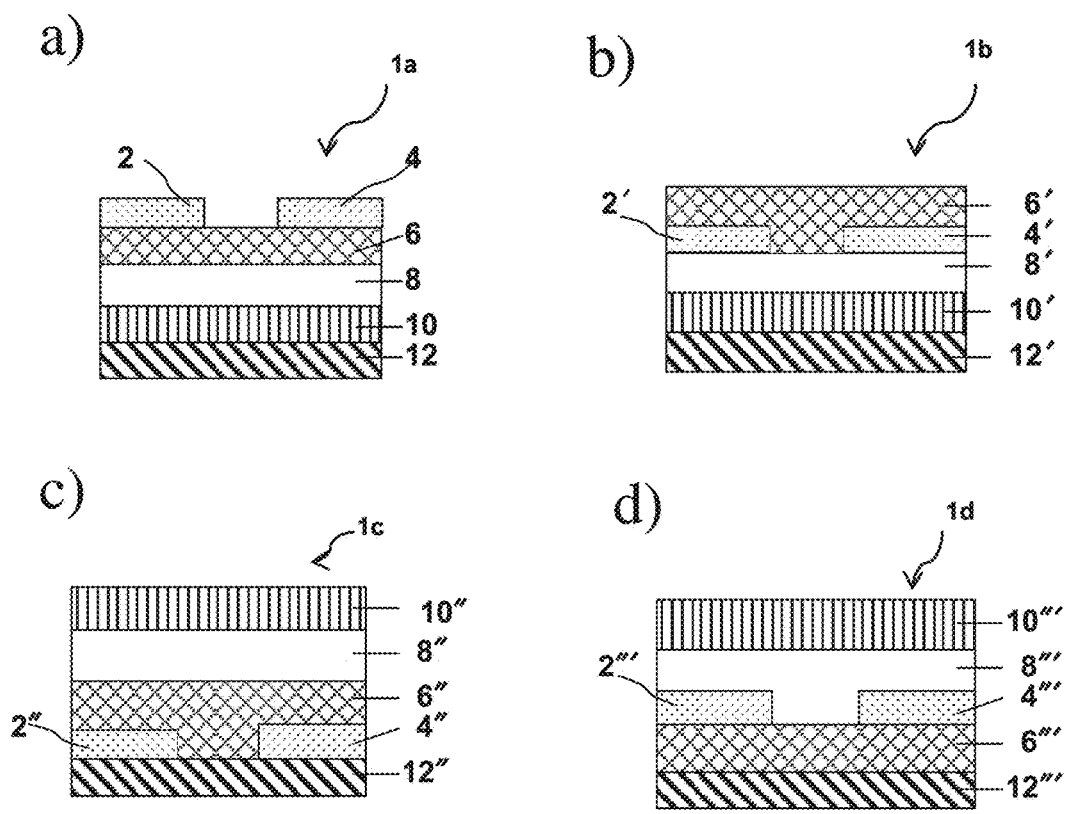
FIG. 1 illustrates four different configurations of thin film transistors: a) bottom-gate top contact, b) bottom-gate bottom-contact, c) top-gate bottom-contact, and d) top-gate top-contact; each of which can be used to incorporate one or more compounds of the present teachings, particularly as the channel (semiconductor) materials.

The present teachings provide organic semiconducting compounds and associated compositions, composites, and devices. Compounds of the present teachings can exhibit semiconductor behavior such as high carrier mobility and/or good current modulation characteristics in a field-effect device, light absorption/charge separation in a photovoltaic device, and/or charge transport/recombination/light emission in a light-emitting device. In addition, the present compounds can possess certain processing advantages such as solution-processability and/or good stability (for example, air stability) in ambient conditions. The compounds of the present teachings can be used to prepare either p-type or n-type semiconductor materials, which in turn can be used to fabricate various organic electronic articles, structures and devices, including field-effect transistors, unipolar circuitries, complementary circuitries, photovoltaic devices, and light emitting devices.

Accordingly, one aspect of the present teachings provides compounds having semiconducting activity and semiconductor materials prepared from these compounds. More specifically, the present compounds can include a moiety A represented by formula (I) and one or more moieties B which either by themselves or together with moiety A provide a pi-conjugated system. The moieties B can include one or more aromatic or otherwise highly conjugated cyclic (carbocyclic or heterocyclic) moieties, where such cyclic moieties can be optionally substituted or functionalized with one or more electron-withdrawing or electron-donating groups. The pairing of moieties A and B, and any additional functionalization on moieties B can be affected by one or more of the following considerations: 1) the electron-withdrawing capability for semiconductor processing in air and stable charge transport operation; 2) modulation of the majority carrier type depending on the electronic structure of moieties B; 3) for embodiments where the compound is a polymer, the regiochemistry of the polymerization possibly affording regioregular polymers; 4) the core planarity and linearity of the compound; 5) the capability of additional functionalization of the π-conjugated moieties in one or more moieties B; 6) the potential for increased solubility of the compound for solution processing; 7) achieving strong π-π interactions/intermolecular electronic coupling; and 8) bandgap modulation via electron donor-acceptor coupling of electron-poor (acceptor) and electron-rich (donor) A-B or B-A moieties. The resulting compounds and related methods can be employed to enhance the performance of an associated device (e.g., an organic field effect transistor, a light-emitting transistor, a solar cell, or the like).

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ cm$^2$Ns. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ cm$^2$Ns. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period. In addition, a compound can be considered ambient stable if the optical absorption of the corresponding film does not vary more than 20% (preferably, does not vary more than 10%) from its initial value after exposure to ambient conditions, including air, humidity and temperature, over a 3 day, 5 day, or 10 day period.

As used herein, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp}*J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from incident light to electrical power. The PCE of a solar cell can be calculated by dividing the maximum power point ($P_m$) by the input light irradiance (E, in $W/m^2$) under standard test conditions (STC) and the surface area of the solar cell ($A_c$ in $m^2$). STC typically refers to a temperature of 25° C. and an irradiance of 1000 $W/m^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "polymeric compound" (or "polymer") refers to a molecule including a plurality of one or more repeating units connected by covalent chemical bonds. A polymeric compound can be represented by the general formula:

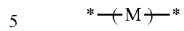

wherein M is the repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units

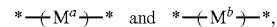

where $M^a$ and $M^b$ represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

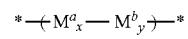

can be used to represent a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_n$) and/or weight average molecular weight ($M_w$) depending on the measuring technique(s)).

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula —$C_zH_{2z+1-t}X^0{}_t$, where $X^0$, at each occurrence, is F, Cl, Br or I, z is an integer in the range of 1 to 40, and t is an integer in the range of 1 to 81, provided that t is less than or equal to 2z+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, "heteroatom" refers to an atom of any element other than carbon or hydrogen and includes, for example, nitrogen, oxygen, silicon, sulfur, phosphorus, and selenium.

As used herein, a "cyclic moiety" can include one or more (e.g., 1-6) carbocyclic or heterocyclic rings. In embodiments where the cyclic moiety is a "polycyclic moiety," the "polycyclic moiety" can include two or more rings fused to each other (i.e., sharing a common bond) and/or connected to each other via a Spiro atom. The cyclic moiety can be a cycloalkyl group, a heterocycloalkyl group, an aryl group, or a heteroaryl group (i.e., can include only saturated bonds, or can include one or more unsaturated bonds regardless of aromaticity), and can be optionally substituted as described herein. In embodiments where the cyclic moiety is a "monocyclic moiety," the "monocyclic moiety" can include a 3-20 membered carbocyclic or heterocyclic ring. A monocyclic moiety can include a $C_{0-20}$ aryl group (e.g., $C_{6-14}$ aryl group) or a 5-20 membered heteroaryl group (e.g., 5-14 membered heteroaryl group), each of which can be optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 20 carbon atoms, for example, 3 to 14 carbon atoms (i.e., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "cycloheteroalkyl" refers to a non-aromatic cycloalkyl group that contains at least one ring heteroatom selected from O, S, Se, N, P, and Si (e.g., O, S, and N), and optionally contains one or more double or triple bonds. A cycloheteroalkyl group can have 3 to 20 ring atoms, for example, 3 to 14 ring atoms (i.e., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 22 carbon atoms in its ring system (e.g., $C_{6-14}$ aryl group), which can include multiple fused rings. In some embodiments, a polycyclic aryl group can have from 8 to 22 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic) and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an -alkyl-aryl group, where the arylalkyl group is covalently linked to the defined chemical structure via the alkyl group. An arylalkyl group is within the definition of a —Y—$C_{6-14}$ aryl group, where Y is as defined herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, 5 to 22 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

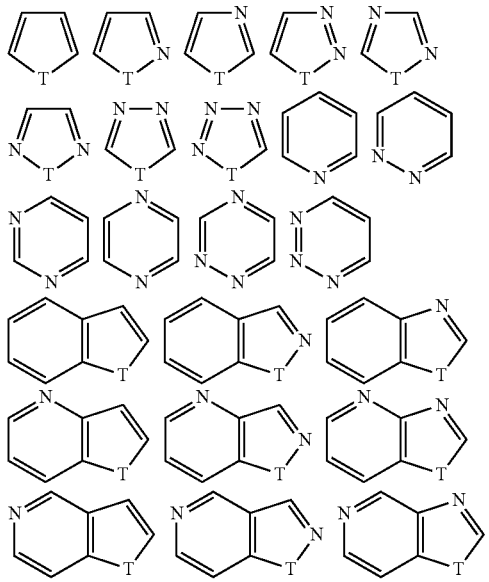
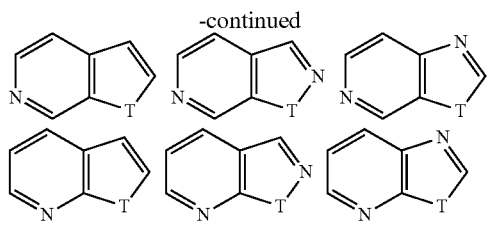

where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group).

The electron-donating or electron-withdrawing properties of several hundred of the most common substituents, reflecting all common classes of substituents have been determined, quantified, and published. The most common quantification of electron-donating and electron-withdrawing properties is in terms of Hammett a values. Hydrogen has a Hammett a value of zero, while other substituents have Hammett a values that increase positively or negatively in direct relation to their electron-withdrawing or electron-donating characteristics. Substituents with negative Hammett a values are considered electron-donating, while those with positive Hammett a values are considered electron-withdrawing. See Lange's Handbook of Chemistry, 12th ed., McGraw Hill, 1979, Table 3-12, pp. 3-134 to 3-138, which lists Hammett a values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), —NO$_2$, —CN, —NC, —S(R$^0$)$_2$$^+$), —N(R$^0$)$_3$$^+$, —SO$_3$H, —SO$_2$R$^0$, —SO$_3$R$^0$, —SO$_2$NHR$^0$, —SO$_2$N(R$^0$)$_2$, —COOH, —COR$^0$, —COOR$^0$, —CONHR$^0$, —CON(R$^0$)$_2$, C$_{1-40}$ haloalkyl groups, C$_{6-14}$ aryl groups, and 5-14 membered electron-poor heteroaryl groups; where R$^0$ is a C$_{1-20}$ alkyl group, a C$_{2-20}$ alkenyl group, a C$_{2-20}$ alkynyl group, a C$_{1-20}$ haloalkyl group, a C$_{1-20}$ alkoxy group, a C$_{0-14}$ aryl group, a C$_{3-14}$ cycloalkyl group, a 3-14 membered cycloheteroalkyl group, and a 5-14 membered heteroaryl group, each of which can be optionally substituted as described herein. For example, each of the C$_{1-20}$ alkyl group, the C$_{2-20}$ alkenyl group, the C$_{2-20}$ alkynyl group, the C$_{1-20}$ haloalkyl group, the C$_{1-20}$ alkoxy group, the C$_{6-14}$ aryl group, the C$_{3-14}$ cycloalkyl group, the 3-14 membered cycloheteroalkyl group, and the 5-14 membered heteroaryl group can be optionally substituted with 1-5 small electron-withdrawing groups such as F, Cl, Br, —NO$_2$, —CN, —NC, —S(R$^0$)$_2$$^+$, —N(R$^0$)$_3$$^+$, —SO$_3$H, —SO$_2$R$^0$, —SO$_3$R$^0$, —SO$_2$NHR$^0$, —SO$_2$N(R$^0$)$_2$, —COOH, —COR$^0$, —COOR$^0$, —CONHR$^0$, and —CON(R$^0$)$_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include —OH, —OR$^0$, —NH$_2$, —NHR$^0$, —N(R$^0$)$_2$, and 5-14 membered electron-rich heteroaryl groups, where R$^0$ is a C$_{1-20}$ alkyl group, a C$_{2-20}$ alkenyl group, a C$_{2-20}$ alkynyl group, a C$_{6-14}$ aryl group, or a C$_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual subcombination of the members of such groups and ranges. For example, the term "C$_{1-6}$ alkyl" is specifically intended to individually disclose C$_1$, C$_2$, C$_3$, C$_4$, C$_5$, C$_6$, C$_1$-C$_6$, C$_1$-C$_5$, C$_1$-C$_4$, C$_1$-C$_3$, C$_1$-C$_2$, C$_2$-C$_6$, C$_2$-C$_5$, C$_2$-C$_4$, C$_2$-C$_3$, C$_3$-C$_6$, C$_3$-C$_5$, C$_3$-C$_4$, C$_4$-C$_6$, C$_4$-C$_5$, and C$_5$-C$_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide (N$_3$), thiocyanate (SCN), nitro (NO$_2$), cyanate (CN), water (H$_2$O), ammonia (NH$_3$), and sulfonate groups (e.g., OSO$_2$—R, wherein R can be a C$_{1-10}$ alkyl group or a C$_{6-14}$ aryl group each optionally substituted with 1-4 groups independently selected from a C$_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTO.

In various embodiments, semiconducting compounds according to the present teachings generally include (a) one or more moieties represented by formula (I):

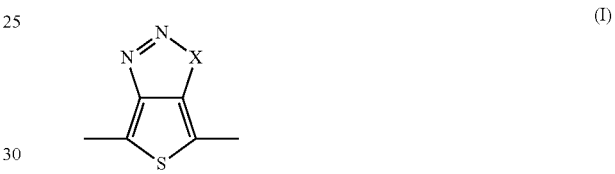

where X is a chalcogen; and
(b) one or more linear conjugated moieties and/or one or more cyclic conjugated moieties other than the moieties represented by formula (I).

For example, in addition to the moieties represented by formula (I), the present semiconducting compounds can include one or more monocyclic conjugated moieties (Ar), one or more polycyclic conjugated moieties (pi-2) that are different from the moieties represented by formula (I), and/or one or more linear (noncyclic) conjugated moieties (Z).

To illustrate, in certain embodiments, the present semiconducting compounds can include at least one moiety represented by formula (I) and at least one monocyclic conjugated moiety. For example, the monocyclic conjugated moieties can be an optionally substituted 5- or 6-membered aryl or heteroaryl group. Accordingly, compounds according to such embodiments can include one or more moieties represented by formula (II):

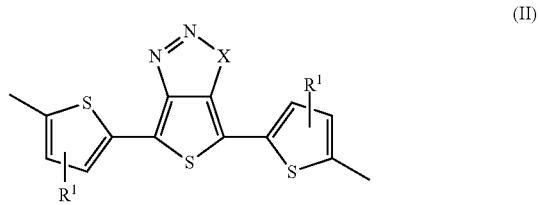

where R$^1$, at each occurrence, independently can be selected from the group consisting of H, halogen, —CN, NO$_2$, R$^2$, -L-R$^3$, OH, OR$^2$, OR$^3$, NH$_2$, NHR$^2$, N(R$^2$)$_2$, NHR$^3$, NR$^2$R$^3$, N(R$^3$)$_2$, SH, SR$^2$, SR$^3$, S(O)$_2$OH, —S(O)$_2$OR$^2$, —S(O)$_2$OR$^3$, C(O)H, C(O)R$^2$, C(O)R$^3$, C(O)OH, C(O)OR$^2$, C(O)

$OR^3$, $C(O)NH_2$, $C(O)NHR^2$, $C(O)N(R^2)_2$, $C(O)NHR^3$, $C(O)NR^2R^3$, $C(O)N(R^3)_2$, $SiH_3$, $SiH(R^2)_2$, $SiH_2(R^2)$, and $Si(R^2)_3$, wherein L is selected from the group consisting of a divalent $C_{1-40}$ alkyl group, a divalent $C_{2-40}$ alkenyl group, a divalent $C_{1-40}$ haloalkyl group, and a covalent bond; $R^2$ is selected from the group consisting of a $C_{1-40}$ alkyl group, a $C_{2-40}$ alkenyl group, a $C_{2-40}$ group, and a $C_{1-40}$ haloalkyl group; and $R^3$ is selected from the group consisting of a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents selected from the group consisting of a halogen, —CN, $NO_2$, $R^2$, $OR^2$, and $SR^2$.

For example, in various embodiments, $R^1$, at each occurrence, independently can be selected from the group consisting of H, halogen, —CN, —$NO_2$, $R^2$, $OR^2$, and $SR^2$, wherein $R^2$, at each occurrence, independently can be selected from the group consisting of a $C_{1-40}$ alkyl group, a $C_{1-40}$ alkenyl group, and a $C_{1-40}$ haloalkyl group. In certain embodiments, $R^1$, at each occurrence, independently can be selected from H, F, Cl, CN, a $C_{3-40}$ alkyl group, a $C_{3-40}$ alkoxy group, a $C_{3-40}$ haloalkyl group, and a $C_{3-40}$ alkenyl group, where each of the $C_{3-40}$ alkyl group, the $C_{3-40}$ alkoxy group, the $C_{3-40}$ haloalkyl group, and the $C_{3-40}$ alkenyl group can be linear or branched. In particular embodiments, both $R^1$ can be H. In other embodiments, each $R^1$ independently can be selected from the group consisting of H, F, Cl, —CN, a $C_{3-20}$ alkyl group, a $C_{3-20}$ alkoxy group, and a $C_{3-20}$ haloalkyl group.

In various embodiments, X is a chalcogen and preferably is selected from the group consisting of O, S, or Se. In preferred embodiments, X is S. Accordingly, various compounds according to the present teachings can include one or more moieties represented by formula (III):

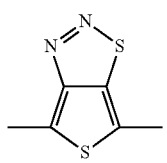
(III)

and one or more linear conjugated moieties and/or one or more cyclic conjugated moieties other than the moieties represented by formula (III). For example, certain compounds according to the present teachings can include at least one moiety represented by formula (III) and at least one cyclic conjugated moiety (such as, an optionally substituted 5- or 6-membered aryl or heteroaryl group). Accordingly, particular compounds according to the present teachings can include one or more moieties represented by formula (IV):

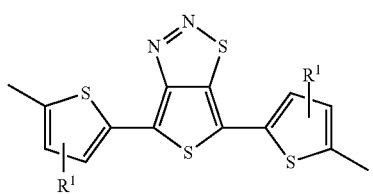
(IV)

where $R^1$ is as defined herein.

In one aspect, the present teachings provide polymers having one or more repeating units, where such repeating units can include, in the same or different repeating units, one or more moieties represented by formula (I) and one or more linear conjugated moieties and/or one or more cyclic conjugated moieties that are not moieties represented by formula (I).

Accordingly, in some embodiments, polymers according to the present teachings can include a first repeating unit $M_1$ selected from the group consisting of:

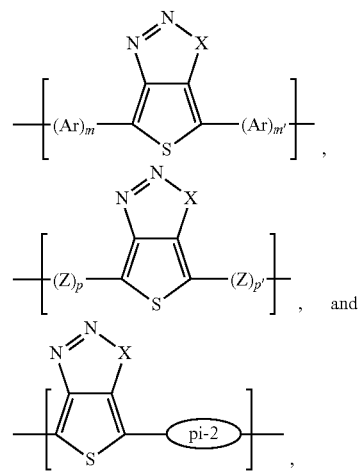

wherein:
pi-2 is an optionally substituted conjugated polycyclic moiety;
Ar, at each occurrence, independently is an optionally substituted 5- or 6-membered aryl or heteroaryl group;
Z is a conjugated noncyclic linker;
m and m' independently are 0, 1, 2, 3, 4, 5 or 6, provided that at least one of m and m' is not 0;
p and p' independently are 0 and 1, provided that at least one of p and p' is 1; and
the polymer has a degree of polymerization (n) ranging from 3 to 1,000.

In particular, the above embodiments can include a moiety of formula (I) where X is S. Polymers according to such embodiments can include a first repeating unit $M_1$ selected from the group consisting of:

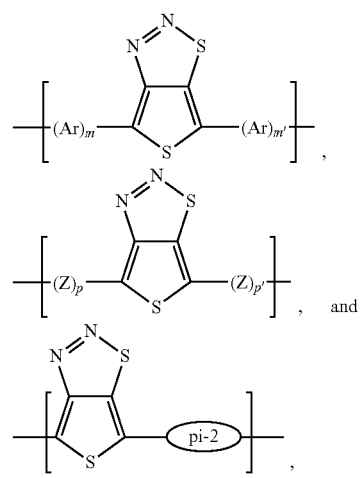

where Ar, Z, pi-2, m, m', p, and p' are as defined herein.

In some embodiments, polymers according to the present teachings can include a first repeating unit $M_1$ that includes the moiety of formula (II) and optionally additional linear and/or cyclic conjugated linkers. For example, polymers according to such embodiments can have a first repeating unit $M_1$ selected from the group consisting of:

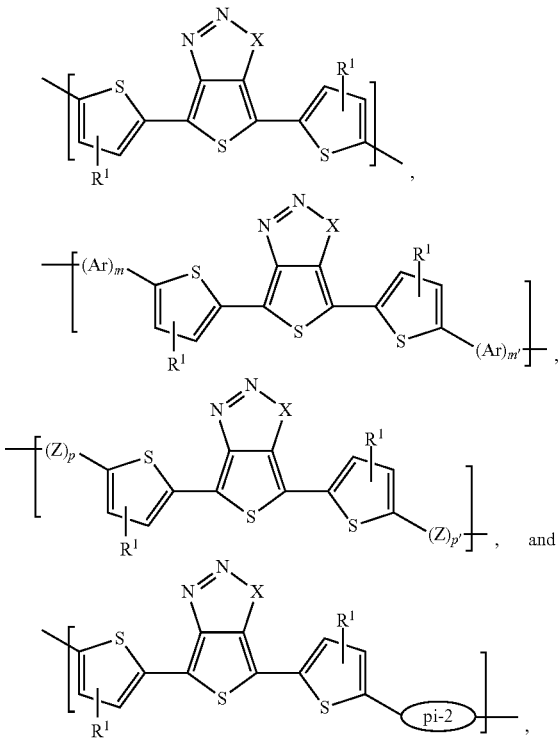

where Ar, $R^1$, X, Z, pi-2, m, m', p, and p' are as defined herein. For example, $R^1$, at each occurrence, independently can be selected from the group consisting of H, F, Cl, —CN, —NO$_2$, $R^2$, $OR^2$, and $SR^2$, where $R^2$ is selected from the group consisting of a linear or branched $C_{1-40}$ alkyl group, a linear or branched $C_{2-40}$ alkenyl group, and a linear or branched $C_{1-40}$ haloalkyl group.

In particular, the above embodiments can include the moiety of formula (II) where X is S. Polymers according to such embodiments can include a first repeating unit $M_1$ selected from the group consisting of:

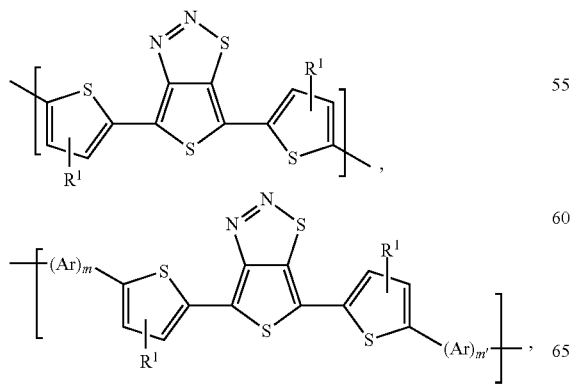

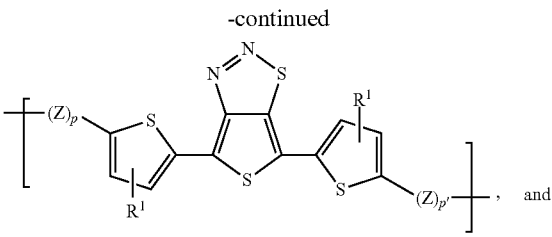

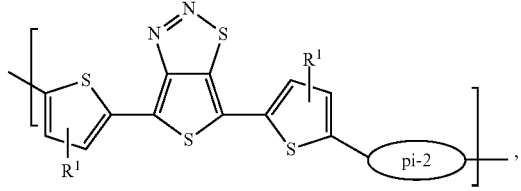

where Ar, $R^1$, Z, pi-2, m, m', p, and p' are as defined herein. For example, $R^1$, at each occurrence, independently can be selected from the group consisting of H, F, Cl, —CN, —NO$_2$, $R^2$, $OR^2$, and $SR^2$, where $R^2$ is selected from the group consisting of a linear or branched $C_{1-40}$ alkyl group, a linear or branched $C_{2-40}$ alkenyl group, and a linear or branched $C_{1-40}$ haloalkyl group.

In various embodiments, the polycyclic conjugated moiety, pi-2, can be an optionally substituted $C_{8-26}$ aryl group or 8-26 membered heteroaryl group. For example, pi-2 can have a planar and pi-extended conjugated cyclic core which can be optionally substituted as disclosed herein. Examples of suitable cyclic cores include naphthalene, anthracene, tetracene, pentacene, perylene, pyrene, coronene, fluorene, indacene, indenofluorene, and tetraphenylene, as well as their analogs in which one or more carbon atoms can be replaced with a heteroatom such as O, S, Si, Se, N, or P.

In certain embodiments, pi-2 can be selected from the group consisting of:

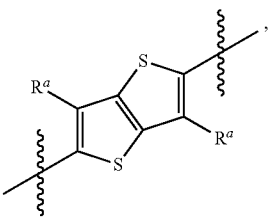

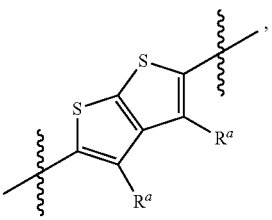

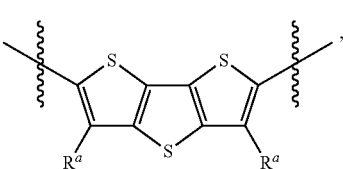

-continued
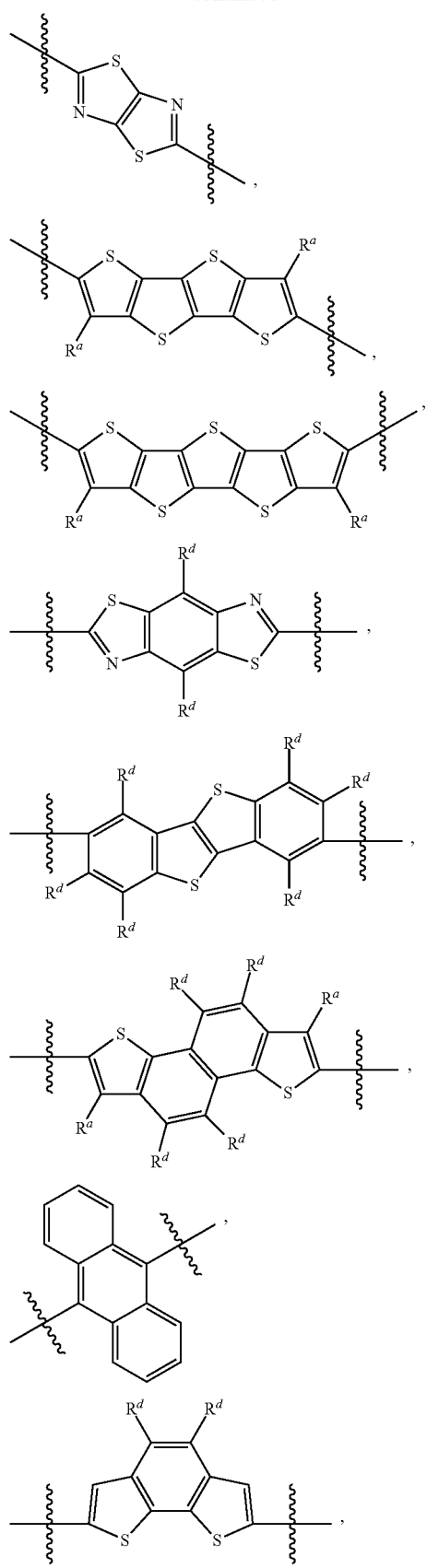
-continued
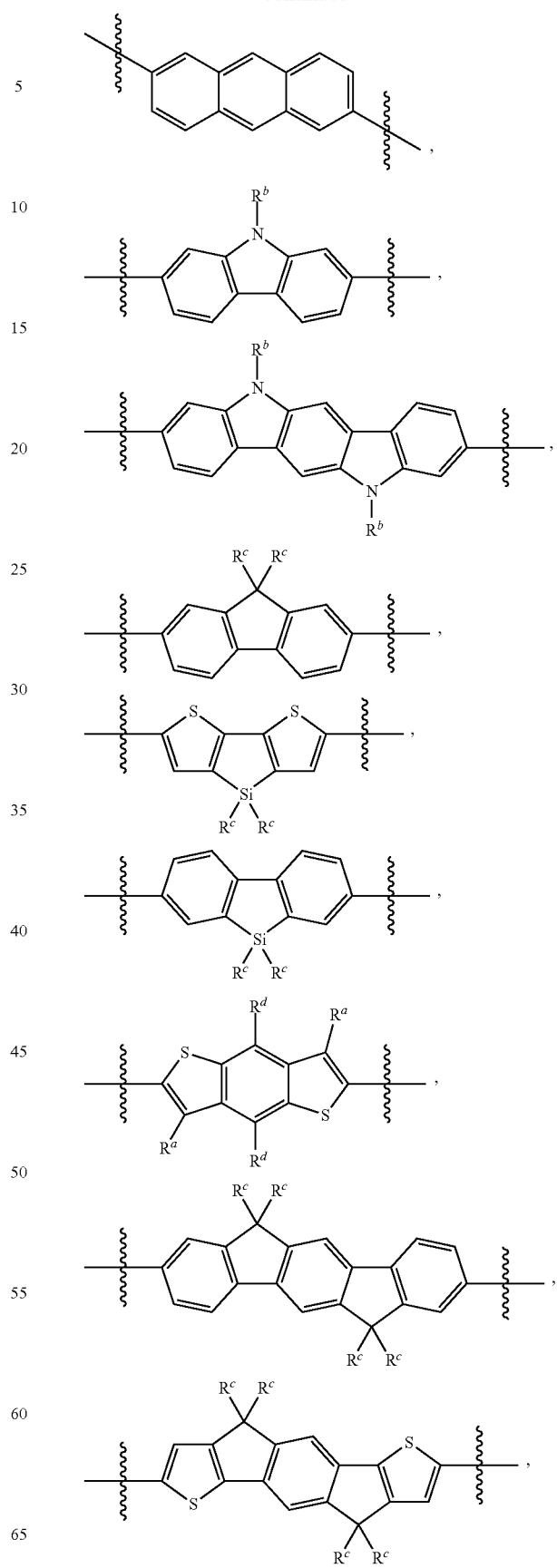

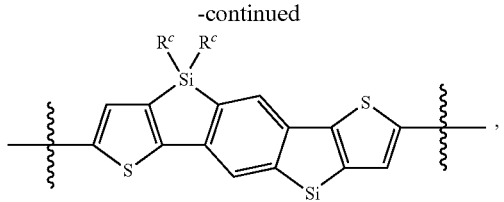
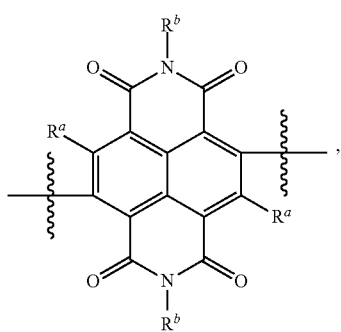
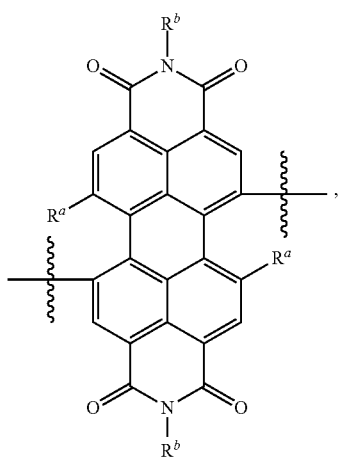
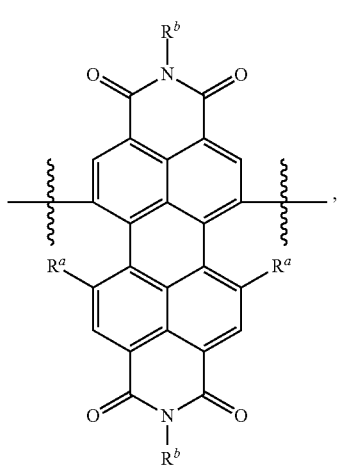
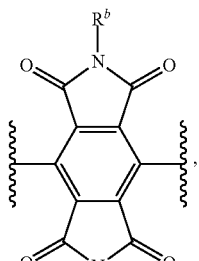
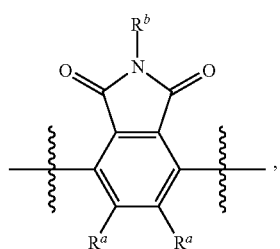
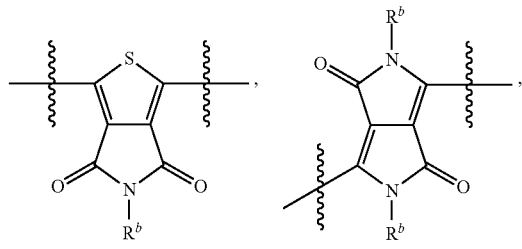
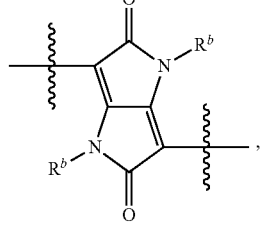
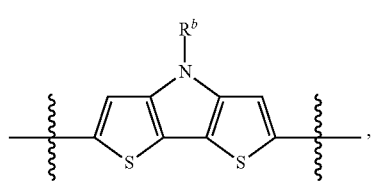
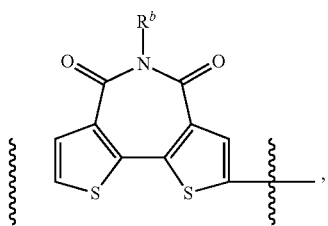
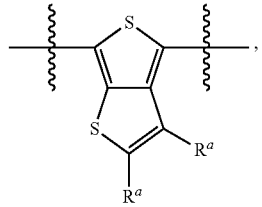

21
-continued
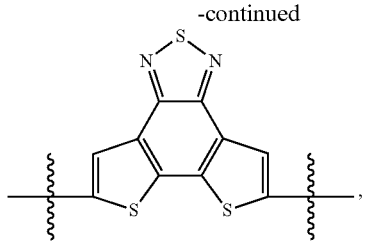,
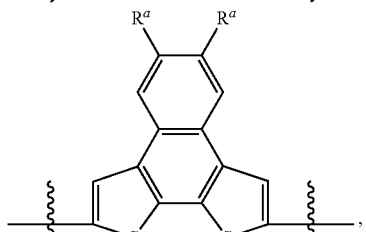,
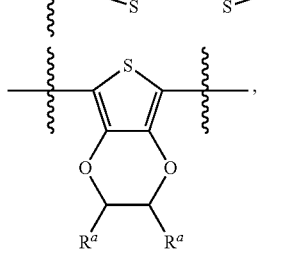,
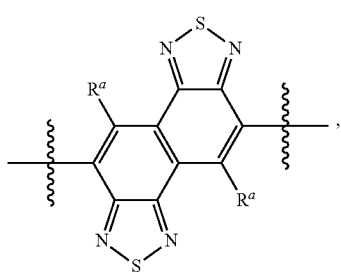,
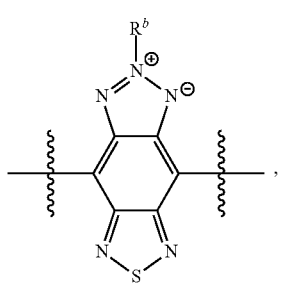,
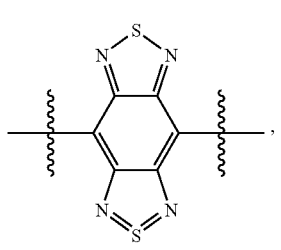,
22
-continued
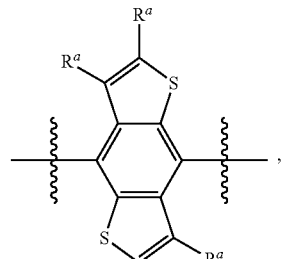,
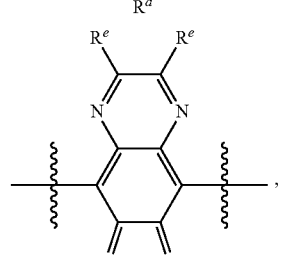,
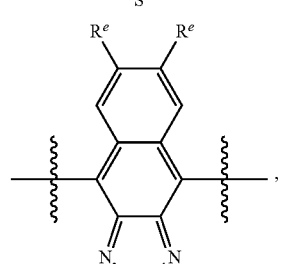,
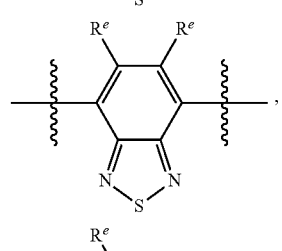,
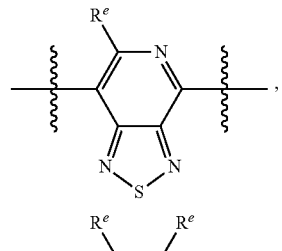,
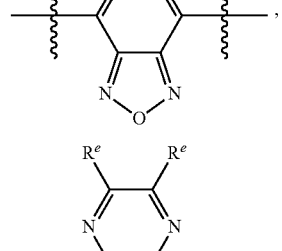,
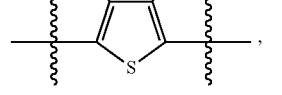, and

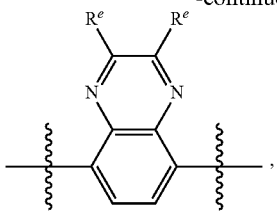

wherein:

$R^a$ is selected from the group consisting of H, F, Cl, —CN, R, —OR, —SR, —C(O)R, —OC(O)R, and —C(O)OR;
$R^b$ is selected from the group consisting of H, R, and -L'-$R^f$;
$R^c$ is H or R;
$R^d$ is selected from the group consisting of H, F, Cl, —CN, R, —OR, —SR, —C(O)R, —OC(O)R, —C(O)OR, and -L'-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L' is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

In various embodiments, the monocyclic conjugated moiety, Ar, at each occurrence, independently can be an optionally substituted 5- or 6-membered (hetero)aryl group. For example, Ar can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which optionally can be substituted with 1-4 $R^5$ groups independently selected from a halogen, CN, a $C_{1-40}$ alkyl group, a $C_{1-40}$ haloalkyl group, a $C_{1-40}$ alkoxy group, and a $C_{1-40}$ alkylthio group.

By way of example, each Ar in $(Ar)_m$ or $(Ar)_{m'}$ that is present (i.e., when m and/or m' is 1, 2, 3, 4, 5 or 6) can be represented by:

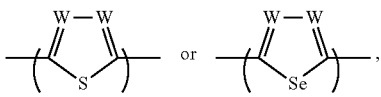

where each W independently can be selected from N, CH, and $CR^4$, wherein $R^4$ can be selected from F, Cl, —CN, $R^2$, $OR^2$, $SR^2$, $C(O)R^2$, $OC(O)R^2$, and $C(O)OR^2$, where $R^2$ is as defined herein. To illustrate further, $(Ar)_m$ and $(Ar)_{m'}$ when present can be independently selected from the group consisting of:

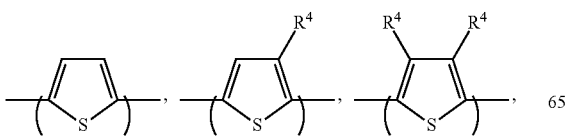

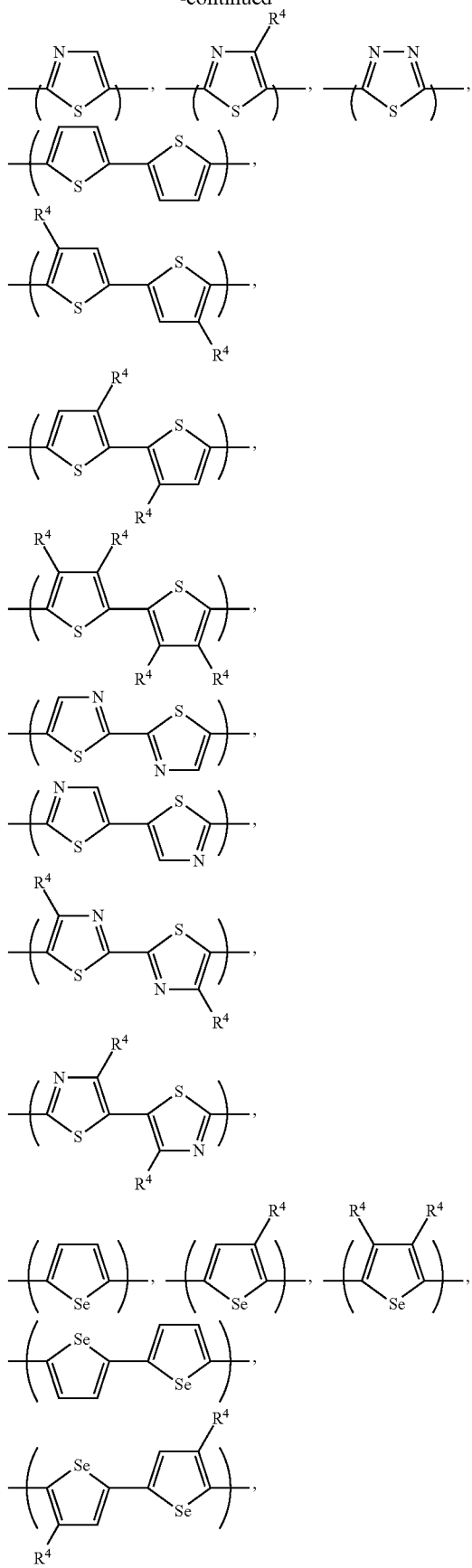

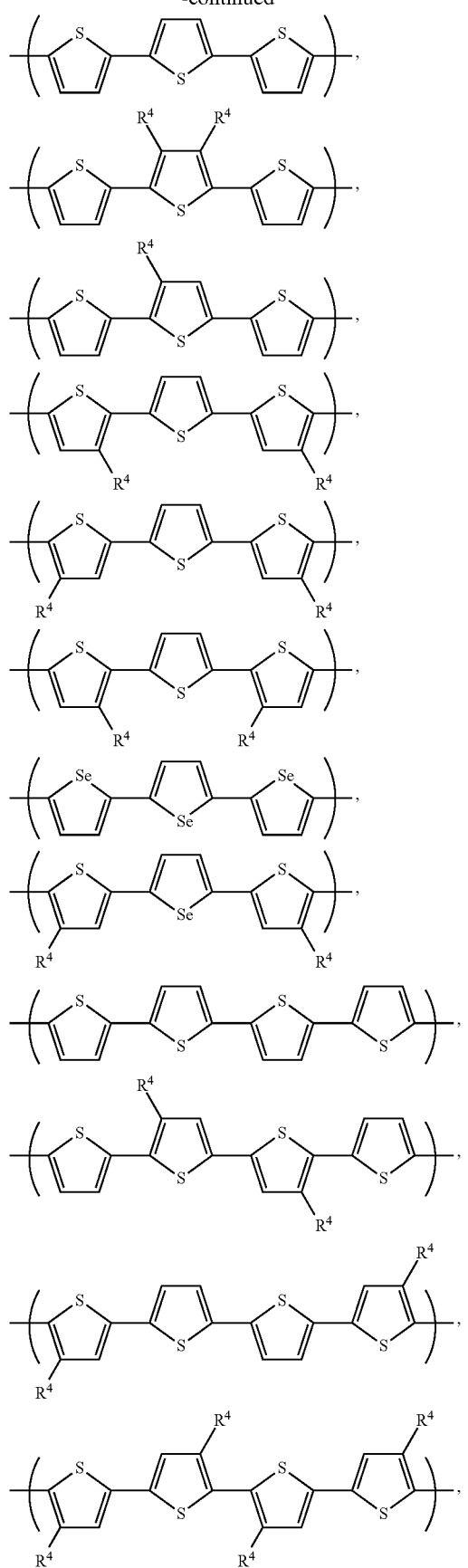
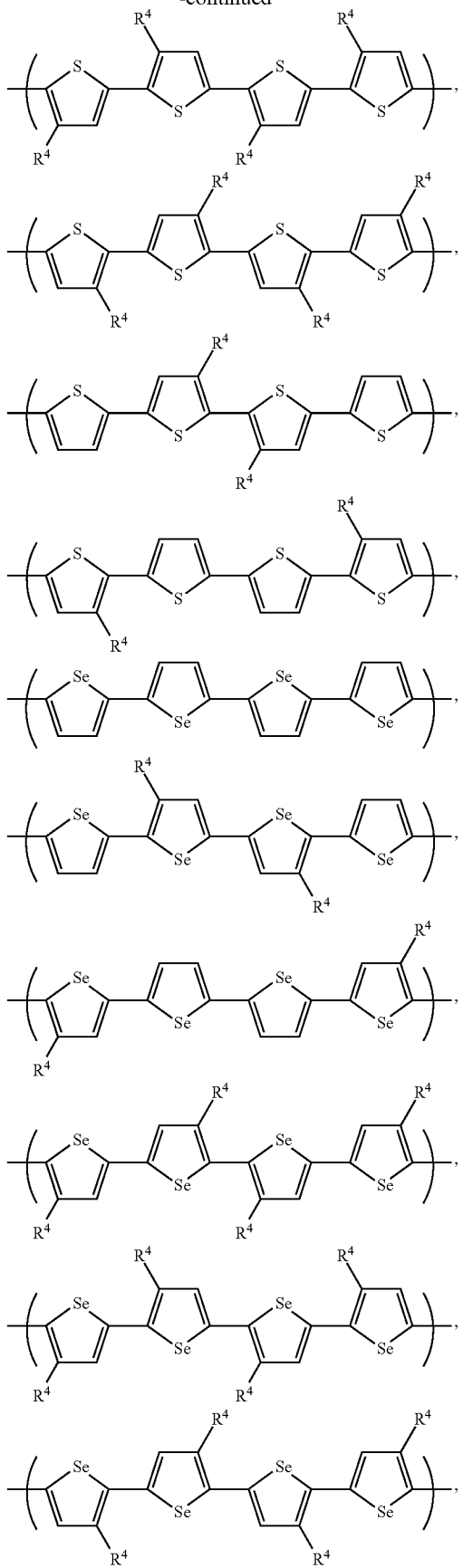

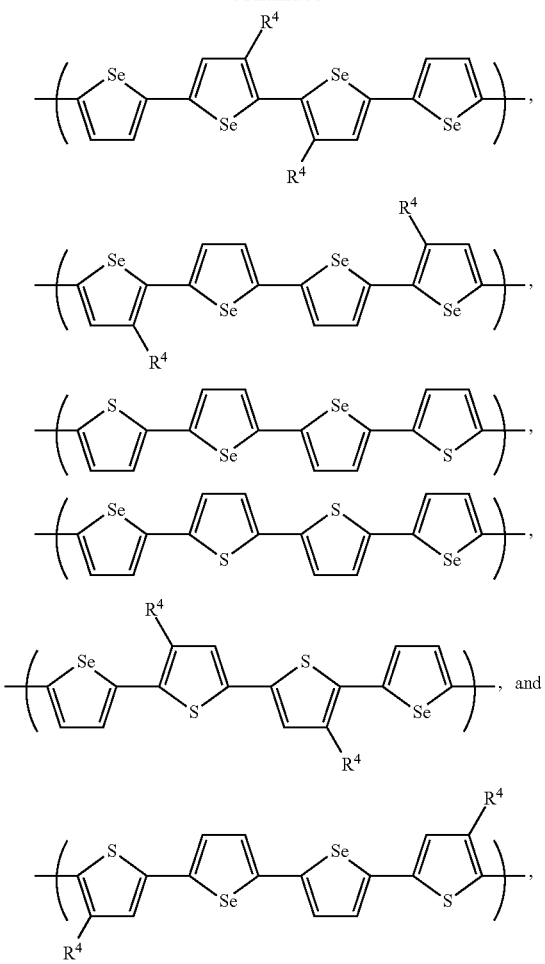

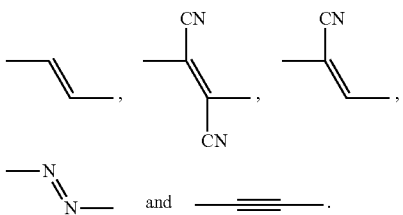

In certain embodiments, the present polymer can be a homopolymer including only identical repeating units $M_1$. In other embodiments, the polymer can be a copolymer including two or more different repeating units $M_1$. In yet other embodiments, the polymer can be a copolymer including at least one repeating unit $M_1$ and at least one other repeating unit $M_2$ that does not include any moiety of formula (I) or (II). Such $M_2$ units can include one or more noncyclic (Z), monocyclic (Ar), and/or polycyclic (pi-2) conjugated linkers, which together provide a pi-extended conjugated group. For example, $M_2$ can be selected from:

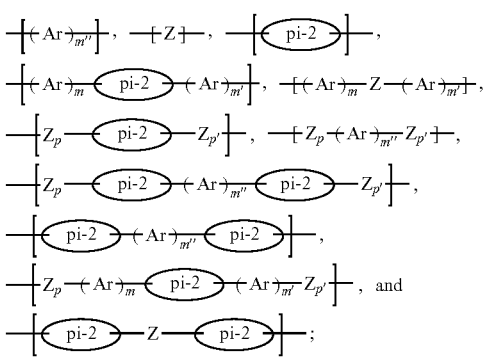

wherein m″ is 1, 2, 3, 4, 5 or 6; and pi-2, Ar, Z, m, m′, m″, p, and p′ are as defined herein.

To illustrate, in certain embodiments, $M_1$ can be selected from the group consisting of:

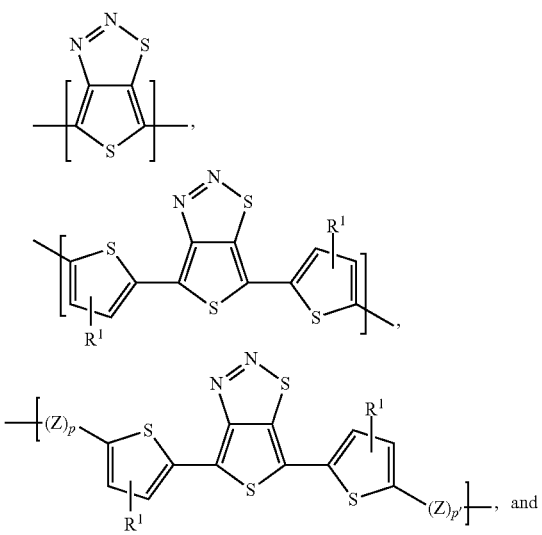

where, for example, each $R^4$ independently is selected from F, Cl, CN, $R^2$, $OR^2$, and $SR^2$, where $R^2$ is a linear or branched $C_{1-40}$ alkyl or haloalkyl group.

In various embodiments, the conjugated noncyclic linker, Z, can include one or more double or triple bonds. For example, Z can be a divalent ethenyl group (i.e., having one double bond), a divalent ethynyl group (i.e., having one tripe bond), a $C_{4-40}$ alkenyl or alkynyl group that includes two or more conjugated double or triple bonds, or some other linear or branched conjugated systems that can include heteroatoms such as Si, N, P, and the like. In certain embodiments, Z can be selected from the group consisting of:

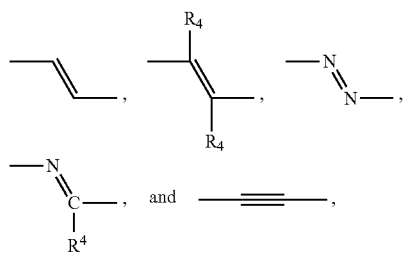

wherein $R^4$ is as defined herein. In particular embodiments, Z can be selected from the group consisting of:

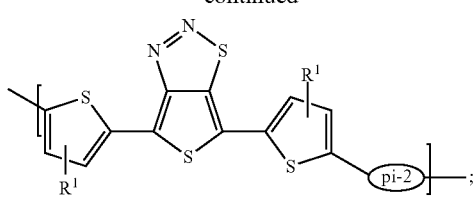
and
M₂ can have the formula:
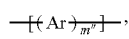
wherein m″ is 1, 2, 3, or 4; and Ar is as defined herein. For example, M₂ can be selected from the group consisting of:
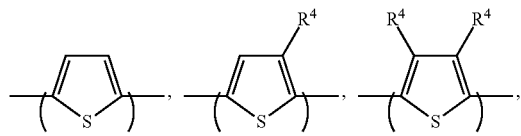
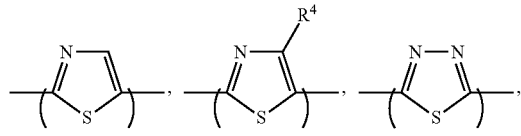
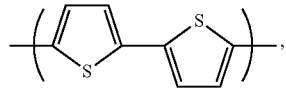
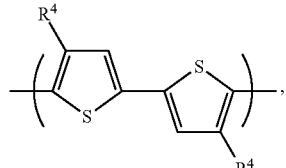
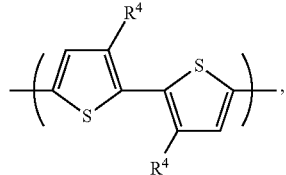
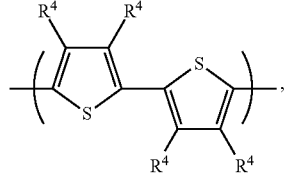
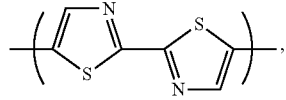
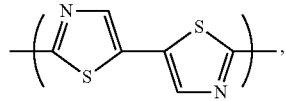
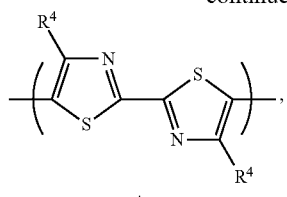
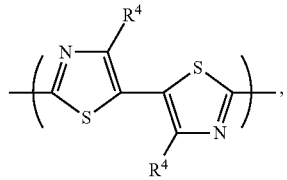
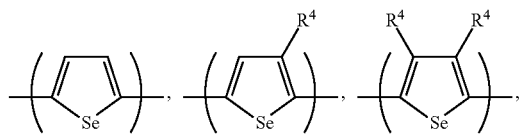
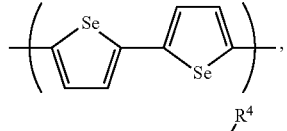
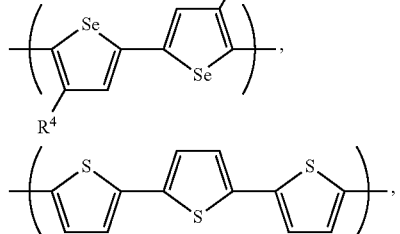
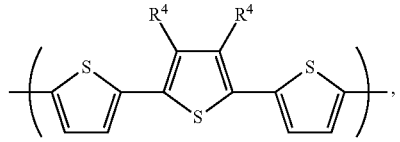
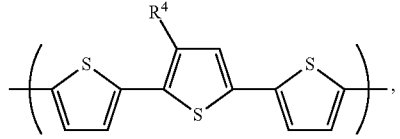
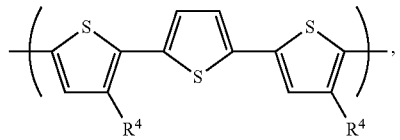
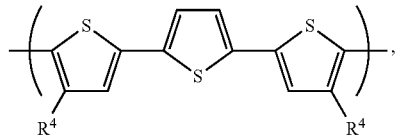
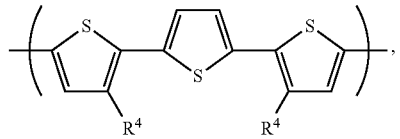
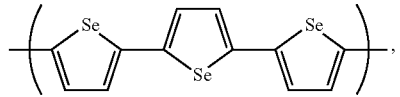

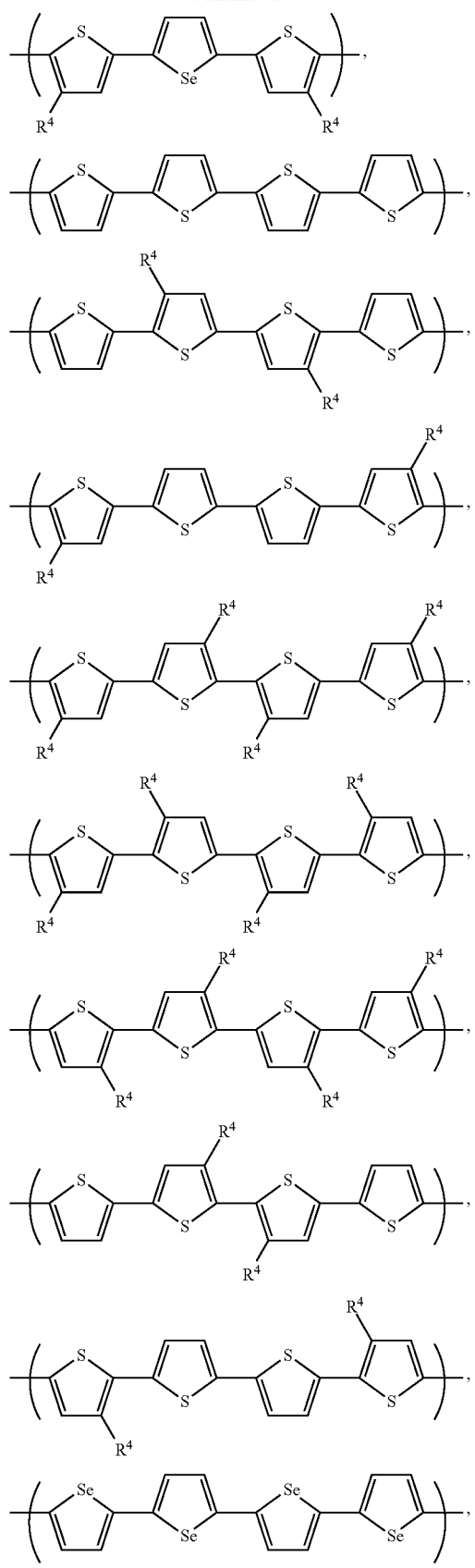
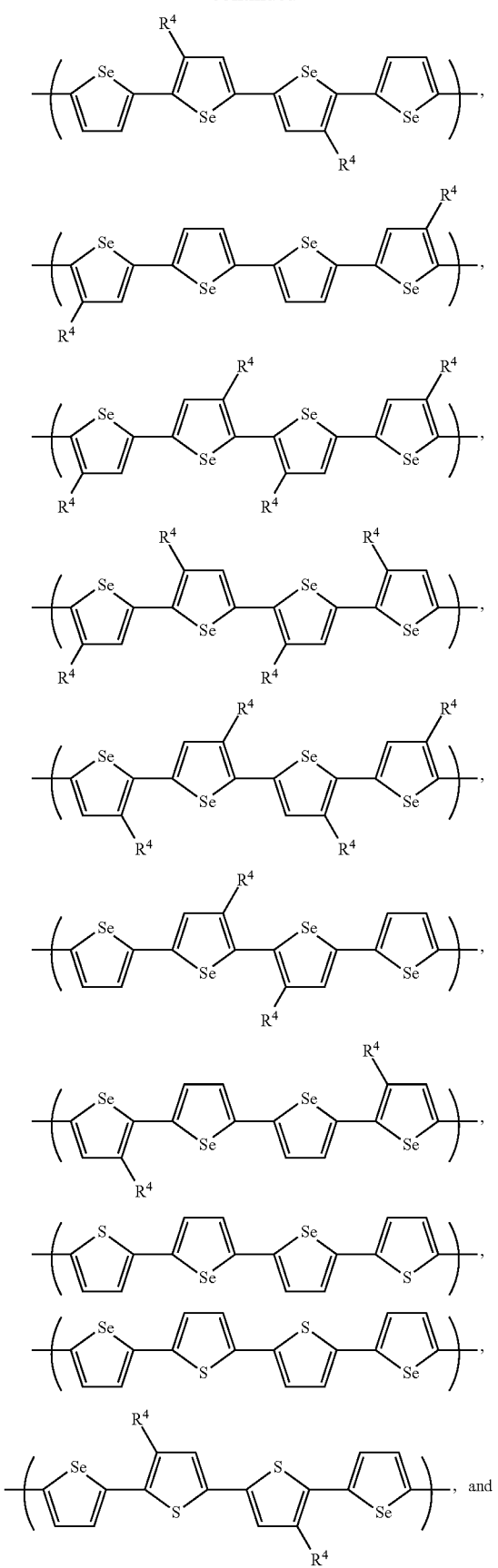

-continued
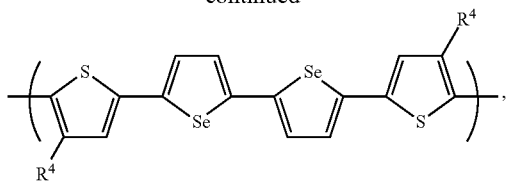
where, for example, each $R^4$ independently is selected from the group consisting of F, Cl, CN, $R^2$, $OR^2$, and $SR^2$, where $R^2$ is a linear or branched $C_{1-40}$ alkyl or haloalkyl group.
In other embodiments, $M_1$ can be selected from the group consisting of:
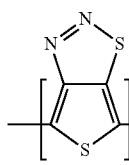
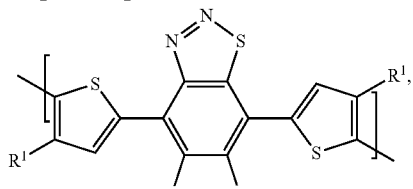
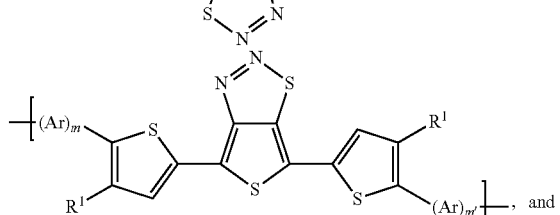
, and
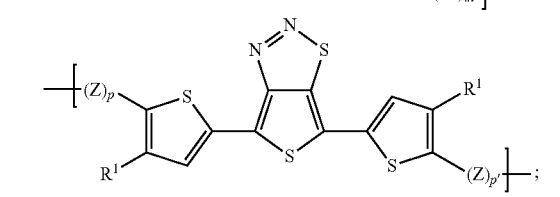
;
and
$M_2$ can have the formula:
wherein pi-2 can be selected from the group consisting of:
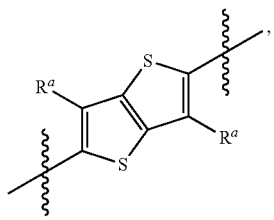
-continued
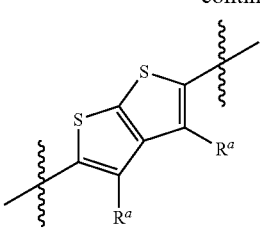
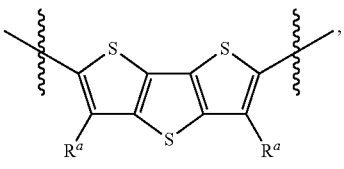
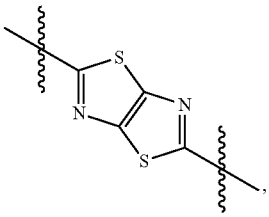
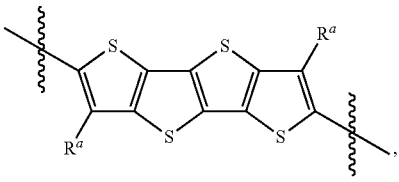
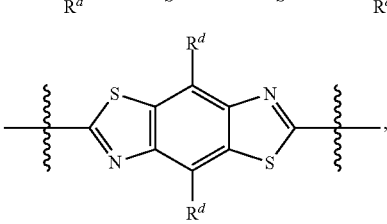
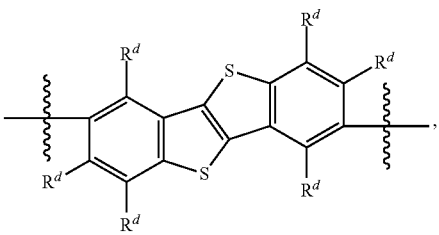
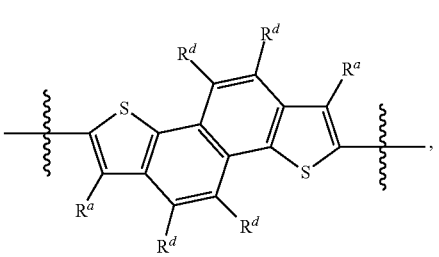

35
-continued
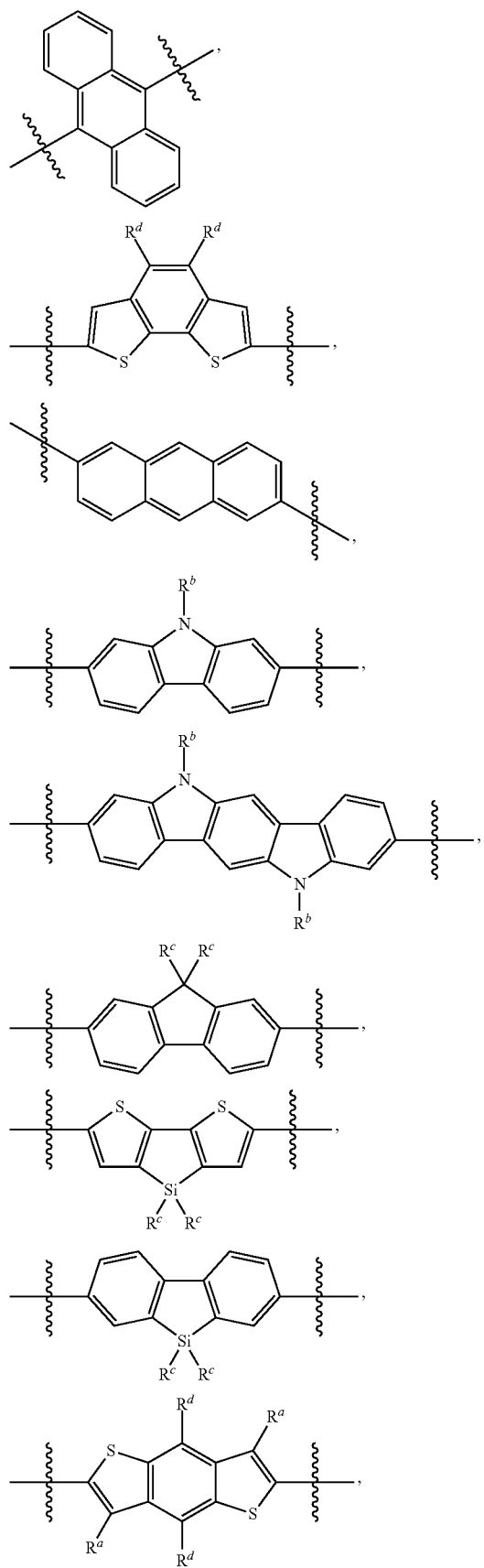
36
-continued
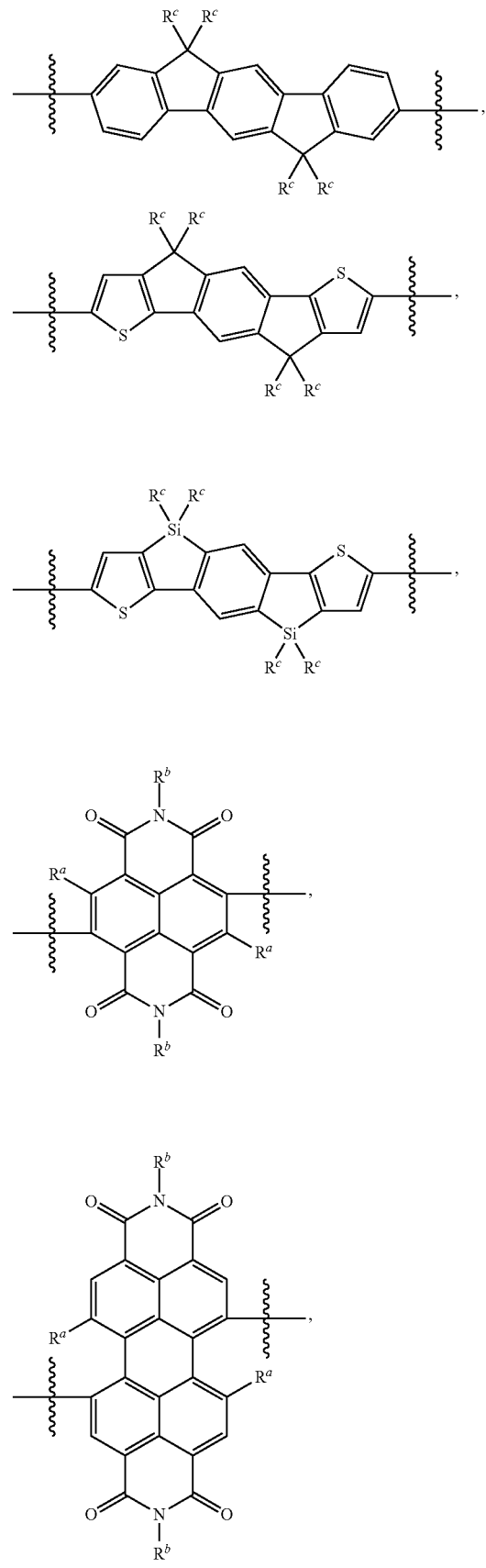

-continued
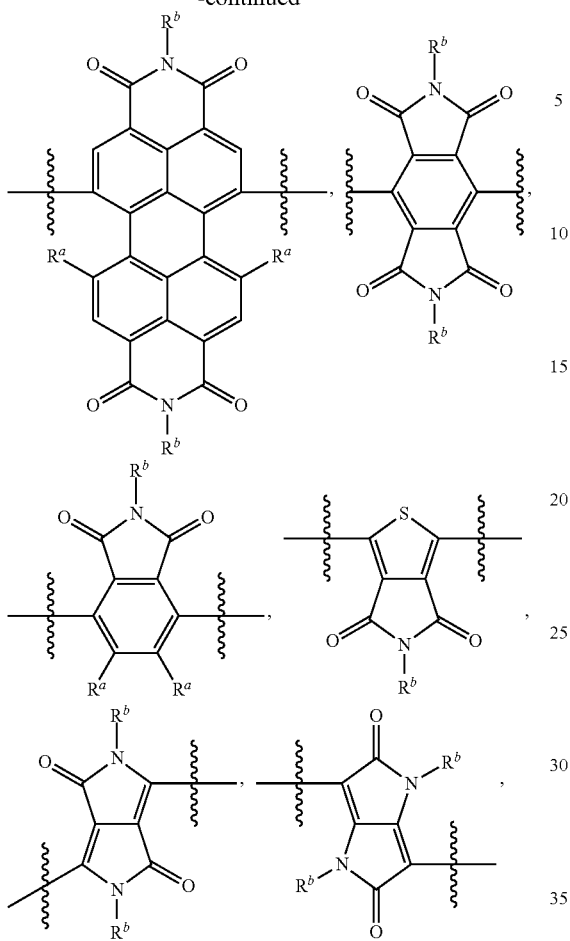
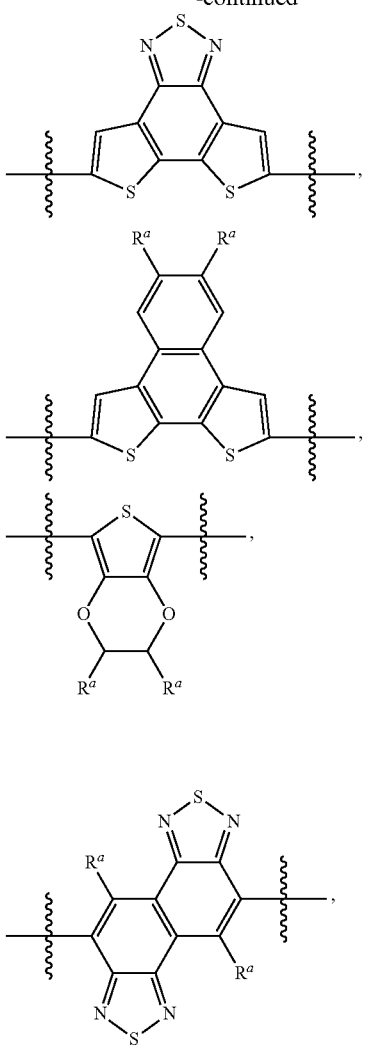
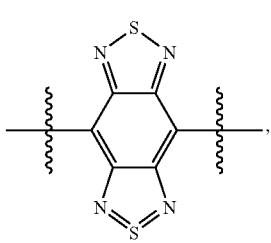

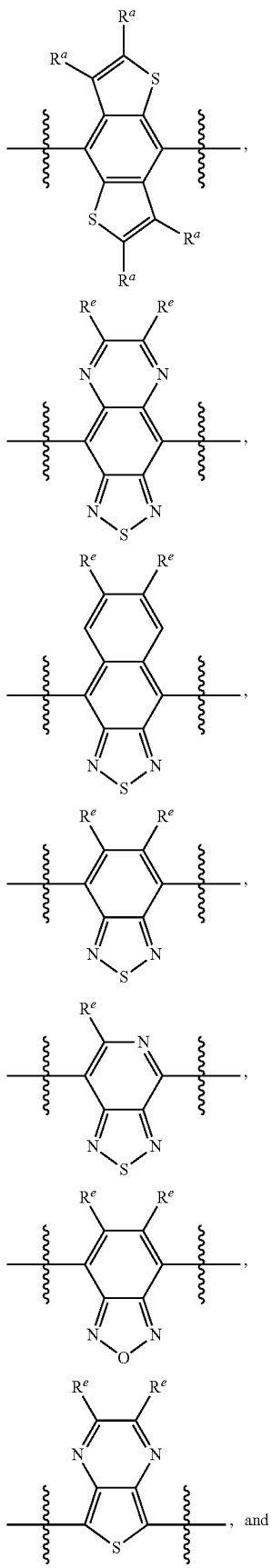

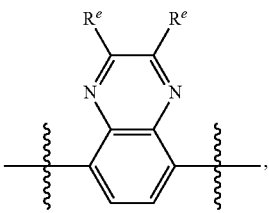

wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L'-$R^f$;

$R^c$ is H or R;

$R^d$ is selected from the group consisting of H, F, Cl, —CN, R, —OR, —SR, —C(O)R, —OC(O)R, —C(O)OR, and -L'-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L' is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

In yet other embodiments, $M_1$ can be selected from the group consisting of:

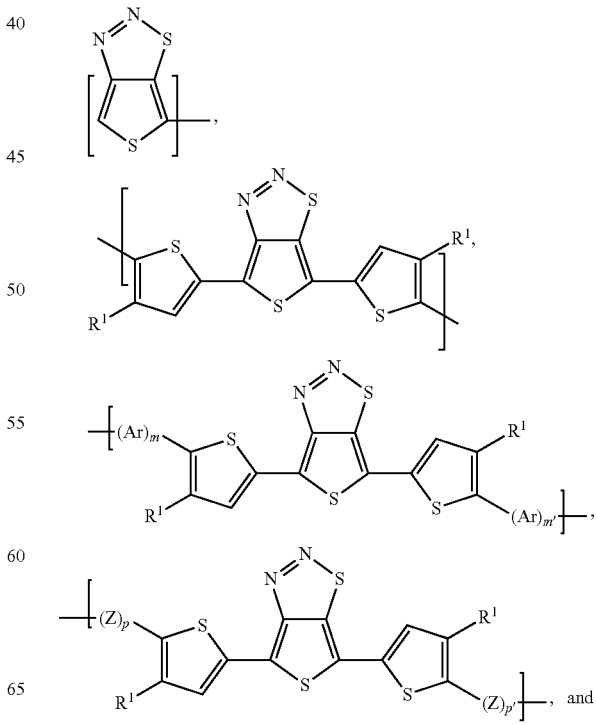

-continued
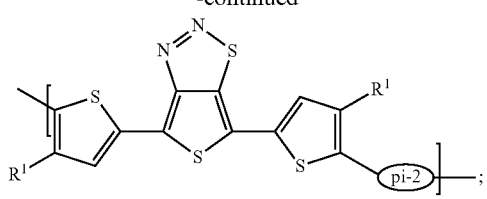
and
M₂ can have the formula:
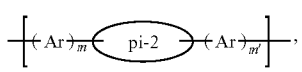
wherein Ar, pi-2, m and m' are as defined herein. Preferably, in both M₁ and M₂, each Ar in $(Ar)_m$ and $(Ar)_{m'}$ independently can be selected from the group consisting of:
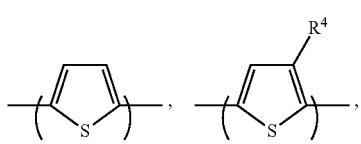
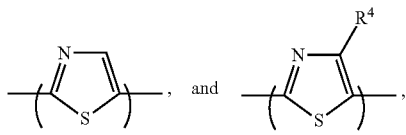
where $R^4$ is as defined herein, and pi-2 is selected from the group consisting of:
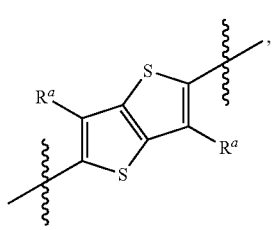
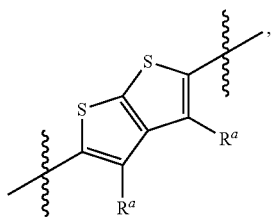
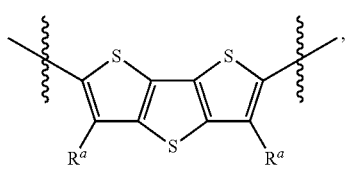
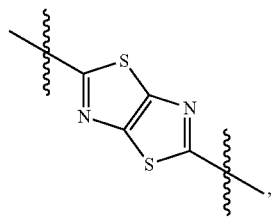
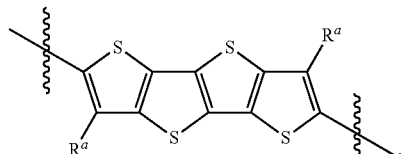
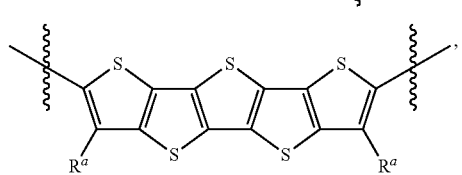
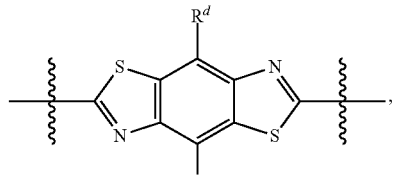
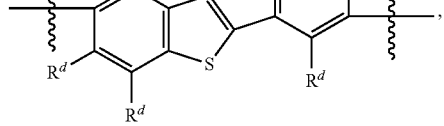
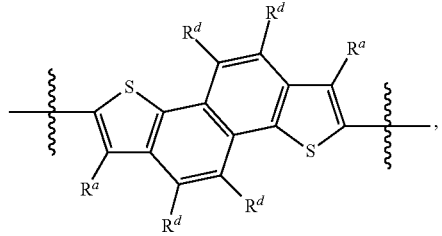
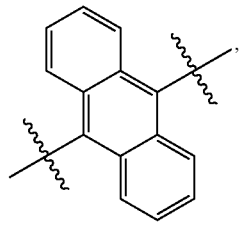
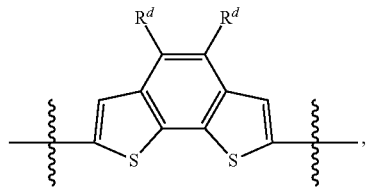

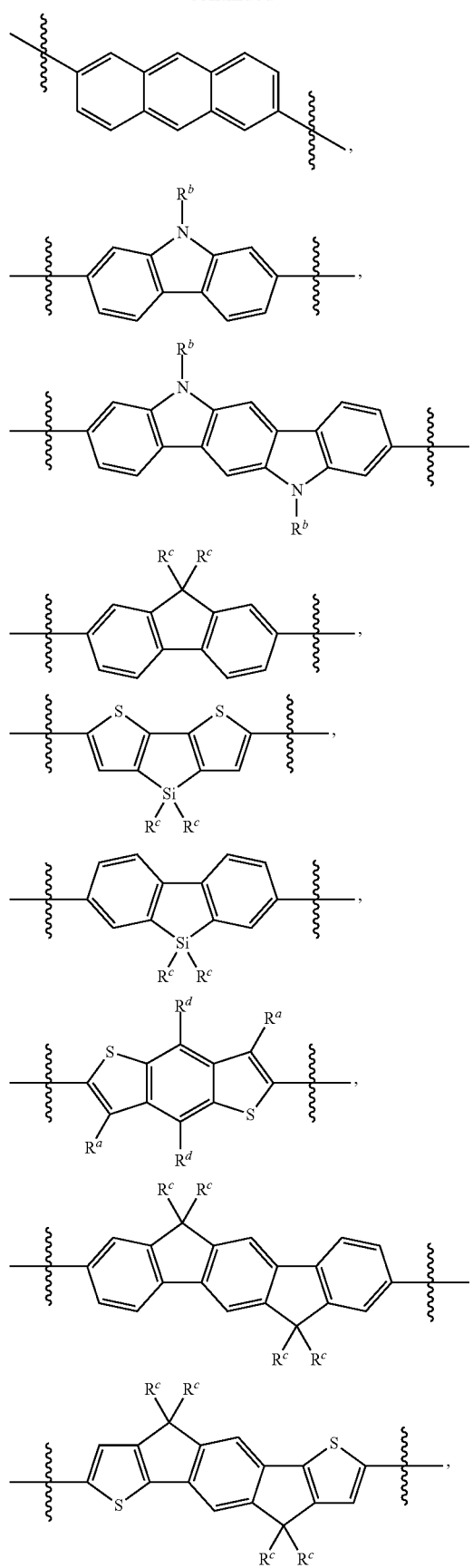
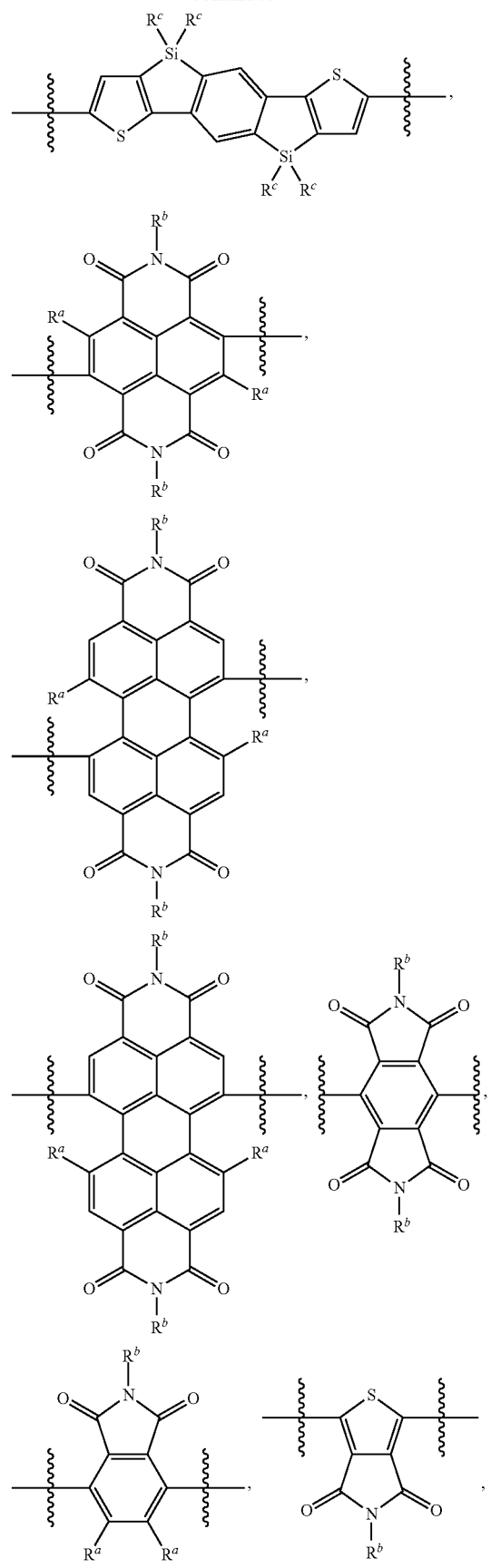

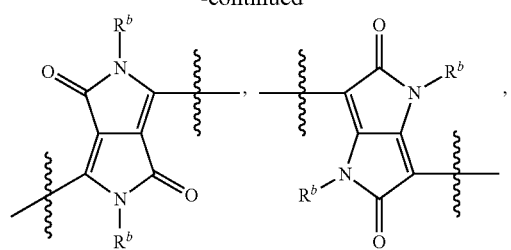
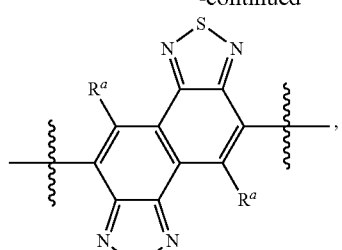
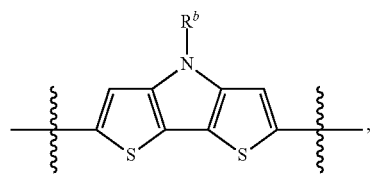
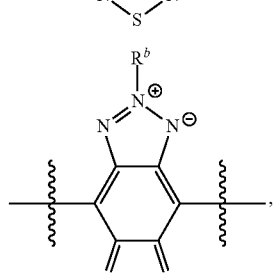
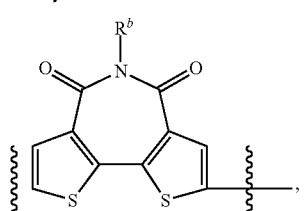
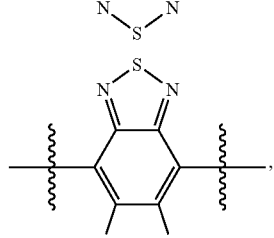
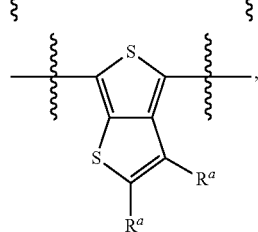
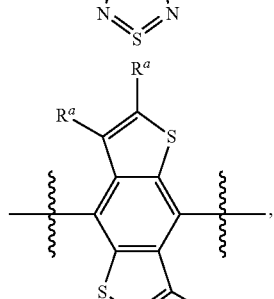
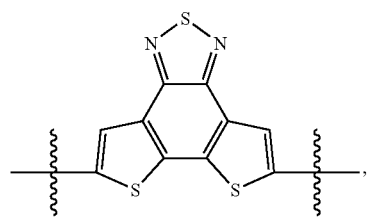
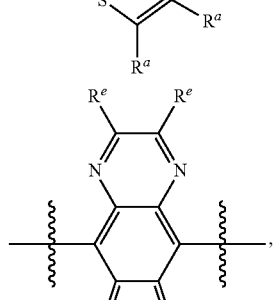
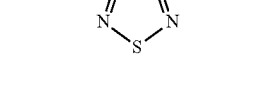
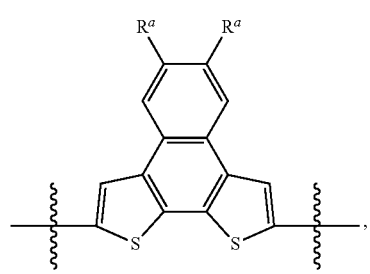
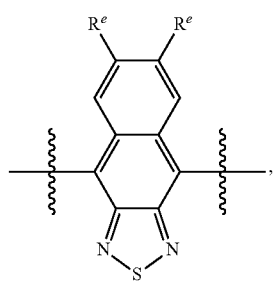
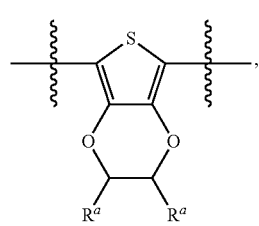

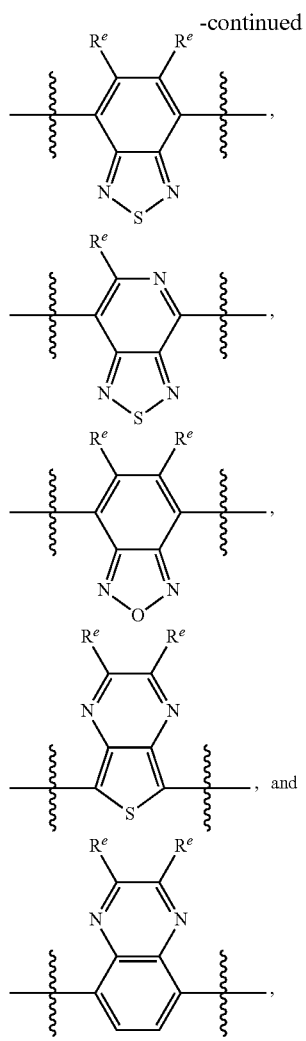

, and wherein:
R$^a$ is selected from the group consisting of H, F, Cl, —CN, R, —OR, —SR, —C(O)R, —OC(O)R, and —C(O)OR;
R$^b$ is selected from the group consisting of H, R, and -L'-R$^f$;
R$^c$ is H or R;
R$^d$ is selected from the group consisting of H, F, Cl, —CN, R, —OR, —SR, —C(O)R, —OC(O)R, —C(O)OR, and -L'-R$^f$;
R$^e$ is selected from the group consisting of H, F, Cl, —CN, R, —OR, —SR, —C(O)R, —OC(O)R, —C(O)OR, and R$^f$;
R$^f$ is a C$_{6-20}$ aryl group or a 5-20-membered heteroaryl group, each optionally substituted with 1-8 groups independently selected from the group consisting of F, Cl, —CN, R, —OR, and —SR;
L' is selected from the group consisting of —O—, —S—, —C(O)—, —OC(O)—, —C(O)O—, and a covalent bond; and
R is selected from the group consisting of a C$_{1-40}$ alkyl group, a C$_{1-40}$ haloalkyl group, a C$_{2-40}$ alkenyl group, and a C$_{2-40}$ alkynyl group.

In other embodiments, M$_2$ can have a formula selected from the group consisting of:

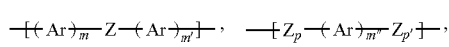

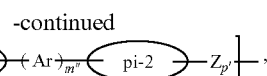
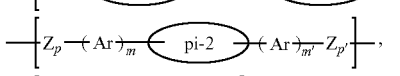
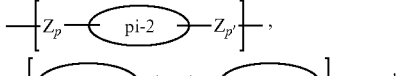
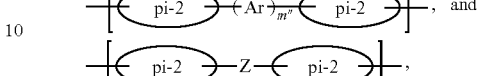

wherein m, m' and m" independently are 1, 2, 3 or 4; and Ar, pi-2 and Z are as defined herein.

In certain embodiments, the present polymers are copolymers of at least one M$_1$ repeating unit and at least one M$_2$ repeating unit, where each M$_1$ repeating unit independently can be:

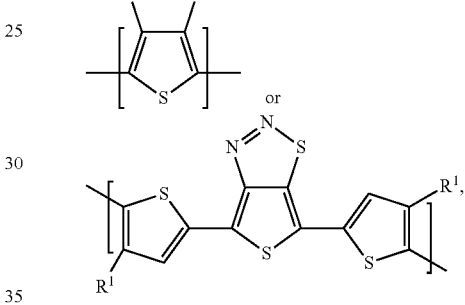

and each M$_2$ repeating unit independently can be selected from the group consisting of:

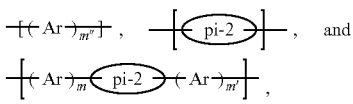

where pi-2, Ar, m, m', and m'" are as defined herein.

To illustrate, certain embodiments of the present polymers can be represented by the formula (V) or (VI):

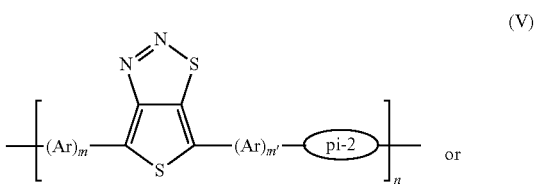
(V)

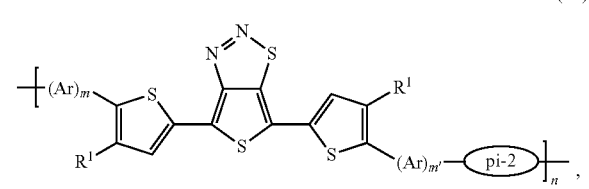
(VI)

where n is an integer ranging from 3 to 1,000. Preferably, each Ar in $(Ar)_m$ and $(Ar)_{m'}$ independently are selected from the group consisting of:

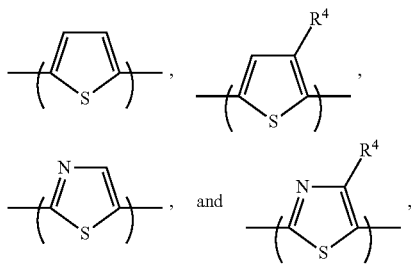

where $R^4$ is selected from the group consisting of a $C_{1-40}$ alkyl group, a $C_{1-40}$ alkoxy group, and a $C_{1-40}$ haloalkyl group; and pi-2 is selected from is selected from the group consisting of:

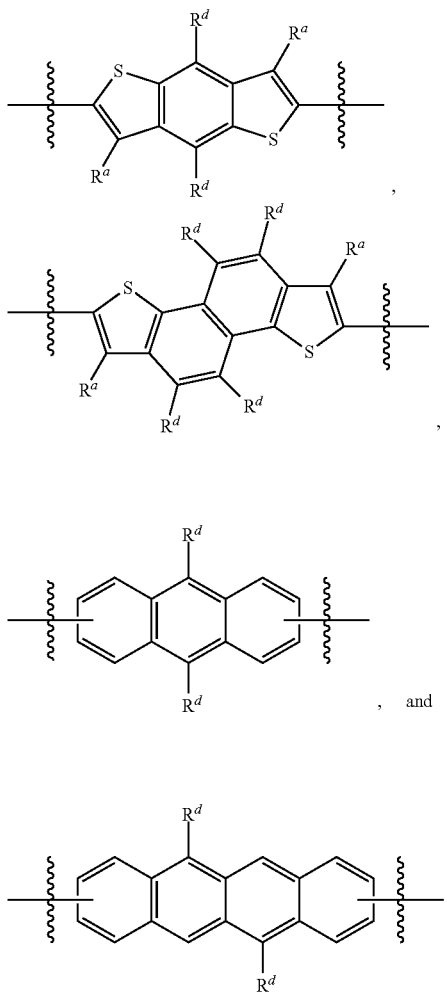

where $R^a$ and $R^d$ are as defined herein.

For the various polymers described above, the degree of polymerization (n) can be an integer between 3 and 1,000. In some embodiments, n can be 4-1,000, 5-1,000, 6-1,000, 7-1,000, 8-1,000, 9-1,000, or 10-1,000. For example, n can be 8-500, 8-400, 8-300, or 8-200. In certain embodiments, n can be 8-100. In particular embodiments, the molecular weight of the polymer can be at least 5,000 g/mol, preferably at least 10,000 g/mol.

Embodiments of the present compounds including $M_1$ and at least one $M_2$ can have the two units repeated in a random or alternating manner, and the mole fraction of the two units can be between about 0.05 and about 0.95. For example, the respective mole fractions (x and y) of the two units can be between about 0.1 and about 0.9, between about 0.2 and about 0.8, between about 0.3 and about 0.7, between about 0.4 and about 0.6, or between about 0.45 and about 0.55. In certain embodiments, the present polymers can include the same mole fraction of the first unit as the second unit (i.e., x=y=0.5).

Without wishing to be bound by any particular theory, it is believed that if n-channel transport is desired, the strong electron-depleted electronic structure enabled by $M_1$ copolymerized with a strong electron-depleted $M_2$ repeating unit, together with the regioregular highly π-conjugated polymeric backbone of the present polymers, can make the present polymers ambient-stable n-channel semiconductor materials. If large light absorption (extinction coefficient) is desired, the present polymers can be provided with a highly π-conjugated polymeric backbone and by having the $M_1$ unit copolymerized with an electron-donating $M_2$ comonomer to enable a push-pull structure. If an ambipolar polymer is desired, for example in light-emitting transistor applications, the present polymers can have a highly π-conjugated polymeric backbone comprising a copolymer of $M_1$ and an electron-neutral or electron-donating (electron-rich) $M_2$ unit.

In addition and without wishing to be bound by any particular theory, it is believed that polymers of the present teachings that have a regioregular polymeric backbone can lead to higher molecular weights, a more π-conjugated structure and, consequently better charge transport efficiencies. Accordingly, in preparing the present polymers, the present teachings can include isolating a particular average molecular weight fractions, and/or enriching and/or isolating a particular stereoisomer of $M_1$ and/or $M_2$ that has two or more stereoisomers.

The homopolymerization of $M_1$ and the copolymerization of $M_1$ and $M_2$ can be achieved via various reactions known to those skilled in the art, including procedures analogous to those described in Yamamoto, *J Organomet. Chem.*, 653: 195-199 (2002); Walton et al., Polymer Chemistry (Fred J. Davis ed. 2004), p. 158-187; and Galbrecht et al., *Macromolecular Rapid Communications*, 28(4): 387-394 (2007), the entire disclosure of each of which is incorporated by reference herein for all purposes. In particular, Stille coupling or Suzuki coupling reactions can be used to prepare polymeric compounds according to the present teachings with high molecular weights and in high yields (≥75%) and purity, as confirmed by $^1$H NMR spectra, elemental analysis, and/or GPC measurements. Scheme 1 below outlines several exemplary reactions that can be used to polymerize $M_1$ by itself or copolymerize $M_1$ with $M_2$. It should be understood that the polymerizable groups (e.g., $SnR_3$, $BR_2$, MgX, ZnX, and Br, where X is a halogen and R is an alkyl group) can be reversed between $M_1$ and $M_2$. Analogous reactions can be used to couple a moiety of formula (I) or (II) with Ar, pi-2, and/or Z moieties to provide a repeating unit $M_1$ including such Ar, pi-2, and/or Z moieties in addition to the moiety of formula (I) or (II).

Scheme 1

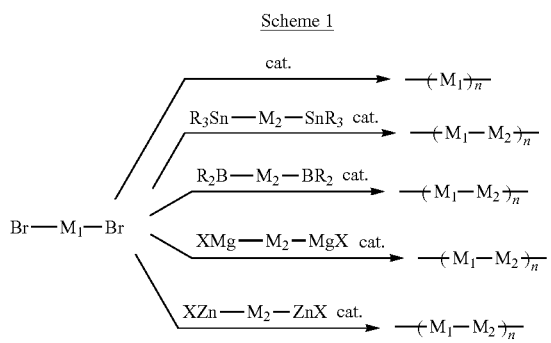

To illustrate, a polymer of formula (V) or (VI) can be obtained by copolymerizing a precursor of $M_1$ represented by

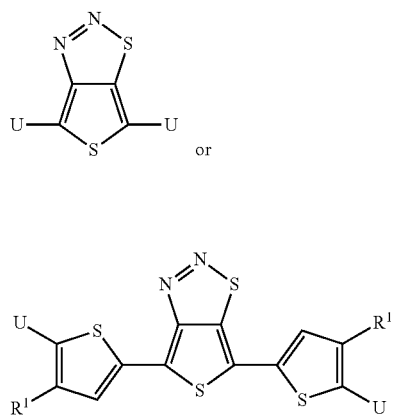

with a precursor of $M_2$ represented by

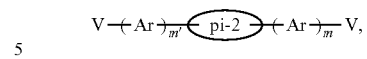

where U and V are complementary polymerizing groups. For example, referring to Scheme 1, U can be selected from the group consisting of $SnR_3$, $BR_2$, MgX, and ZnX (where X is a halogen and R is an alkyl group), and V can be Br; or vice versa. Alternatively, the same polymers can be obtained by copolymerizing a precursor of $M_1$ represented by

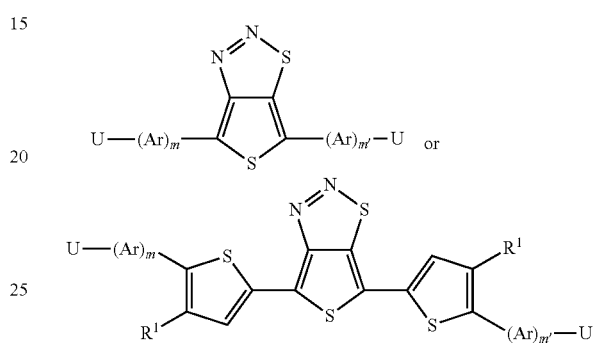

with a precursor of $M_2$ represented by

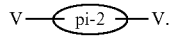

More specifically, a polymer according to the present teachings that includes an $M_1$ unit consists of only a moiety of formula (III) or (IV) and an $M_2$ unit consists of only a pi-2 moiety can be prepared as described in Scheme 2 below.

Scheme 2

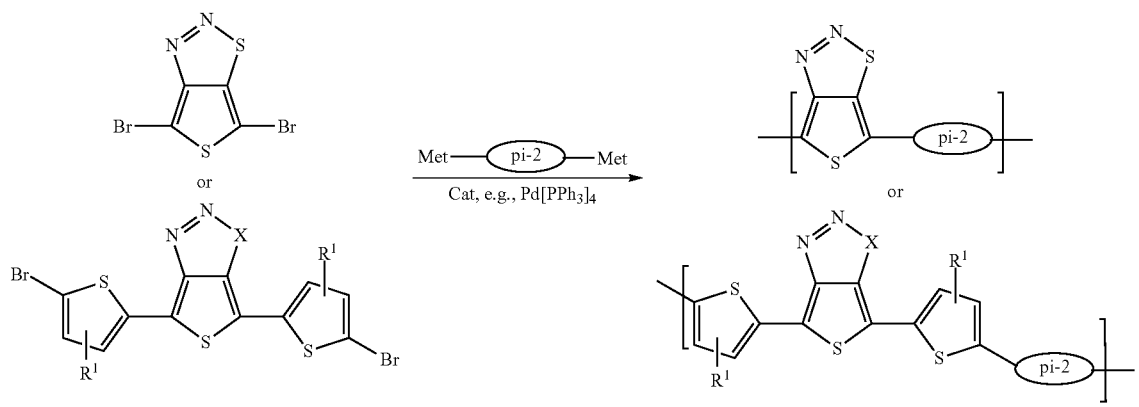

where

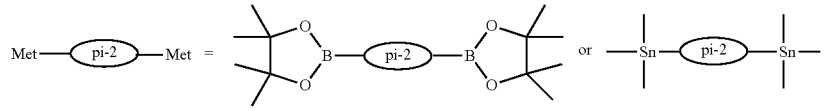

In embodiments where $M_1$ has the formula:
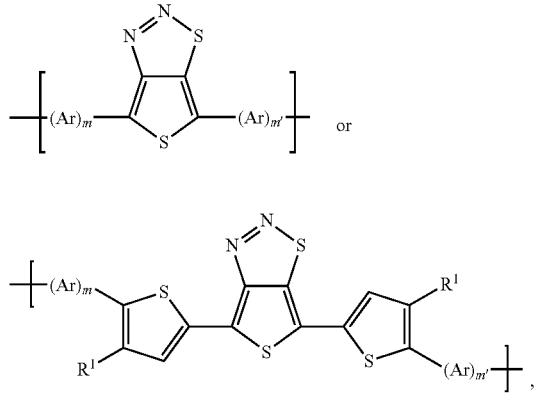
where more specifically, m and m' are 1 and each Ar is a substituted thiazolyl group, the dibromo-monomer below can be prepared then used in a subsequent polymerization step, e.g., to copolymerize with a repeating unit pi-2 as shown in Scheme 3 below, where $R^1$ and $R^3$ are each a dodecyl group.
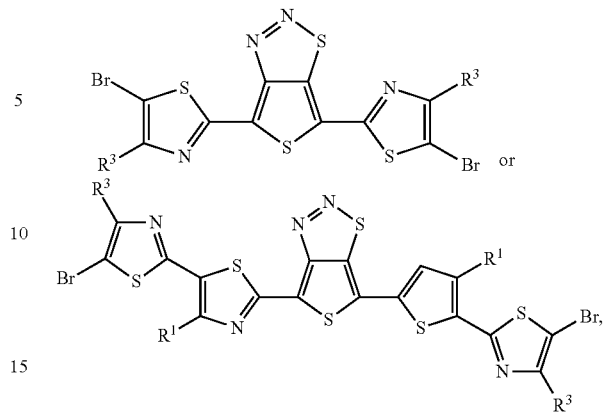
Scheme 3
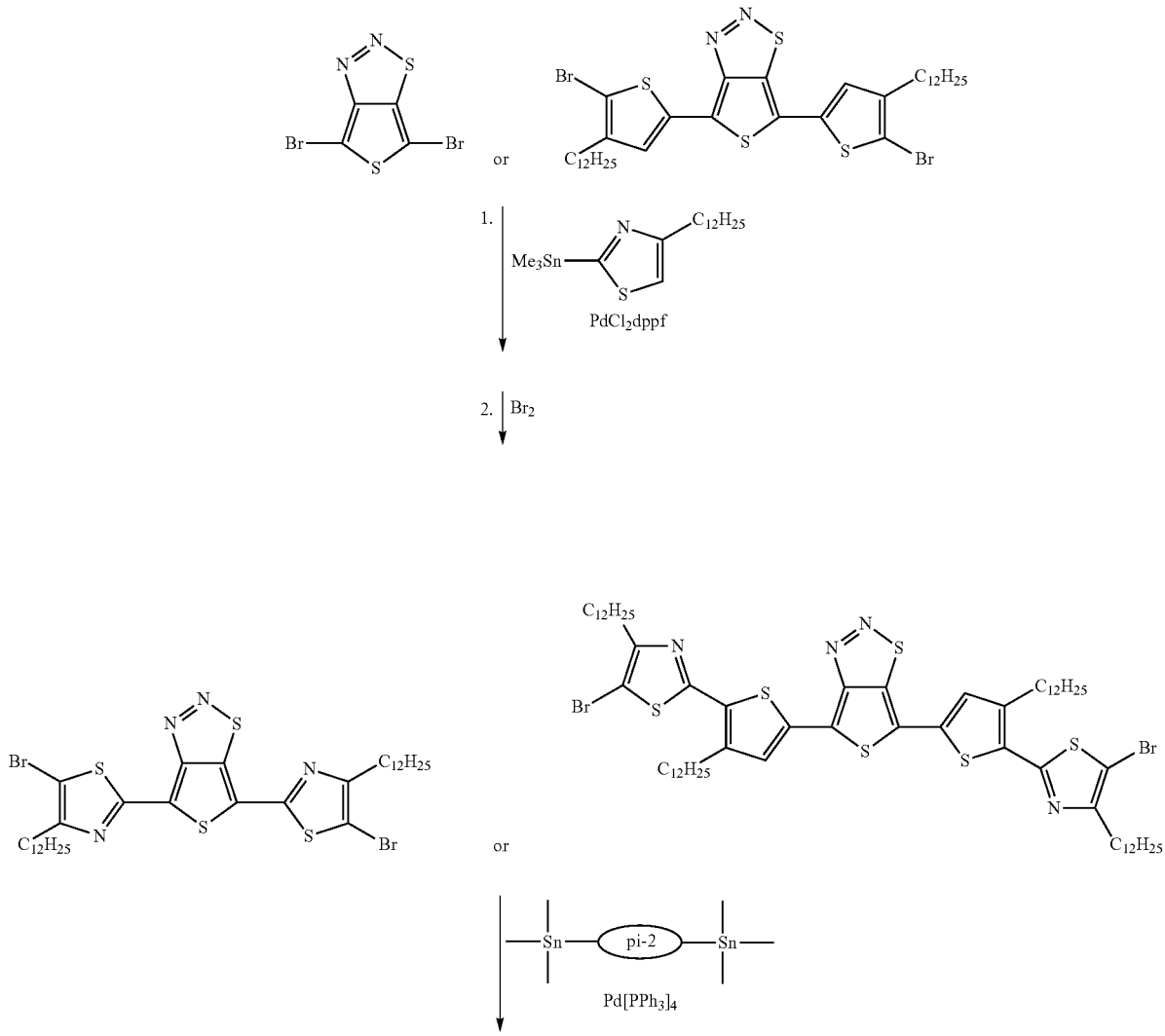

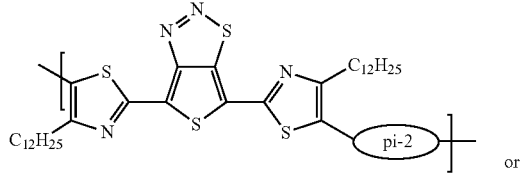

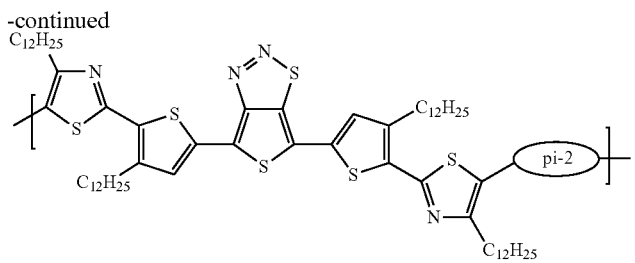

or

In another aspect, the present compounds can be molecular semiconductors (or semiconducting small molecule compounds) including one or more moieties represented by formula (I) and one or more linear conjugated moieties and/or one or more cyclic conjugated moieties other than the moieties represented by formula (I). More specifically, such molecular semiconductors can include one or more moieties represented by formula (I) and one or more monocyclic conjugated moieties (Ar), one or more polycyclic conjugated moieties (pi-2) other than the moieties represented by formula (I), and/or one or more linear (noncyclic) conjugated moieties (Z). In certain embodiments, a compound according to the present teachings can be a molecular semiconductor including one or more moieties represented by formula (II).

In some embodiments, molecular semiconductors according to the present teachings can be represented by formula (VII) or (VIII):

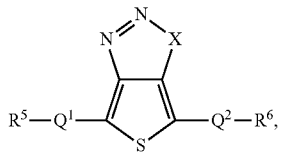
(VII)

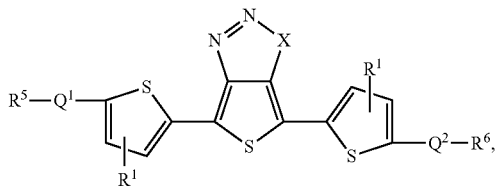
(VIII)

wherein:
$Q^1$ and $Q^2$ independently can be selected from the group consisting of:

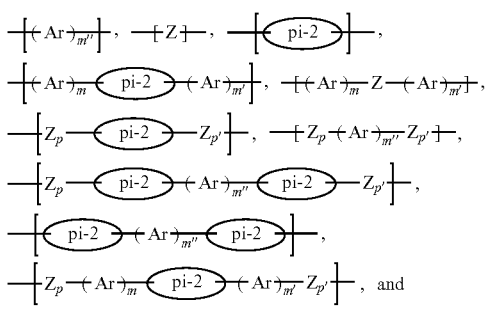

-continued

$R^5$ and $R^6$ independently can be selected from the group consisting of H, $R^2$, $OR^2$, $SR^2$, $C(O)R^2$, $OC(O)R^2$, and $C(O)OR^2$, where $R^2$ is selected from the group consisting of a $C_{1-40}$ alkyl group, a $C_{2-40}$ alkenyl group, a $C_{2-40}$ alkynyl group, and a $C_{1-40}$ haloalkyl group;
and $R^1$, X, Ar, pi-2, Z, m, m', m", p and p' are as defined herein.

For example, for compounds of formula (VII) or (VIII), $R^1$, at each occurrence, independently can be selected from the group consisting of H, halogen, —CN, $NO_2$, $R^2$, -L-$R^3$, OH, $OR^2$, $OR^3$, $NH_2$, $NHR^2$, $N(R^2)_2$, $NHR^3$, $NR^2R^3$, N$(R^3)_2$, SH, $SR^2$, $SR^3$, $S(O)_2OH$, —$S(O)_{2O}R^2$, —$S(O)_2OR^3$, $C(O)H$, $C(O)R^2$, $C(O)R^3$, $C(O)OH$, $C(O)OR^2$, $C(O)OR^3$, $C(O)NH_2$, $C(O)NHR^2$, $C(O)N(R^2)_2$, $C(O)NHR^3$, $C(O)NR^2R^3$, $C(O)N(R^3)_2$, $SiH_3$, $SiH(R^2)_2$, $SiH_2(R^2)$, and $Si(R^2)_3$, wherein L can be selected from the group consisting of a divalent $C_{1-40}$ alkyl group, a divalent $C_{2-40}$ alkenyl group, a divalent $C_{1-40}$ haloalkyl group, and a covalent bond; $R^2$ can be selected from the group consisting of a $C_{1-40}$ alkyl group, a $C_{2-40}$ alkenyl group, a $C_{2-40}$ alkynyl group, and a $C_{1-40}$ haloalkyl group; $R^3$ can selected from the group consisting of a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents selected from the group consisting of a halogen, —CN, $NO_2$, $R^2$, $OR^2$, and $SR^2$;

X can be O, S, or Se, and preferably, X is S;

Ar, at each occurrence, independently can be an optionally substituted 5- or 6-membered aryl or heteroaryl group; and preferably, $(Ar)_m$, $(Ar)_{m'}$, and $(Ar)_{m''}$ independently can be selected from the group consisting of:

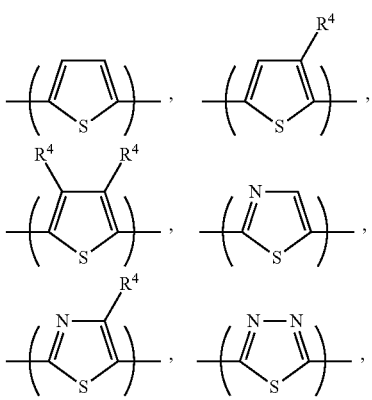

-continued
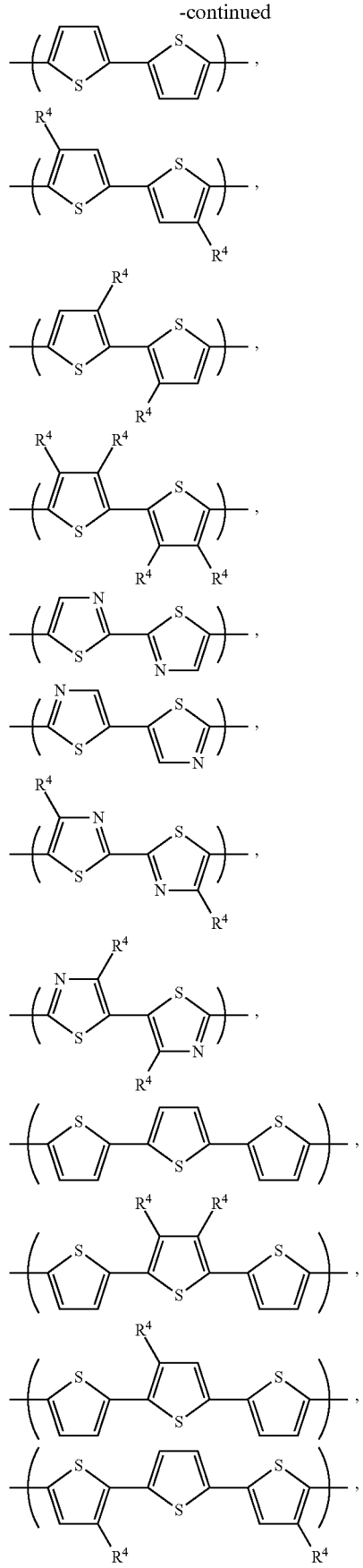
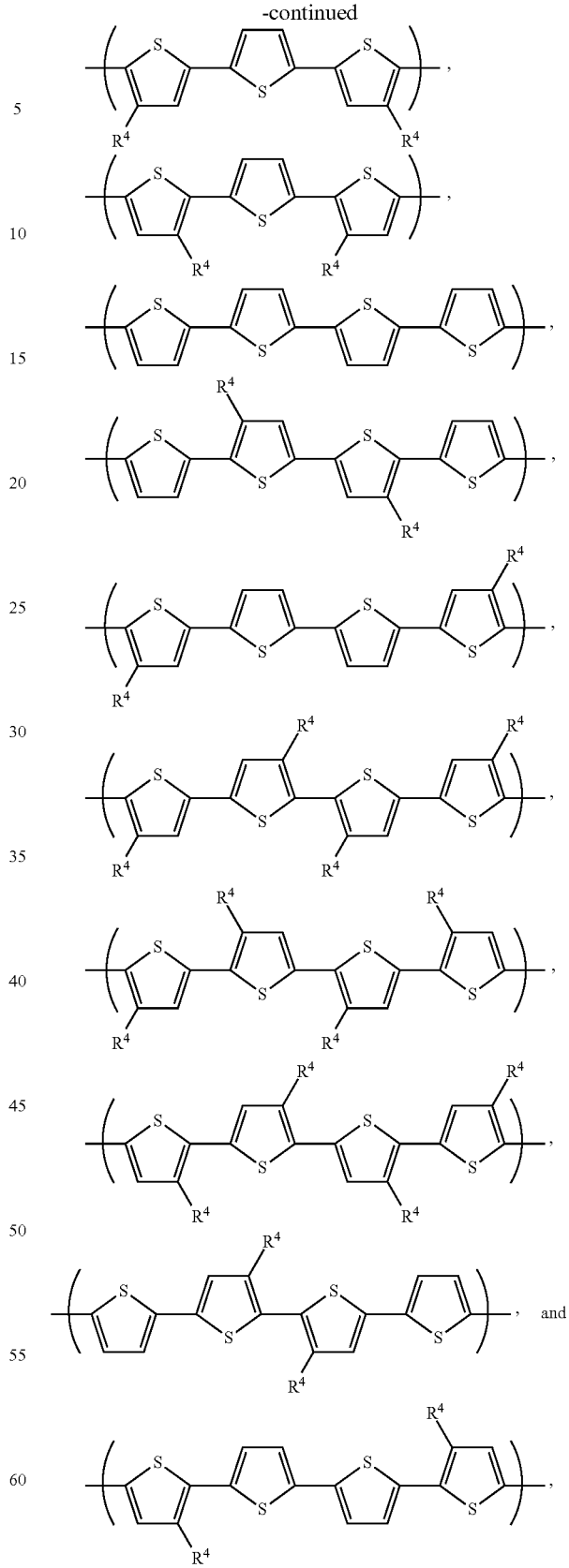
where R⁴ can be selected from the group consisting of F, Cl, —CN, R², OR², SR², C(O)R², OC(O)R², and C(O)OR², wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group;
pi-2 can be an optionally substituted conjugated polycyclic moiety such as:
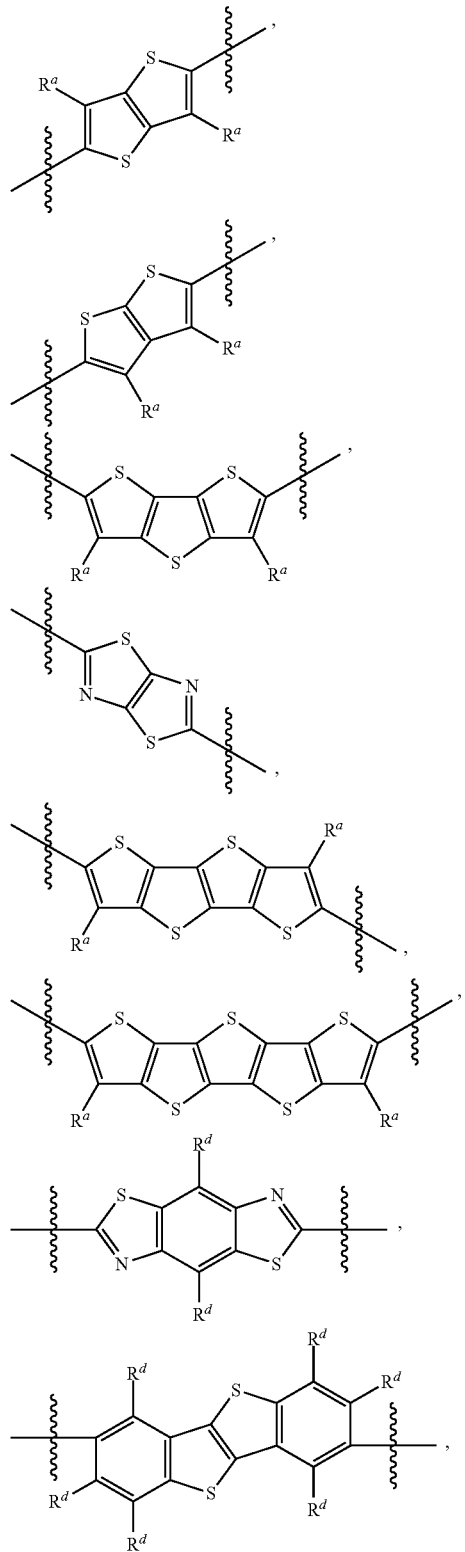
-continued
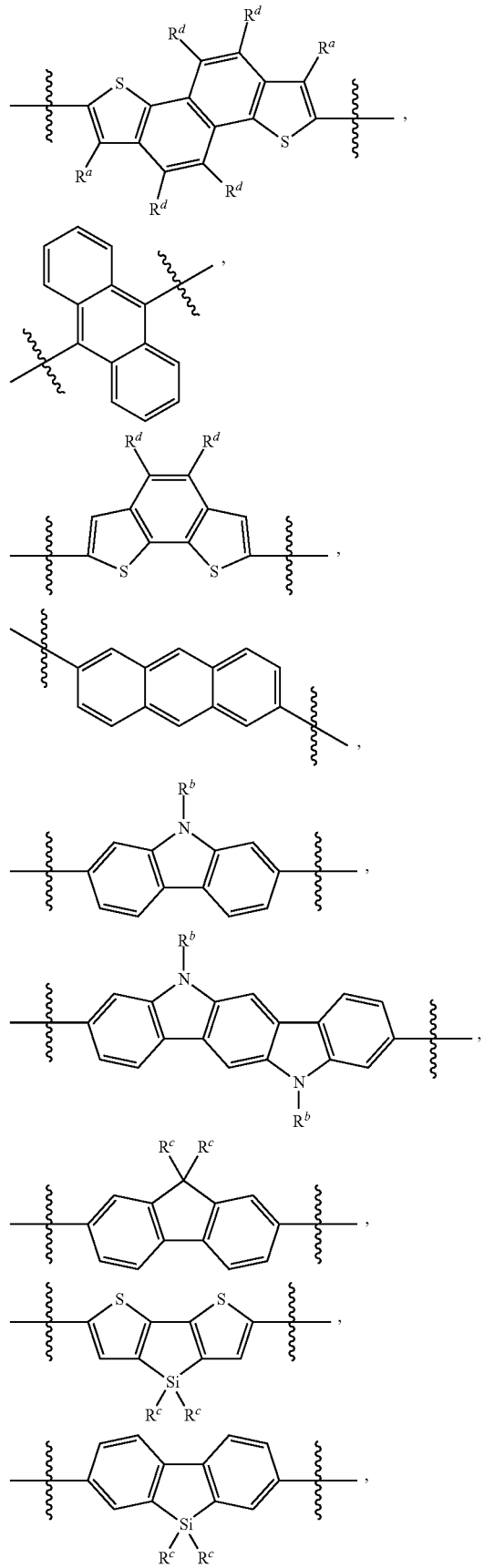

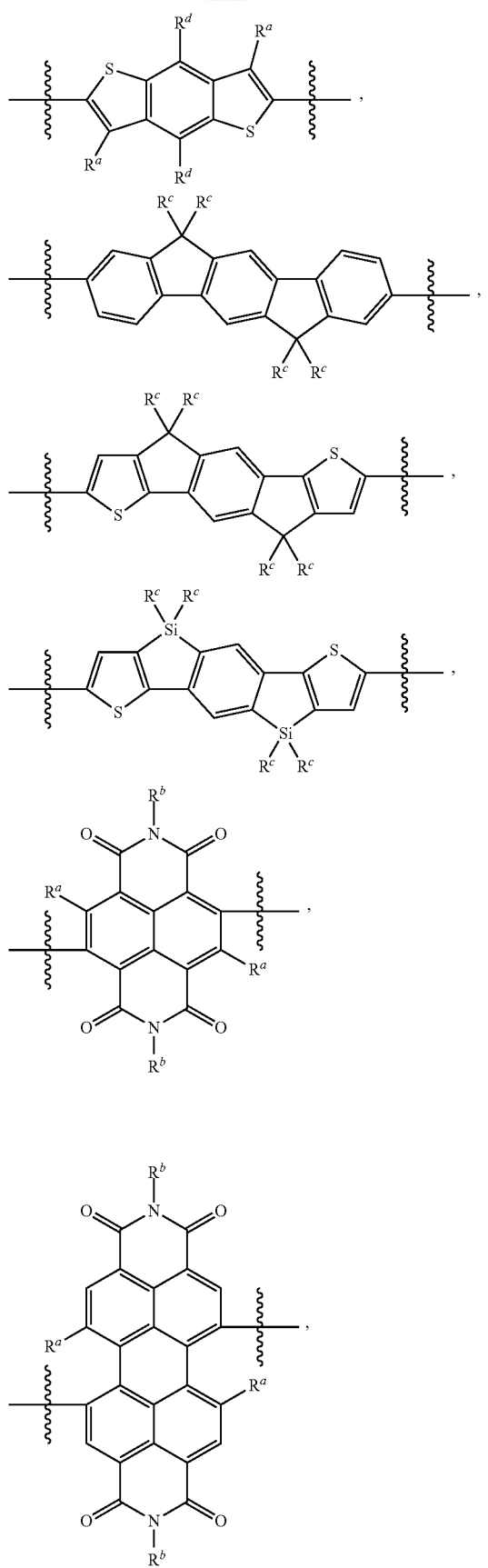
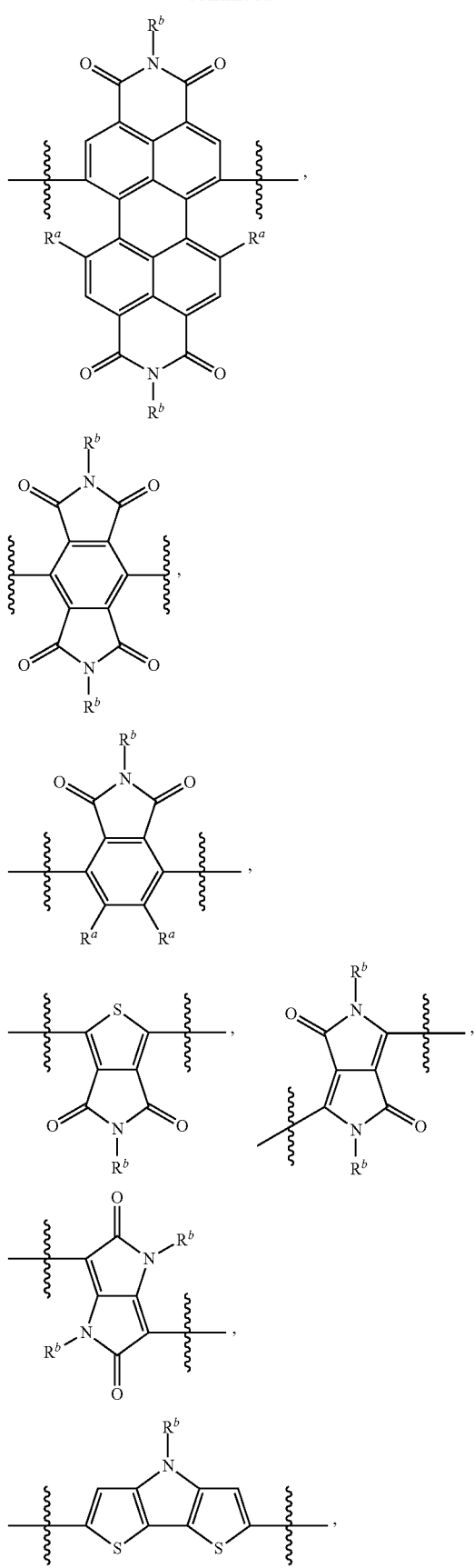

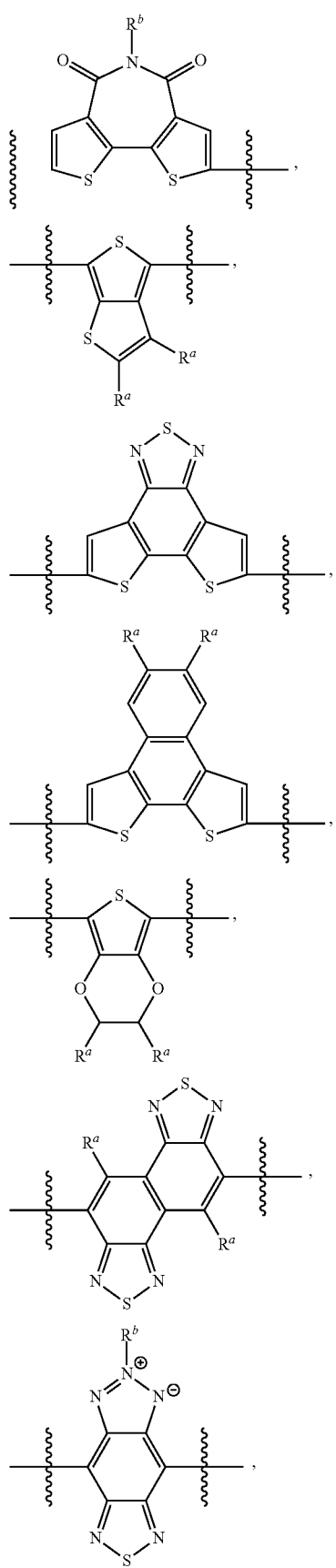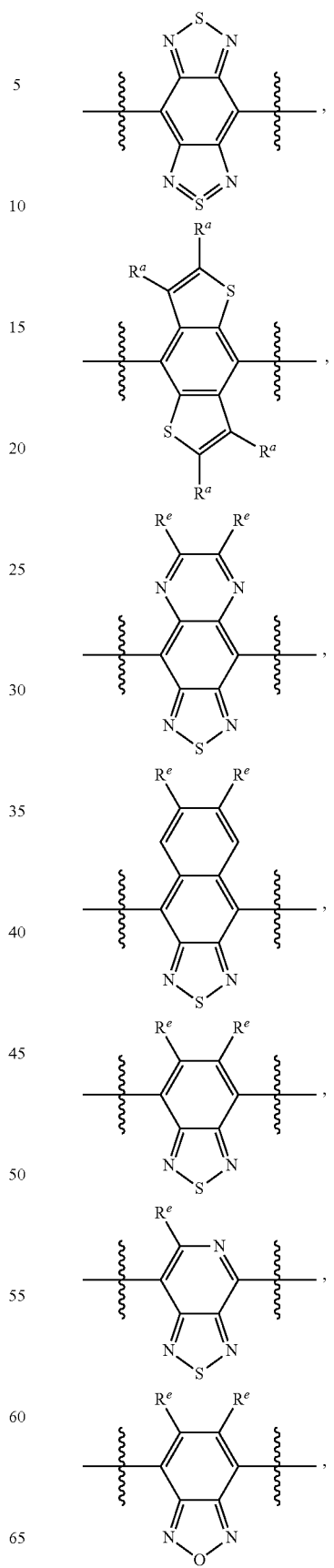

-continued

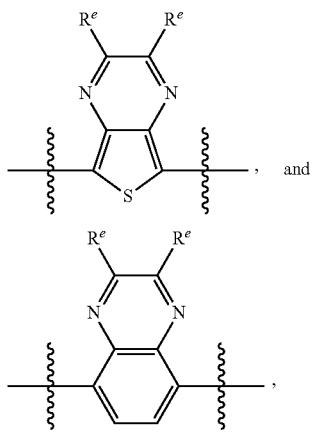
, and wherein:

$R^a$ is selected from the group consisting of H, F, Cl, —CN, R, —OR, —SR, —C(O)R, —OC(O)R, and —C(O)OR;

$R^b$ is selected from the group consisting of H, R, and -L'-$R^f$;

$R^c$ is H or R;

$R^d$ is selected from the group consisting of H, F, Cl, —CN, R, —OR, —SR, —C(O)R, —OC(O)R, —C(O)OR, and -L'-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L' is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group; and Z can be a conjugated noncyclic linker optionally selected from the group consisting of:

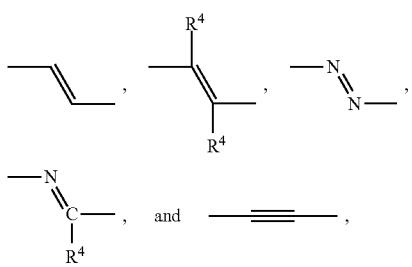

where $R^4$ can be selected from the group consisting of F, Cl, —CN, $R^2$, $OR^2$, $SR^2$, $C(O)R^2$, $OC(O)R^2$, and $C(O)OR^2$, where $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

In certain embodiments, the present compound can be a small molecule represented by formula (IX) or (X):

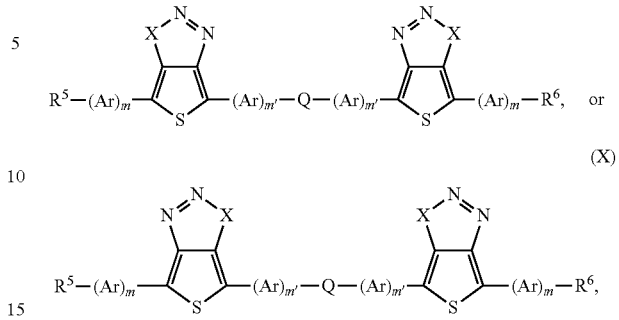

where Q can be absent or Q can be selected from the group consisting of:

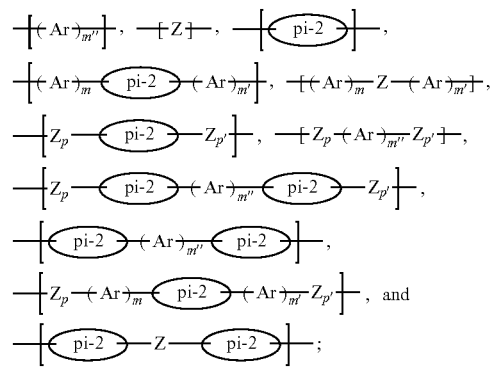

$R^5$ and $R^6$ independently can be selected from the group consisting of H, $R^2$, $OR^2$, $SR^2$, $C(O)R^2$, $OC(O)R^2$, and $C(O)OR^2$, where $R^2$ is selected from the group consisting of a $C_{1-40}$ alkyl group, a $C_{2-40}$ alkenyl group, a $C_{2-40}$ alkynyl group, and a $C_{1-40}$ haloalkyl group; and X, Ar, pi-2, Z, m, m', m'', p and p' are as defined herein.

For example, for compounds of formula (IX) or (X), Q can be selected from the group consisting of:

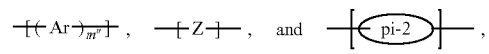

and X can be S.

In certain embodiments, Q can be selected from the group consisting of:

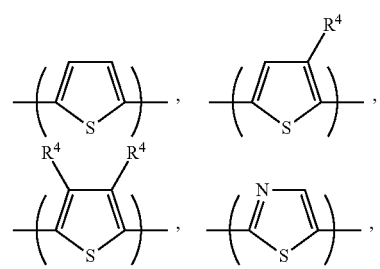

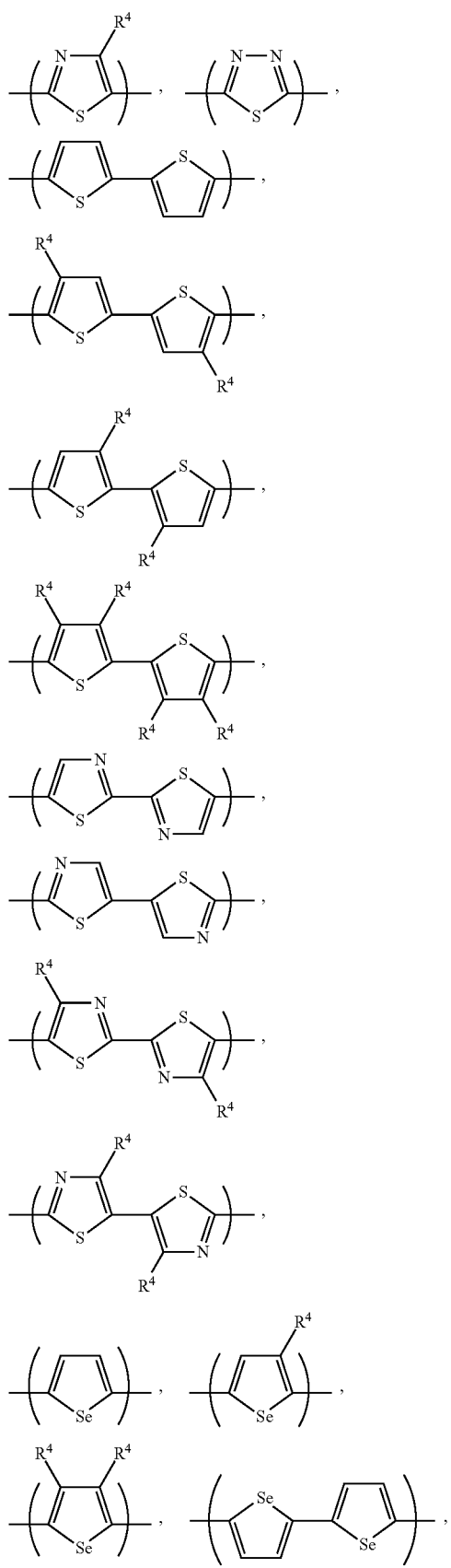
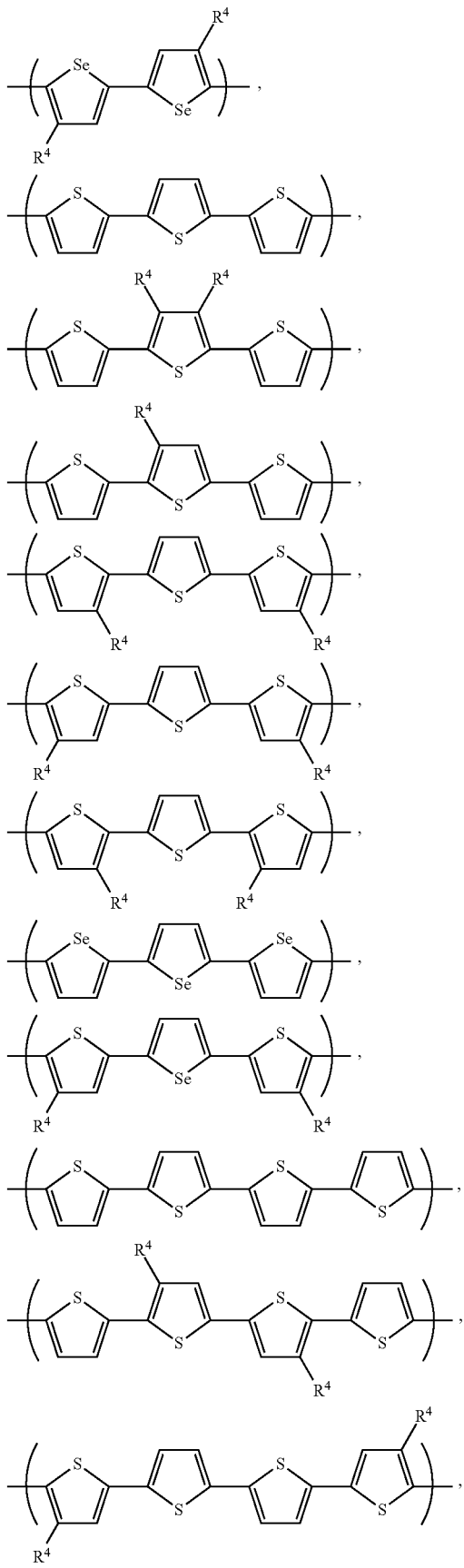

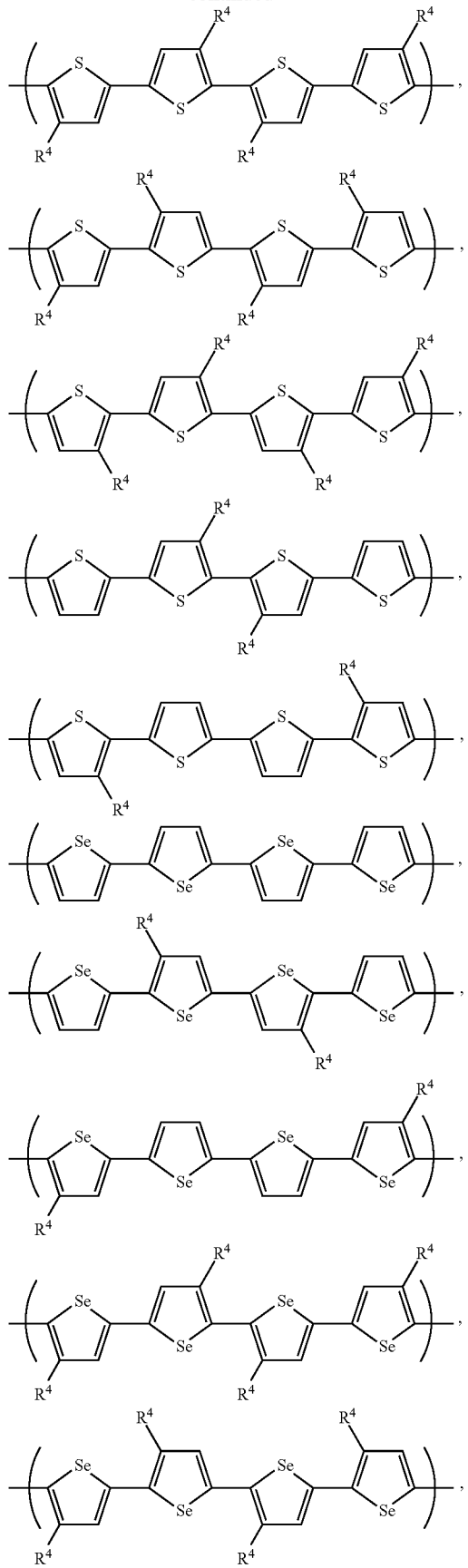

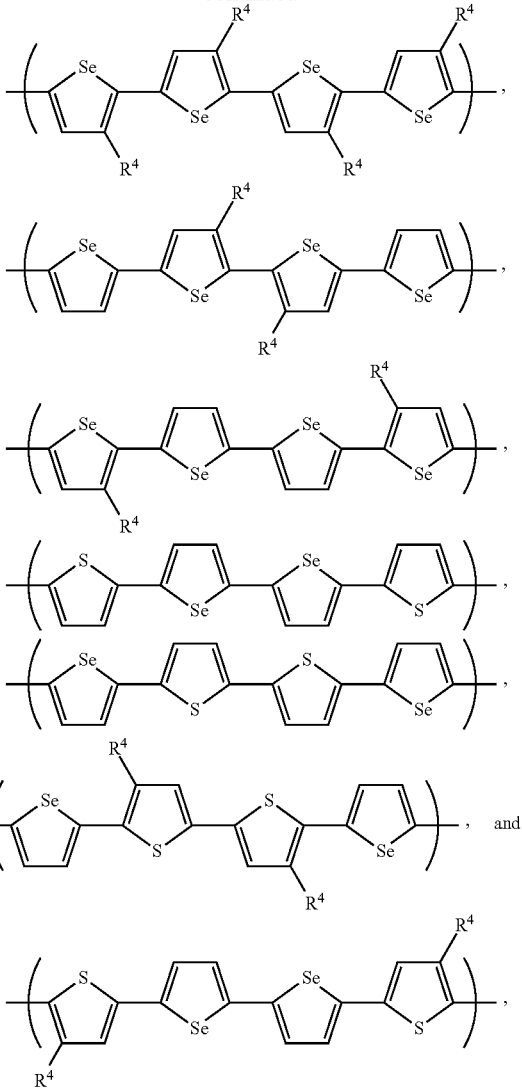

wherein each R⁴ independently can be selected from the group consisting of F, Cl, CN, $R^2$, $OR^2$, and $SR^2$, where $R^2$ is a linear or branched $C_{1-40}$ alkyl or haloalkyl group.

In certain embodiments, Q can be selected from the group consisting of:

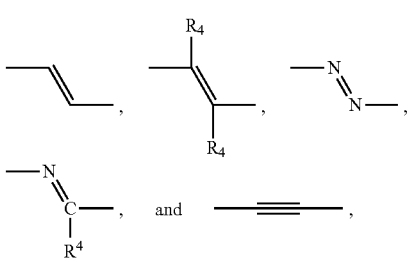

wherein R⁴ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

In certain embodiments, Q can be selected from the group consisting of:
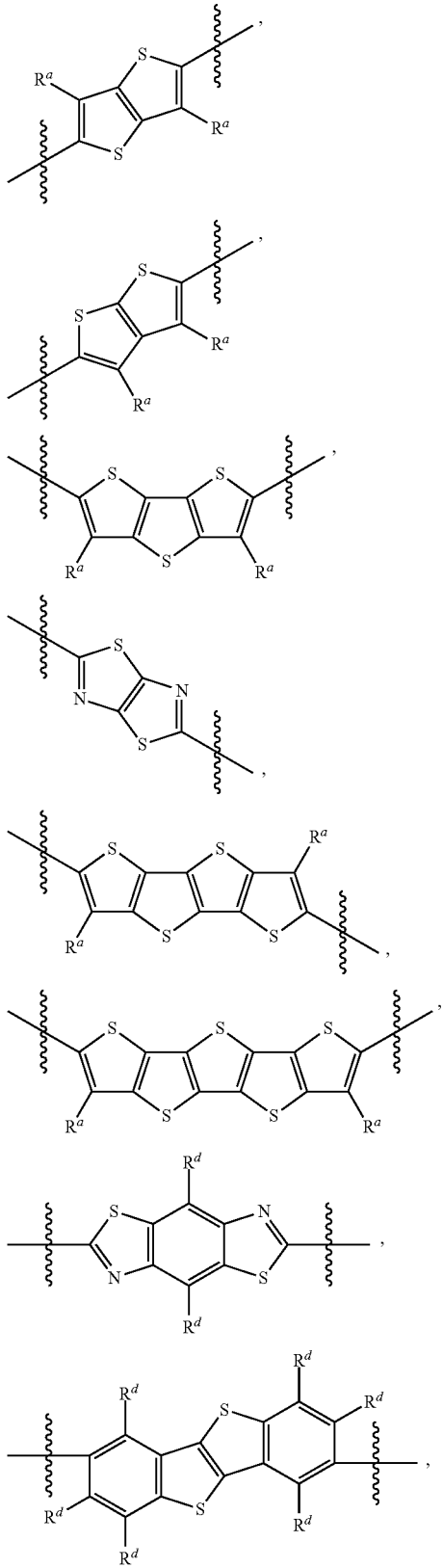
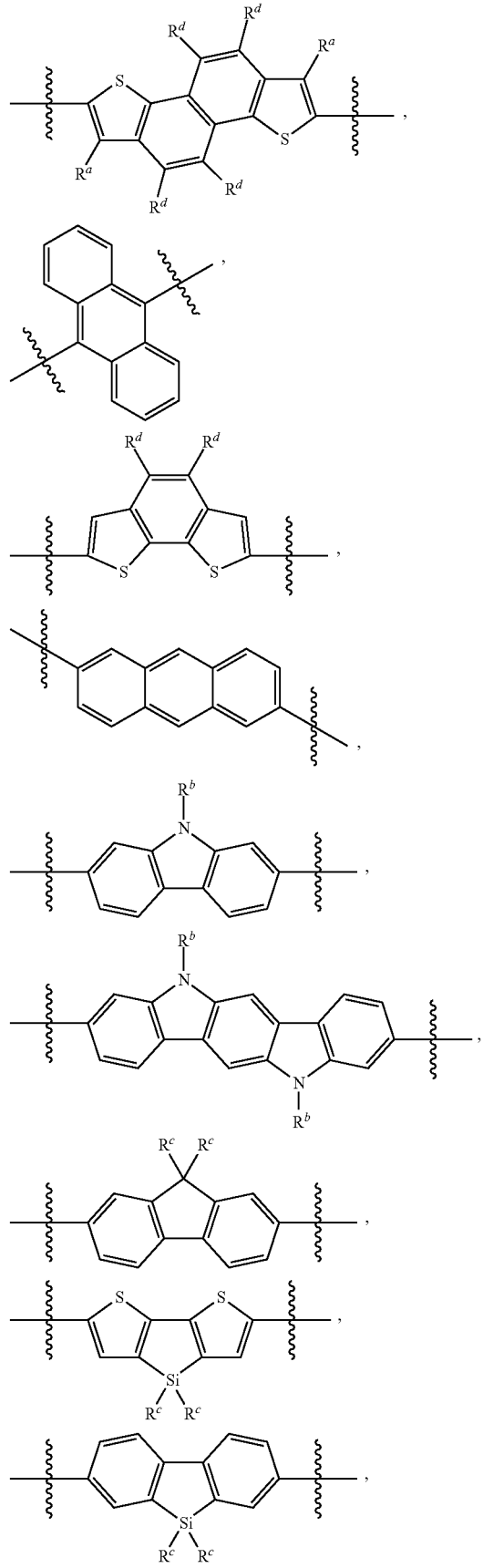

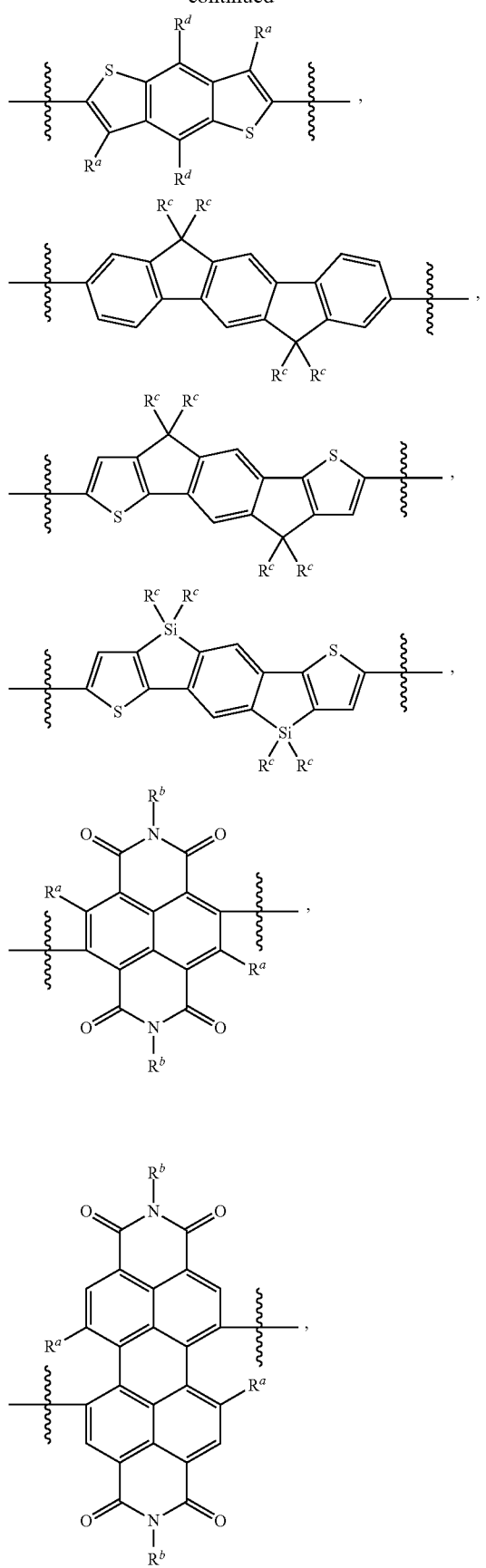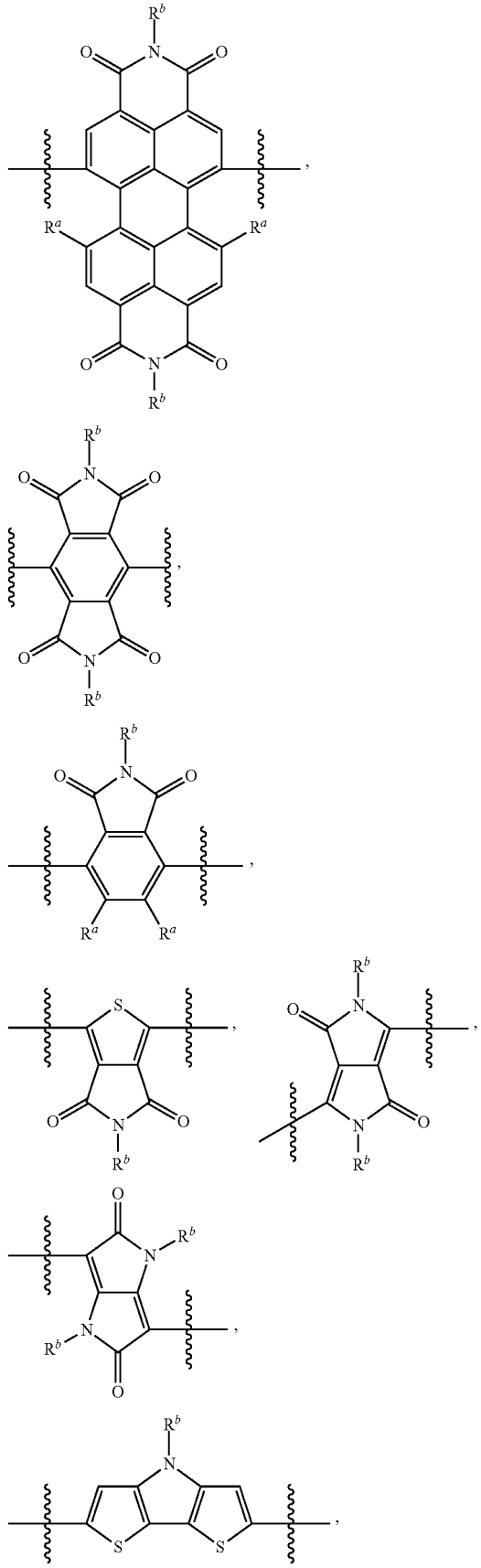

75
-continued
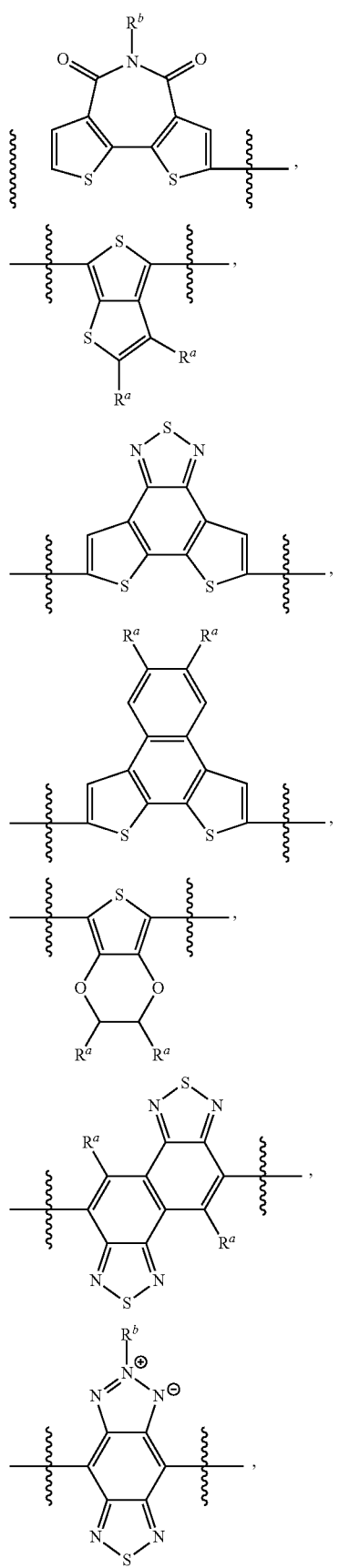
76
-continued
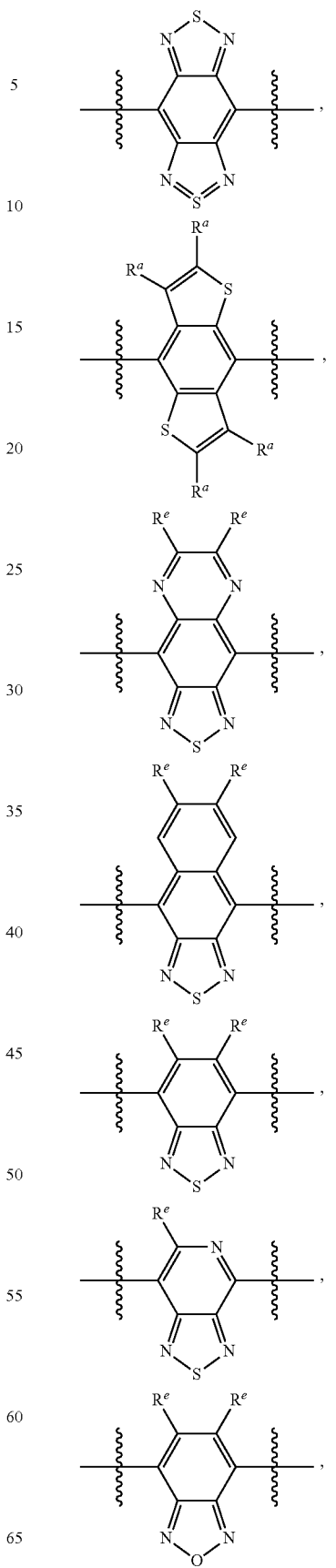

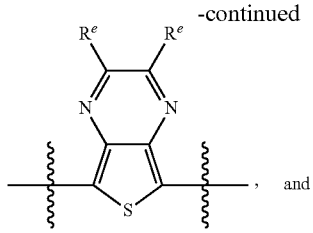, and

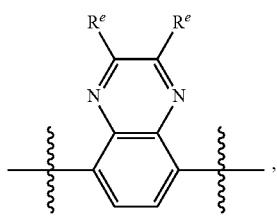, wherein:

$R^a$ is selected from the group consisting of H, F, Cl, —CN, R, —OR, —SR, —C(O)R, —OC(O)R, and —C(O)OR;
$R^b$ is selected from the group consisting of H, R, and -L'-$R^f$;
$R^c$ is H or R;
$R^d$ is selected from the group consisting of H, F, Cl, —CN, R, —OR, —SR, —C(O)R, —OC(O)R, —C(O)OR, and -L'-$R^f$;
$R^e$ is selected from the group consisting of H, F, Cl, —CN, R, —OR, —SR, —C(O)R, —OC(O)R, —C(O)OR, and $R^f$;
$R^f$ is a $C_{6-20}$ aryl group or a 5-20-membered heteroaryl group, each optionally substituted with 1-8 groups independently selected from the group consisting of F, Cl, —CN, R, —OR, and —SR;
L' is selected from the group consisting of —O—, —S—, —C(O)—, —OC(O)—, —C(O)O—, and a covalent bond; and
R is selected from the group consisting of a $C_{1-40}$ alkyl group, a $C_{1-40}$ haloalkyl group, a $C_{2-40}$ alkenyl group, and a $C_{2-40}$ alkynyl group.

In some embodiments comprising compounds of formula (IX) or (X), one of m and m' can be 0 while the other of m and m' can be 1, 2, 3, 4, 5 or 6. Accordingly, these compounds can be represented by formula (XI), (XII), (XIII) or (XIV):

(XI)

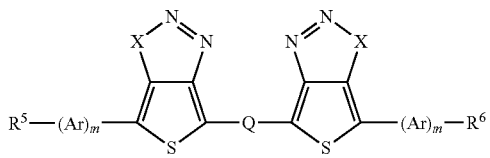

(XII)

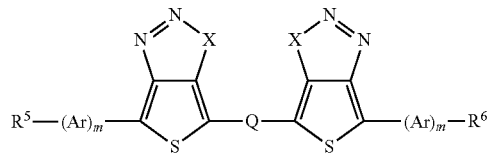

(XIII)

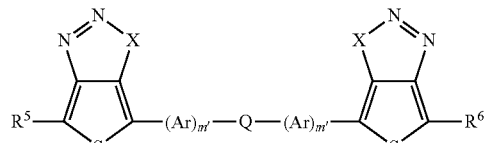

(XIV)

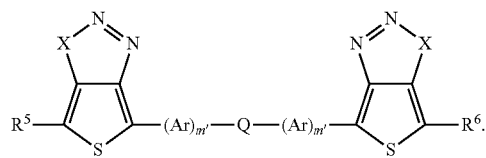

In some embodiments comprising compounds of formula (IX) or (X), Q can be absent provided at least one of m and m' is not 0. Accordingly, these compounds can be represented by formula (XV) or (XVI):

(XV)

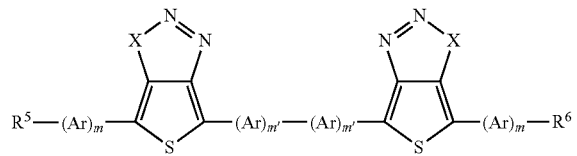

(XVI)

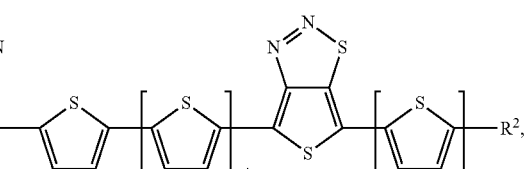

Exemplary molecular semiconductors according to the present teachings can include those represented by the formula:

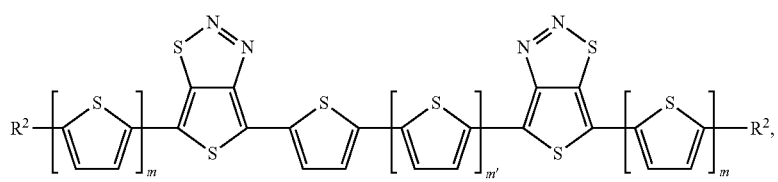

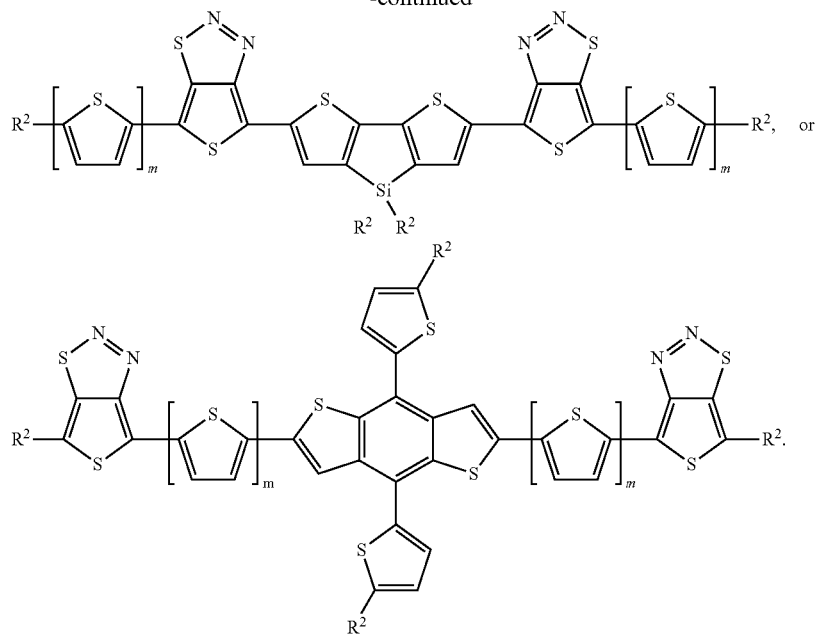

Molecular semiconductors and monomers according to the present teachings can be prepared using synthetic routes described in Scheme 4-10. Other monomers according to the present teachings can be commercially available, known in the literature, or can be prepared from readily prepared intermediates by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), optical absorption/emission spectroscopy (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

For example, the moiety represented by formula (III) can be prepared according to one of the reactions shown in Scheme 4 below. Example of diazotization procedures can be found in the following reference: Mo, Fanyang et al., Organic & Biomolecular Chemistry (2013), 11(10), 1582-1593.

Scheme 4

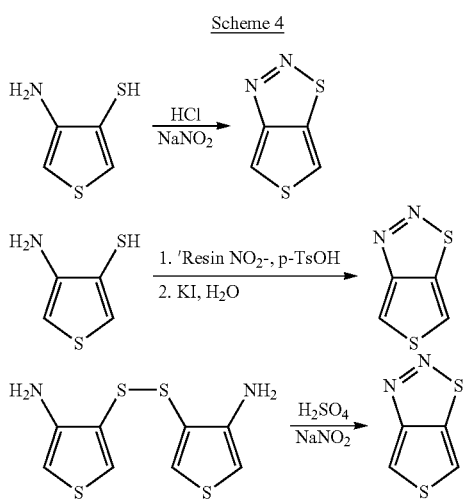

Scheme 5 provides possible synthetic routes to a brominated version of the moiety represented by formula (III), which can be used as a precursor for polymerization or coupling with other conjugated moieties, for example, via Suzuki or Stille coupling. Example of bromination procedures can be found in the following reference: De Almeida et al., Current Green Chemistry (2014), 1(2), 94-107.

Scheme 5

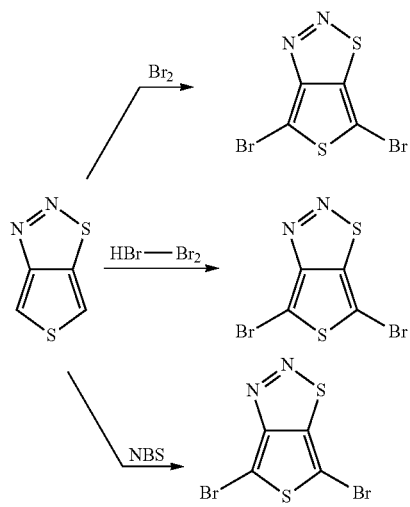

A moiety represented by formula (IV) can be prepared according to Scheme 6 below. The final product can be brominated and used to prepare various compounds according to the present teachings, for example, via Suzuki or Stille coupling.

Scheme 6

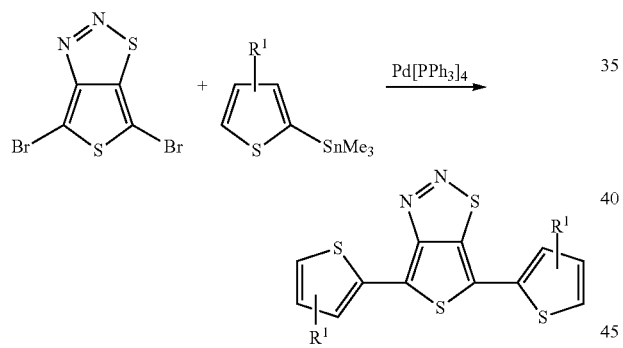

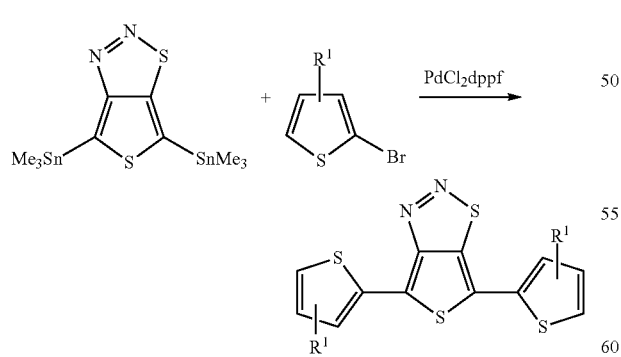

Schemes 7-10 provides possible synthetic routes to a brominated version of the moieties represented by formulae (III) and (IV) which, respectively, can be used as precursors for polymerization or coupling with other conjugated moieties, for example, via Suzuki or Stille coupling.

Scheme 7

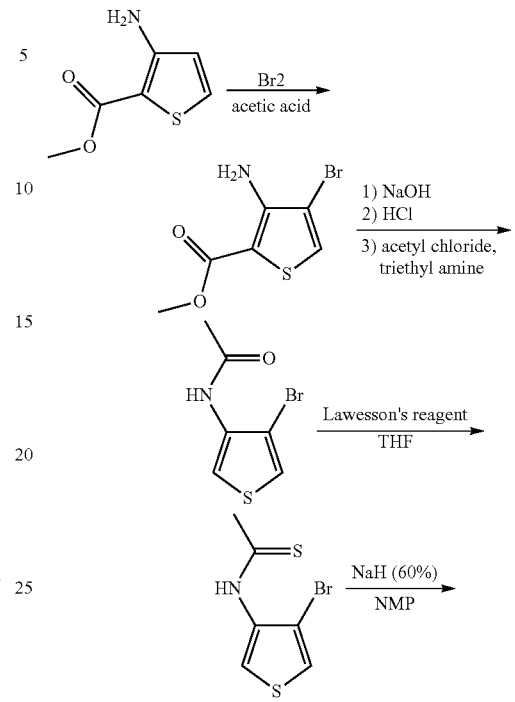

Scheme 8

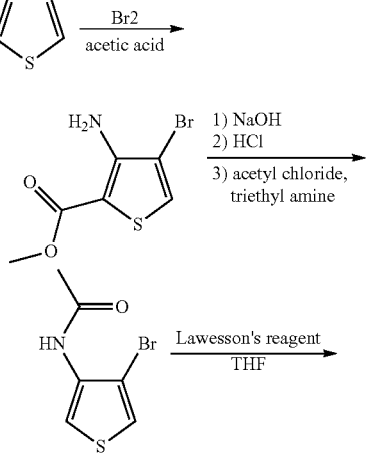

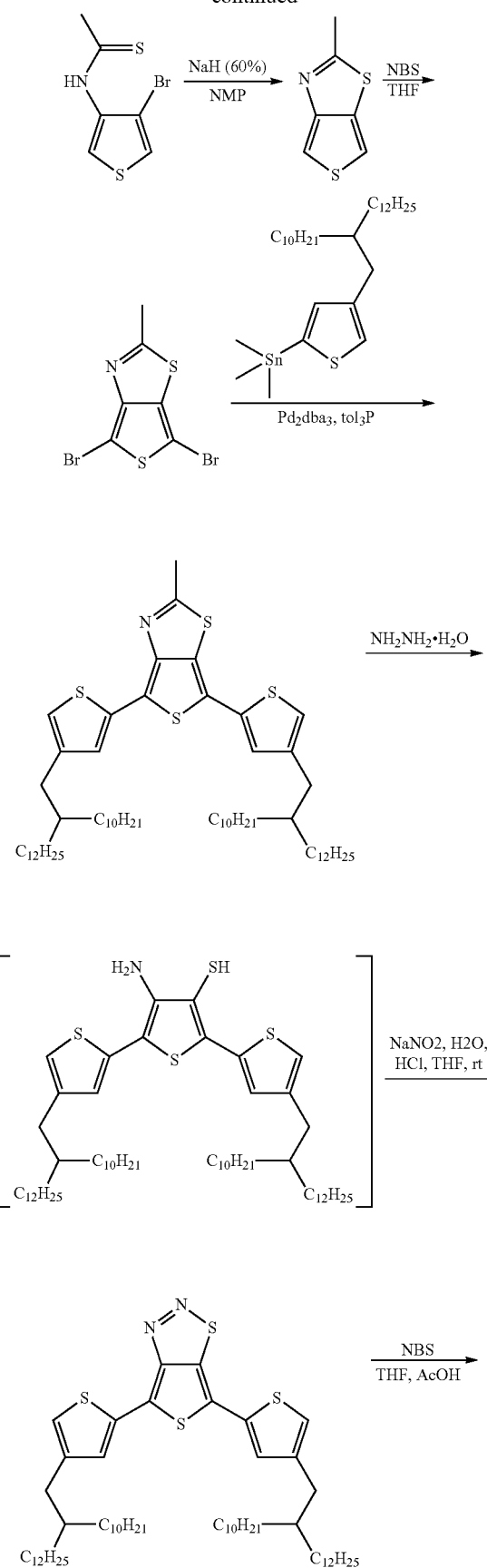

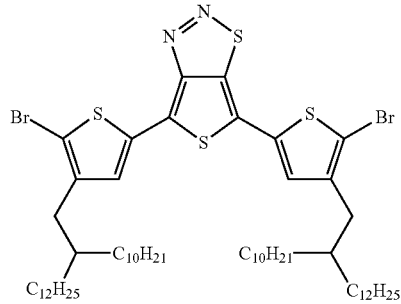

Schemes 7 and 8 are essentially identical. The synthesis of the intermediate thieno[3,4-d]thiazole could be achieved by following the procedures described in (1) Jo, J. W. et al., *Org. Electron.*, 13: 1322 (2012); and (2) Uy, R. et al., *Macromolecules*, 44: 9146 (2011). The ring opening reaction to form 3-amino-4-mercaptothiophene derivatives could be performed by using hydrazine in ethanol according to the procedures described in (1) Adelaere, B. et al., *Phosphorus, Sulfur, and Silicon,* 69: 173 (1992); and (2) Katner, A. S. et al., *Heterocyclic Chem.*, 27: 563 (1990).

Scheme 9

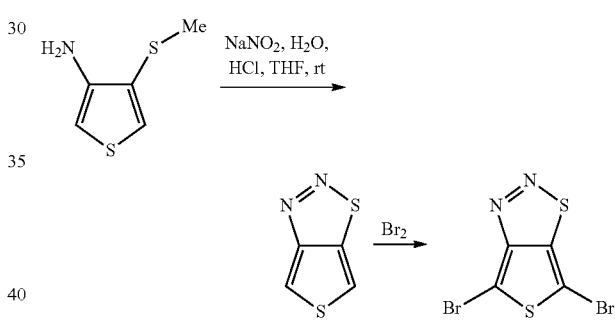

Scheme 9 provides yet an alternative synthetic route starting from 3-amino-4-(methylthio)thiophene, followed by diazotization, and then bromination.

Scheme 10

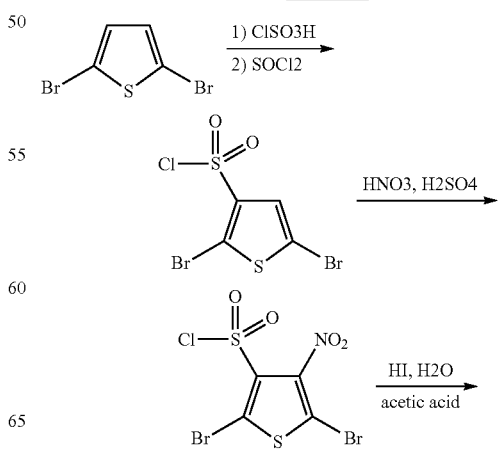

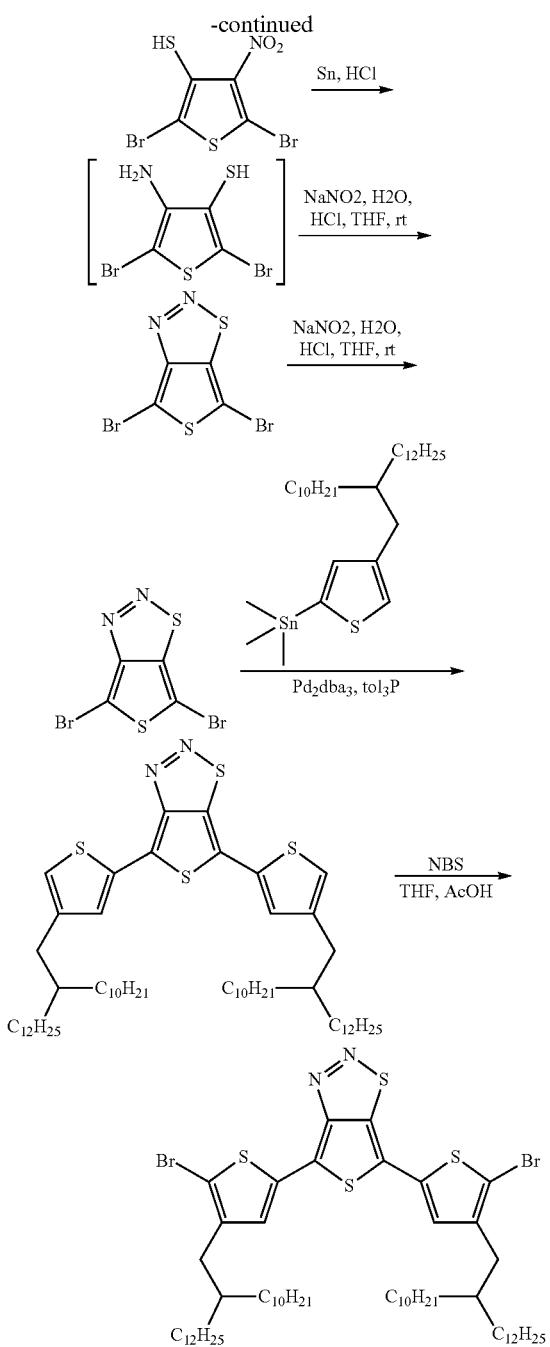

Referring to Scheme 10, the chlorosulfonation of 2,5-dibromothiophene can be realized by using a mixture of chlorosulfonic acid and thionyl chloride. Next, the nitration can be carried out in a mixture of $HNO_3$ and $H_2SO_4$. See Francotte, P. et al., *J. Med. Chem.*, 56: 7838 (2013). The formation of 3-amino-4-mercapto-2,5-dibromothiophene can be achieved by heating 3-amino-2,5-dibromothiophene-3-sulfonic acid chloride in acetic acid in the presence of 55% hydroiodic acid, followed by reduction of the nitro group by metal tin (or tin (II) chloride) in acid condition. See Zherdeva, S. Y. et al., *Zh. Origani. Khimi*, 16: 430-438 (1980).

Various compounds disclosed herein can be stable in ambient conditions ("ambient stable") and soluble in common solvents. As used herein, a compound can be considered electrically "ambient stable" or "stable at ambient conditions" when the carrier mobility or the reduction-potential of the compound is maintained at about its initial measurement when the compound is exposed to ambient conditions, for example, air, ambient temperature, and humidity, over a period of time. For example, a compound according to the present teachings can be described as ambient stable if its carrier mobility or redox potential does not vary more than 20% or more than 10% from its initial value after exposure to ambient conditions, including, air, humidity and temperature, over a 3 day, 5 day, or 10 day period. In addition, a compound can be considered ambient stable if the optical absorption of the corresponding film does not vary more than 20% (preferably, does not vary more than 10%) from its initial value after exposure to ambient conditions, including air, humidity and temperature, over a 3 day, 5 day, or 10 day period.

Organic thin film transistors (OTFTs) based on the present compounds can have long-term operability and continued high-performance in ambient conditions. For example, OTFTs based on certain embodiments of the present compounds can maintain satisfactory device performance in highly humid environment. Certain embodiments of the present compounds also can exhibit excellent thermal stability over a wide range of annealing temperatures. Photovoltaic devices can maintain satisfactory power conversion efficiencies over an extended period of time.

Compounds, particularly polymers, disclosed herein can be soluble in various common organic solvents. As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone. The present polymers can have room temperature solubilities in conventional organic solvents such as xylene, dichlorobenzene (DCB), and other chlorinated hydrocarbons (CHCs) as high as 60 g/L.

The compounds described herein can be dissolved, dispersed or suspended in a single solvent or mixture of solvents to provide a composition suitable for solution processing techniques. In preferred embodiments, the solvent can be selected from the group consisting of chlorobenzene, dichlorobenzene (o-dichlorobenzene, m-dichlorobenzene, p-orobenzene, or mixtures thereof), trichlorobenzene, benzene, toluene, chloroform, dichloromethane, dichloroethane, xylenes, α,α,α-trichlorotoluene, methyl naphthalene (e.g., 1-methylnaphthalene, 2-methylnaphthalene, or mixtures thereof), chloronaphthalene (e.g., 1-chloronaphthalene, 2-chloronaphthalene, or mixtures thereof), and mixtures thereof. The present compounds can be fabricated into various articles of manufacture using solution processing techniques in addition to other more expensive processes such as vapor deposition. Various solution-phase processing techniques have been used with organic electronics. Common solution-phase processing techniques include, for example, spin coating, slot coating, doctor blading, drop-casting, zone casting, dip coating, blade coating, or spraying. Another example of solution-phase processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Compounds of the present teachings can be used to prepare semiconductor materials (e.g., compositions and composites), which in turn can be used to fabricate various articles of manufacture, structures, and devices. In some embodiments, semiconductor materials incorporating one or more compounds of the present teachings can exhibit n-type semiconductor activity, ambipolar activity, light absorption, and light emission.

The present teachings, therefore, further provide methods of preparing a semiconductor material. The methods can include preparing a composition that includes one or more compounds disclosed herein dissolved or dispersed in a liquid medium such as a solvent or a mixture of solvents, depositing the composition on a substrate to provide a semiconductor material precursor, and processing (e.g., heating) the semiconductor precursor to provide a semiconductor material (e.g., a thin film semiconductor) that includes a compounds disclosed herein. In various embodiments, the liquid medium can be an organic solvent, an inorganic solvent such as water, or combinations thereof. In some embodiments, the composition can further include one or more additives independently selected from viscosity modulators, detergents, dispersants, binding agents, compatibilizing agents, curing agents, initiators, humectants, antifoaming agents, wetting agents, pH modifiers, biocides, and bacteriostats. For example, surfactants and/or polymers (e.g., polystyrene, polyethylene, poly-alpha-methylstyrene, polyisobutene, polypropylene, polymethylmethacrylate, and the like) can be included as a dispersant, a binding agent, a compatibilizing agent, and/or an antifoaming agent. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, drop-casting, zone casting, dip coating, blade coating, or spraying.

Various articles of manufacture including electronic devices, optical devices, and optoelectronic devices, such as thin film semiconductors, field effect transistors (e.g., thin film transistors), photovoltaics, photodetectors, organic light emitting devices such as organic light emitting diodes (OLEDs) and organic light emitting transistors (OLETs), complementary metal oxide semiconductors (CMOSs), complementary inverters, diodes, capacitors, sensors, D flip-flops, rectifiers, and ring oscillators, that make use of the compounds disclosed herein are within the scope of the present teachings as are methods of making the same. The present compounds can offer processing and operation advantages in the fabrication and/or the use of these devices. For example, articles of manufacture such as the various devices described herein can include a composite having a semiconductor material of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., described in Yoon, M-H. et al., *PNAS*, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)). One or more of the composites described herein can be embodied within various organic electronic, optical, and optoelectronic devices such as organic thin film transistors (OTFTs), specifically, organic field effect transistors (OFETs), as well as sensors, capacitors, unipolar circuits, complementary circuits (e.g., inverter circuits), and the like.

Other articles of manufacture in which compounds of the present teachings are useful are photovoltaics or solar cells. Compounds of the present teachings can exhibit broad optical absorption and/or a tuned redox properties and bulk carrier mobilities, making them desirable for such applications. Accordingly, the compounds described herein can be used as an acceptor (n-type) semiconductor or a donor (p-type) semiconductor depending on the nature of the moieties other than the moiety represented by formula (I) in a photovoltaic design, which includes an adjacent p-type or n-type semiconductor material, respectively, that forms a p-n junction. The compounds can be in the form of a thin film semiconductor, which can be deposited on a substrate to form a composite. Exploitation of compounds of the present teachings in such devices is within the knowledge of a skilled artisan.

Accordingly, another aspect of the present teachings relates to methods of fabricating an organic field effect transistor that incorporates a semiconductor material of the present teachings. The semiconductor materials of the present teachings can be used to fabricate various types of organic field effect transistors including top-gate top-contact capacitor structures, top-gate bottom-contact capacitor structures, bottom-gate top-contact capacitor structures, and bottom-gate bottom-contact capacitor structures. FIG. 1 illustrates the four common types of OFET structures: (a) bottom-gate top-contact structure, (b) bottom-gate bottom-contact structure, (c) top-gate bottom-contact structure, and (d) top-gate top-contact structure. As shown in FIG. 1, an OFET can include a dielectric layer (e.g., shown as 8, 8', 8", and 8''' in FIGS. 1*a*, 1*b*, 1*c*, and 1*d*, respectively), a semiconductor/channel layer (e.g., shown as 6, 6', 6", and 6''' in FIGS. 1*a*, 1*b*, 1*c*, and 1*d*, respectively), a gate contact (e.g., shown as 10, 10', 10", and 10''' in FIGS. 1*a*, 1 *b*, 1*c*, and 1*d*, respectively), a substrate (e.g., shown as 12, 12', 12", and 12''' in FIGS. 1a, 1b, 1 c, and 1d, respectively), and source and drain contacts (e.g., shown as 2, 2', 2'', 2''', 4, 4', 4'', and 4' in FIGS. 1a, 1 b, 1c, and 1d, respectively).

In certain embodiments, OTFT devices can be fabricated with the present compounds on doped silicon substrates, using SiO2 as the dielectric, in top-contact geometries. In particular embodiments, the active semiconductor layer which incorporates at least a compound of the present teachings can be deposited at room temperature or at an elevated temperature. In other embodiments, the active semiconductor layer which incorporates at least one compound of the present teachings can be applied by spin-coating or printing as described herein. For top-contact devices, metallic contacts can be patterned on top of the films using shadow masks.

In certain embodiments, OTFT devices can be fabricated with the present compounds on plastic foils, using polymers as the dielectric, in top-gate bottom-contact geometries. In particular embodiments, the active semiconducting layer which incorporates at least a compound of the present teachings can be deposited at room temperature or at an elevated temperature. In other embodiments, the active semiconducting layer which incorporates at least a compound of the present teachings can be applied by spin-coating or printing as described herein. Gate and source/drain contacts can be made of Au, other metals, or conducting polymers and deposited by vapor-deposition and/or printing.

Figure 2:
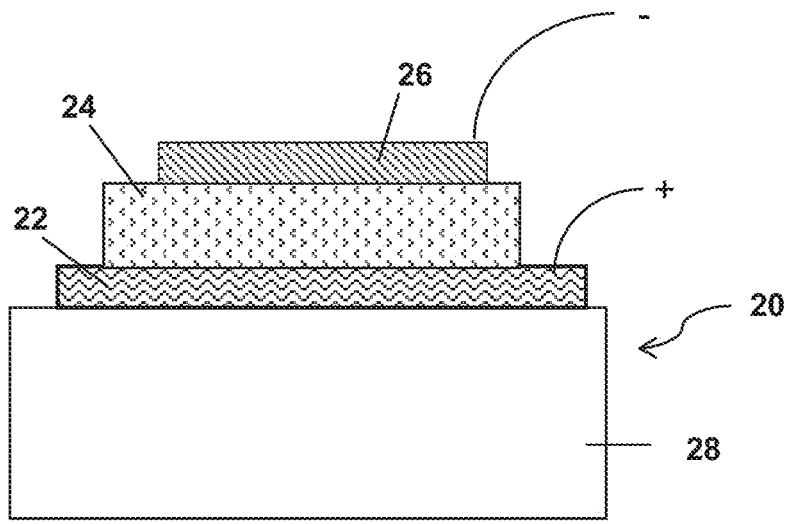
FIG. 2 illustrates a representative structure of a bulk-heterojunction organic photovoltaic device (also known as a solar cell), which can incorporate one or more compounds of the present teachings as the donor and/or acceptor materials.
Figure 3:
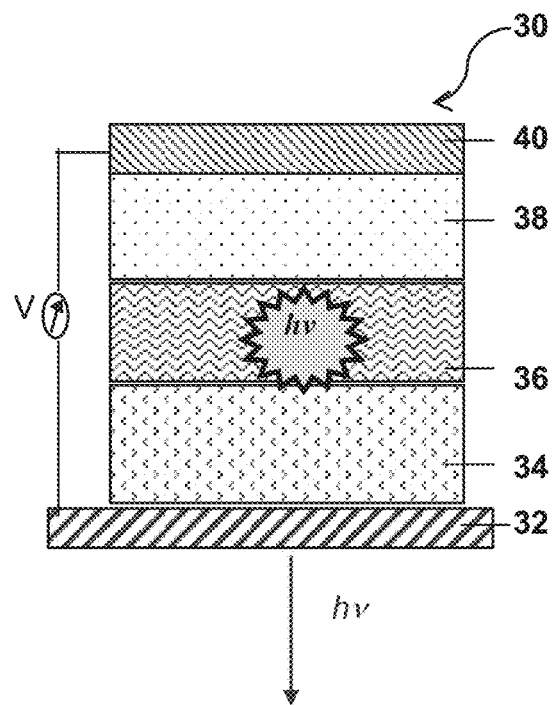
FIG. 3 illustrates a representative structure of an organic light-emitting device which can incorporate one or more compounds of the present teachings as electron-transporting and/or emissive and/or hole-transporting materials.

Similarly, another aspect of the present teachings relates to methods of fabricating an organic light-emitting transistor, an organic light-emitting diode (OLED), or an organic photovoltaic device that incorporates one or more semiconductor materials of the present teachings. FIG. 2 illustrates a representative structure of a bulk-heterojunction organic photovoltaic device (also known as solar cell) which can incorporate one or more compounds of the present teachings as the donor and/or acceptor materials. As shown, a representative solar cell generally includes a substrate 20 (e.g., glass), an anode 22 (e.g., ITO), a cathode 26 (e.g., aluminium or calcium), and an active layer 24 between the anode and the cathode which can incorporate one or more compounds of the present teachings as the electron donor (p-channel) and/or electron acceptor (n-channel) materials. FIG. 3 illustrates a representative structure of an OLED which can incorporate one or more compounds of the present teachings as electron-transporting and/or emissive and/or hole-transporting materials. As shown, an OLED generally includes a substrate 30 (not shown), a transparent anode 32 (e.g., ITO), a cathode 40 (e.g., metal), and one or more organic layers which can incorporate one or more compounds of the present teachings as hole-transporting (n-channel) (layer 34 as shown) and/or emissive (layer 36 as shown) and/or electron-transporting (p-channel) materials (layer 38 as shown).

Figure 4:
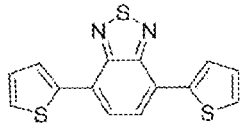
FIG. 4 and FIG. 5 provide tables summarizing the chemical structures, frontier molecular orbital energy values, and molecular orbital topology for various thiadiazole units.
Figure 4:
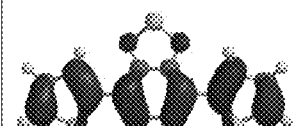
Figure 4:
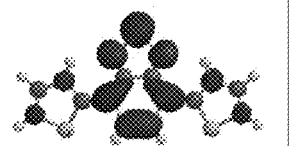
Figure 4:
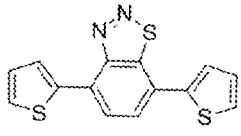
Figure 4:
Figure 4:
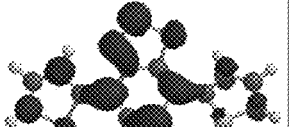
Figure 4:
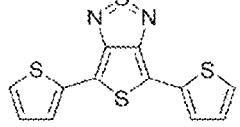
Figure 4:
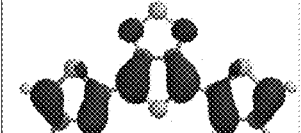
Figure 4:
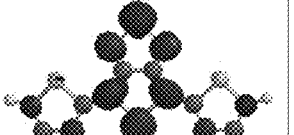
Figure 4:
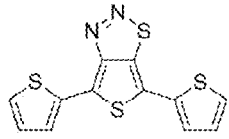
Figure 4:
Figure 4:
Figure 4:
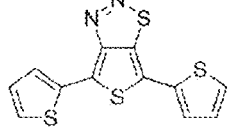
Figure 4:
Figure 4:
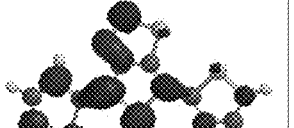
Figure 4:
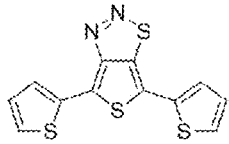
Figure 4:
Figure 4:
Figure 4:
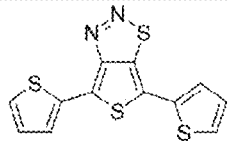
Figure 4:
Figure 4:
Figure 5:
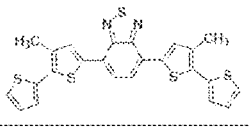
Figure 5:
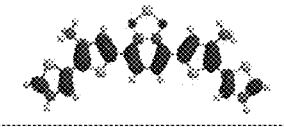
Figure 5:
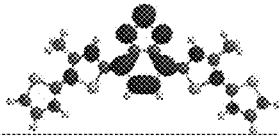
Figure 5:
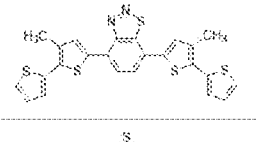
Figure 5:
Figure 5:
Figure 5:
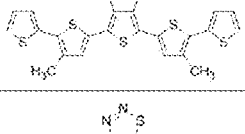
Figure 5:
Figure 5:
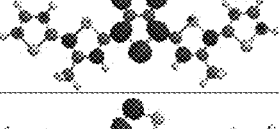
Figure 5:
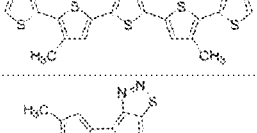
Figure 5:
Figure 5:
Figure 5:
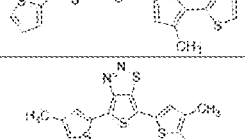
Figure 5:
Figure 5:
Figure 5:
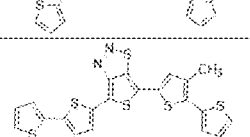
Figure 5:
Figure 5:
Figure 5:
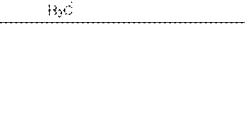
Figure 5:
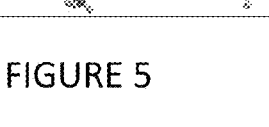
Figure 5:
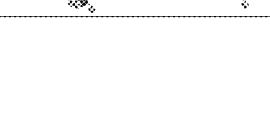

Molecular orbital (MO) calculations (B3LYP/6-31G*) (Spartan'08 Wavefunction, Inc. Irvine, Calif.) were carried out to compare vis-à-vis the geometrical parameters, electronic structure, and HOMO/LUMO energy levels of conventional dithienyl, bis(dithienyl), and unsubstituted benzo[1,2,5]thiadiazole and benzo[1,2,3]thiadiazole versus those of the thienothiazole-based systems disclosed here. The tables of FIGS. 4 and 5 summarize the chemical structures, frontier molecular orbital energy values, and molecular orbital topology for the indicated thiadiazole units. These data demonstrate that the new cores according to the present teachings are all very planar, which is essential for good charge transport for the corresponding molecular and polymeric semiconductors. Interestingly, the results show that all of the new thieno building blocks with the same substitution pattern exhibit comparable or higher HOMO energies compared to those of the parent systems. Because the parent derivatives are known to be good p-channel semiconductors in field-effect transistors and good donor semiconductors in organic solar cells, it is expected that these new compounds will perform well.

All publications, including but not limited to patents and patent applications, cited in this specification are herein incorporated by reference as if each individual publication were specifically and individually indicated to be incorporated by reference herein as though fully set forth.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. A compound comprising one or more moieties represented by formula (I):

wherein X is a chalcogen; and one or more linear conjugated moieties and/or one or more cyclic conjugated moieties other than the moieties represented by formula (I), and wherein the compound is a polymer having a first repeating unit $M_1$ selected from the group consisting of:

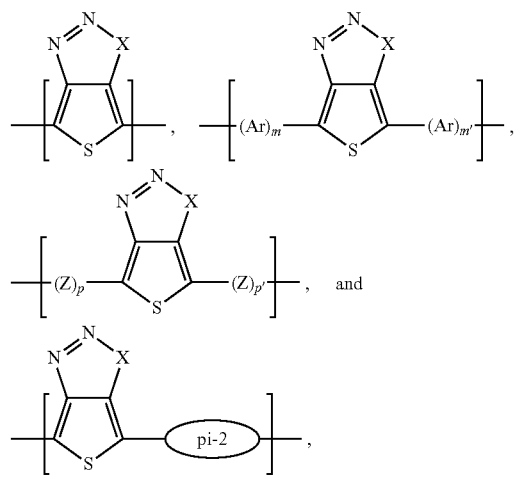

wherein:
pi-2 is an optionally substituted conjugated polycyclic moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0;

p and p' independently are 0 and 1, provided that at least one of p and p' is 1; and the polymer has a degree of polymerization (n) ranging from 3 to 1,000.

2. The compound of claim 1, wherein the compound comprises one or more moieties represented by formula (II):

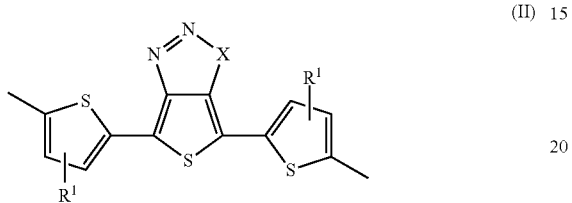

(II)

wherein $R^1$, at each occurrence, independently is selected from the group consisting of H, halogen, —CN, $NO_2$, $R^2$, -L-$R^3$, OH, $OR^2$, $OR^3$, $NH_2$, $NHR^2$, $N(R^2)_2$, $NHR^3$, $NR^2R^3$, $N(R^3)_2$, SH, $SR^2$, $SR^3$, $S(O)_2OH$, —$S(O)_2OR^2$, —$S(O)_2OR^3$, C(O)H, $C(O)R^2$, $C(O)R^3$, C(O)OH, $C(O)OR^2$, $C(O)OR^3$, $C(O)NH_2$, $C(O)NHR^2$, $C(O)N(R^2)_2$, $C(O)NHR^3$, $C(O)NR^2R^3$, $C(O)N(R^3)_2$, $SiH(R^2)_2$, $SiH_2(R^2)$, and $Si(R^2)_3$, wherein L is selected from the group consisting of a divalent $C_{1-40}$ alkyl group, a divalent $C_{2-40}$ alkenyl group, a divalent $C_{1-40}$ haloalkyl group, and a covalent bond; $R^2$ is selected from the group consisting of a $C_{1-40}$ alkyl group, a $C_{2-40}$ alkenyl group, a $C_{2-40}$ alkynyl group, and a $C_{1-40}$ haloalkyl group; and $R^3$ is selected from the group consisting of a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents selected from the group consisting of a halogen, —CN, $NO_2$, $R^2$, $OR^2$, and $SR^2$.

3. The compound of claim 1, wherein X is selected from the group consisting of O, S, and Se.

4. The compound of claim 3, wherein the compound comprises one or more moieties represented by formula (III) or (IV):

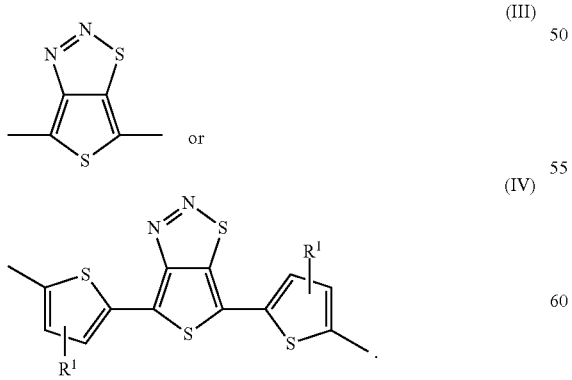

5. The compound of claim 1, wherein the compound is a polymer having a first repeating unit $M_1$ selected from the group consisting of:

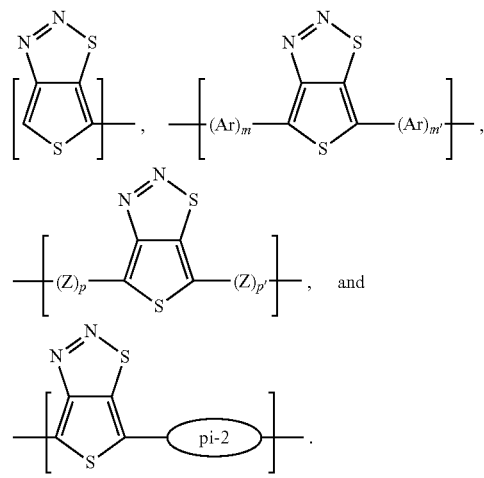

6. The compound of claim 2, wherein the compound is a polymer having a first repeating unit $M_1$ selected from the group consisting of:

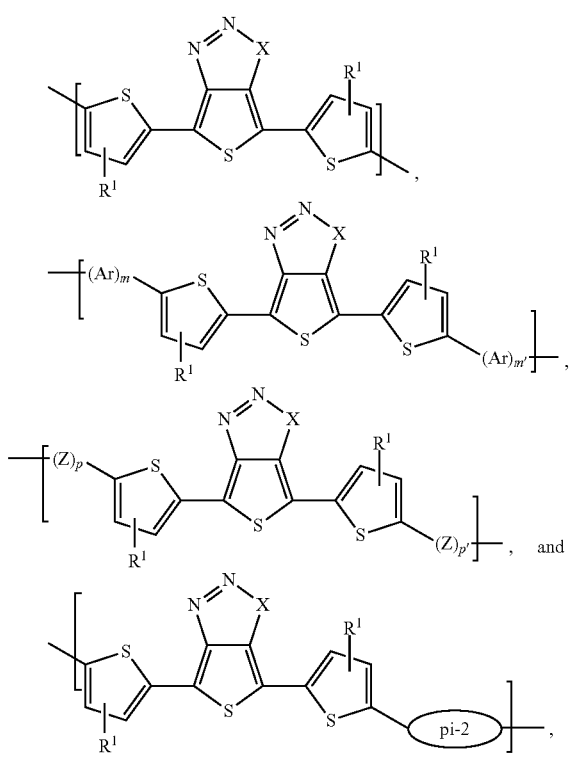

wherein:

pi-2 is an optionally substituted conjugated polycyclic moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0;

p and p' independently are 0 and 1, provided that at least one of p and p' is 1; and the polymer has a degree of polymerization (n) ranging from 3 to 1,000.

7. The compound of claim 6, wherein the compound is a polymer having a first repeating unit $M_1$ selected from the group consisting of:

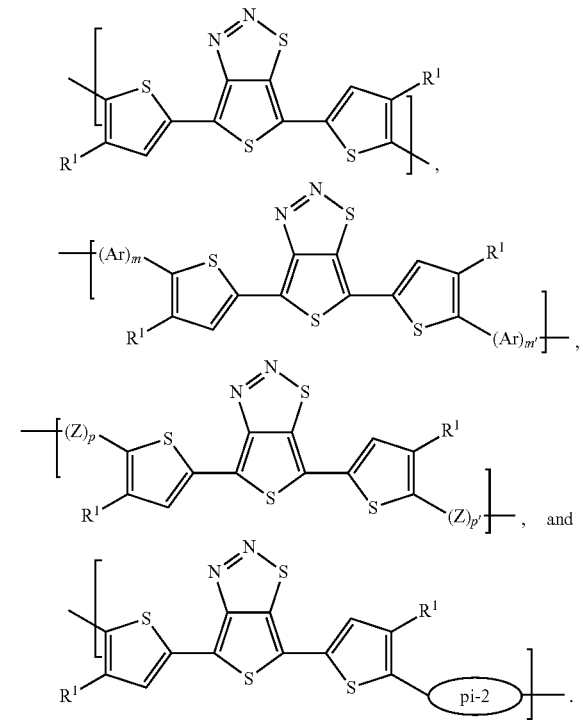

8. The compound of claim 6, wherein $R^1$, at each occurrence, independently is selected from the group consisting of H, F, Cl, —CN, —NO$_2$, $R^2$, $OR^2$, and $SR^2$, wherein $R^2$ is selected from the group consisting of a linear or branched $C_{1-40}$ alkyl group, a linear or branched $C_{2-40}$ alkenyl group, and a linear or branched $C_{1-40}$ haloalkyl group.

9. The compound of claim 1 further comprising one or more additional repeating units $M_2$ that are different from the first repeating unit $M_1$, said additional repeating units $M_2$ being selected from the group consisting of:

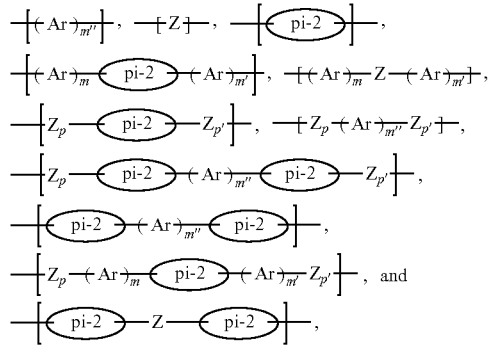

wherein:
pi-2 is an optionally substituted conjugated polycyclic moiety;
Ar, at each occurrence, is independently an optionally substituted 5- or 6-membered aryl or heteroaryl group;

Z is a conjugated noncyclic linker;
m and m' independently are 0, 1, 2, 3, 4, 5 or 6, provided that at least one of m and m' is not 0;
m" is 1, 2, 3, 4, 5 or 6; and
p and p' independently are 0 and 1, provided that at least one of p and p' is 1.

10. The compound of claim 9 represented by formula (V) or (VI):

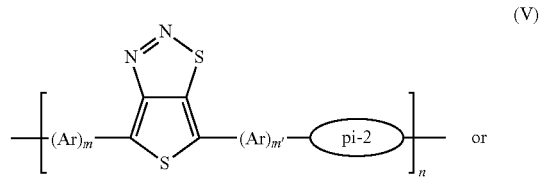

(V)

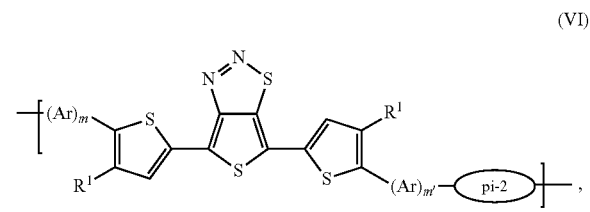

(VI)

wherein n is an integer ranging from 3 to 1,000.

11. The compound of claim 10, wherein pi-2 in the first repeating unit $M_1$ and any additional repeating unit $M_2$ is an optionally substituted $C_{8-26}$ aryl group or 8-26 membered heteroaryl group selected from the group consisting of:

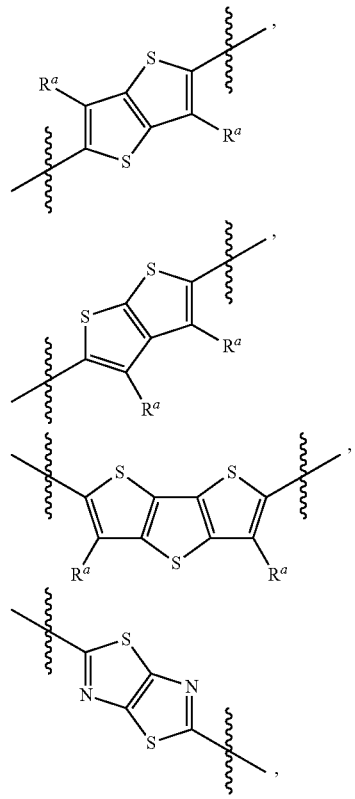

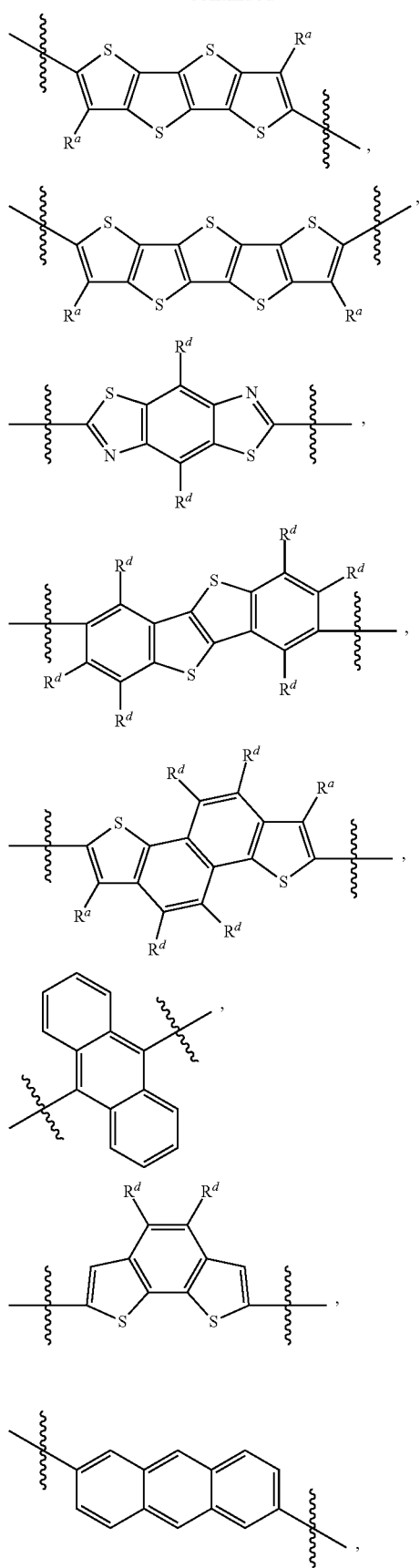
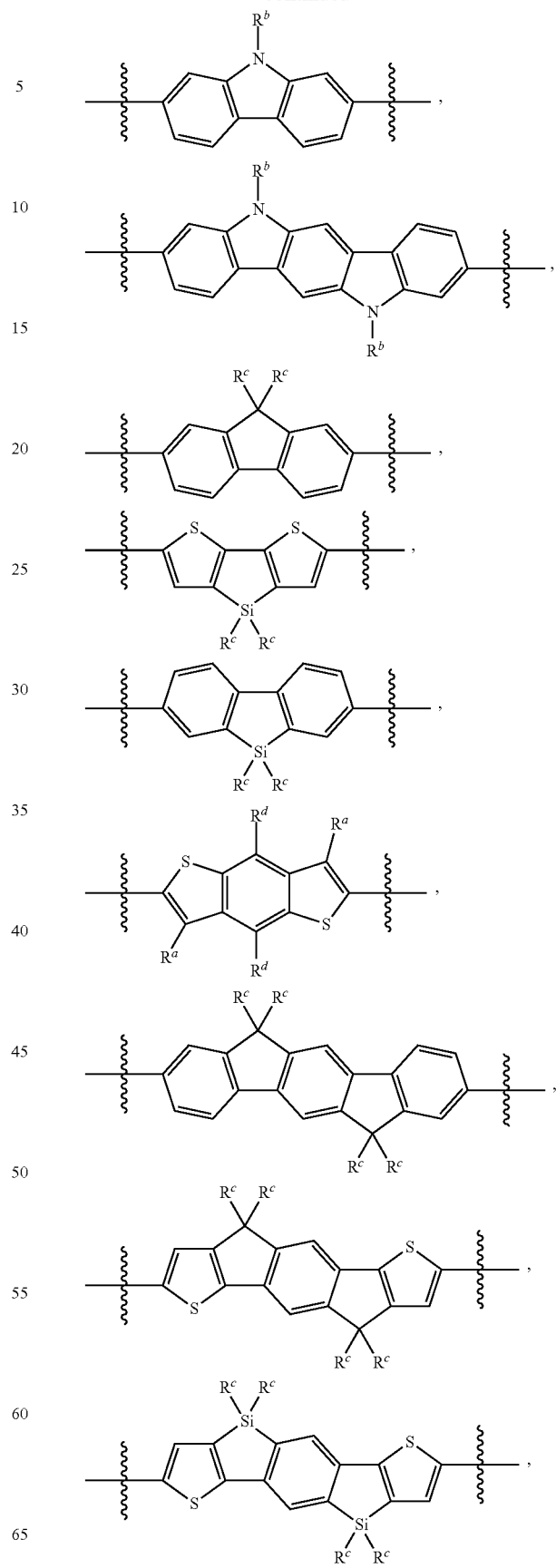

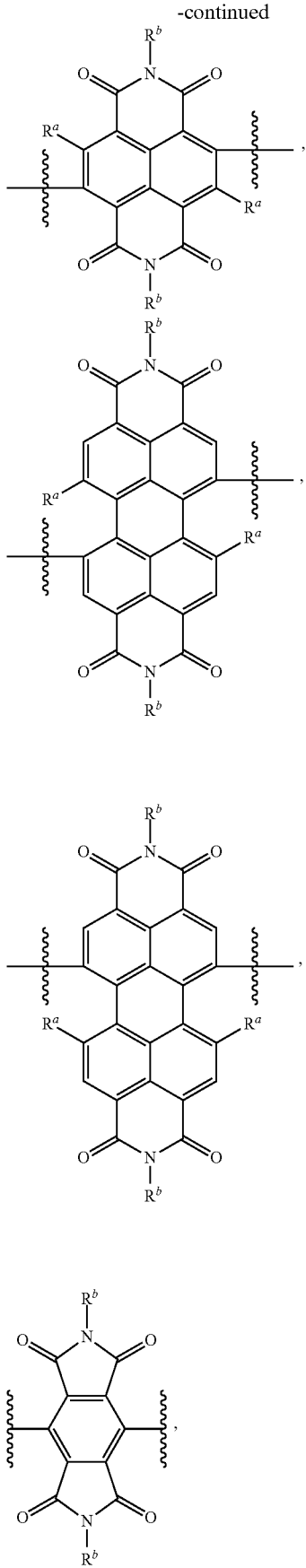
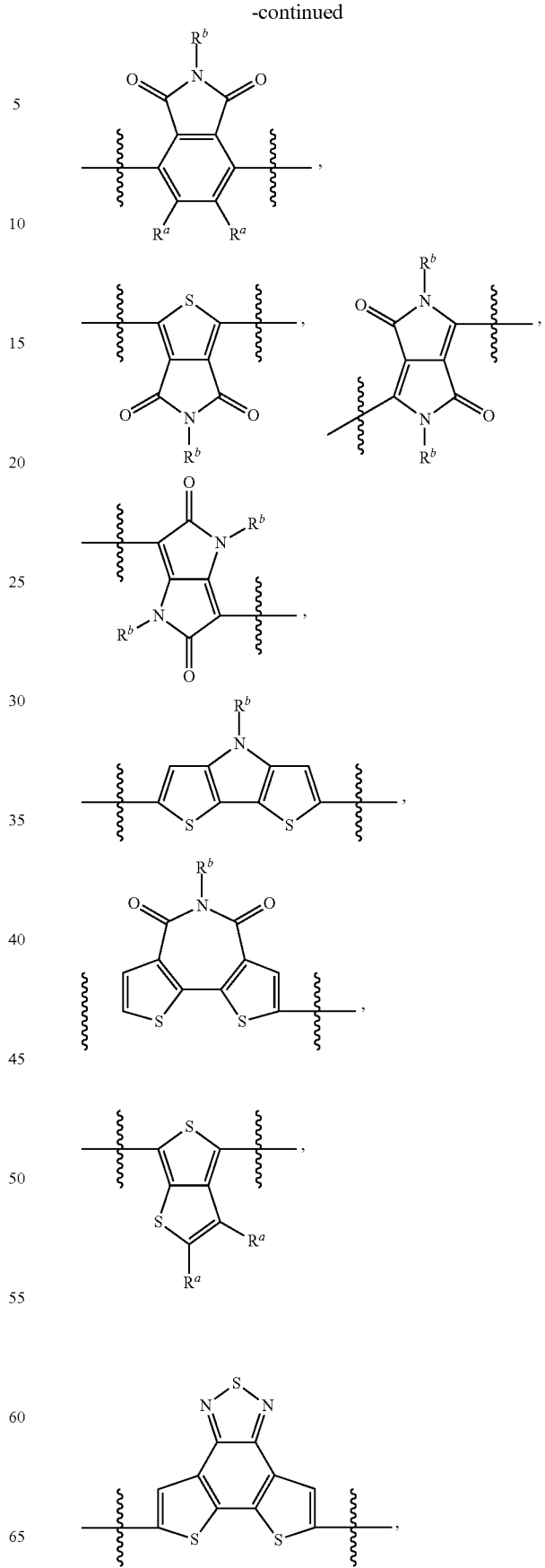

-continued
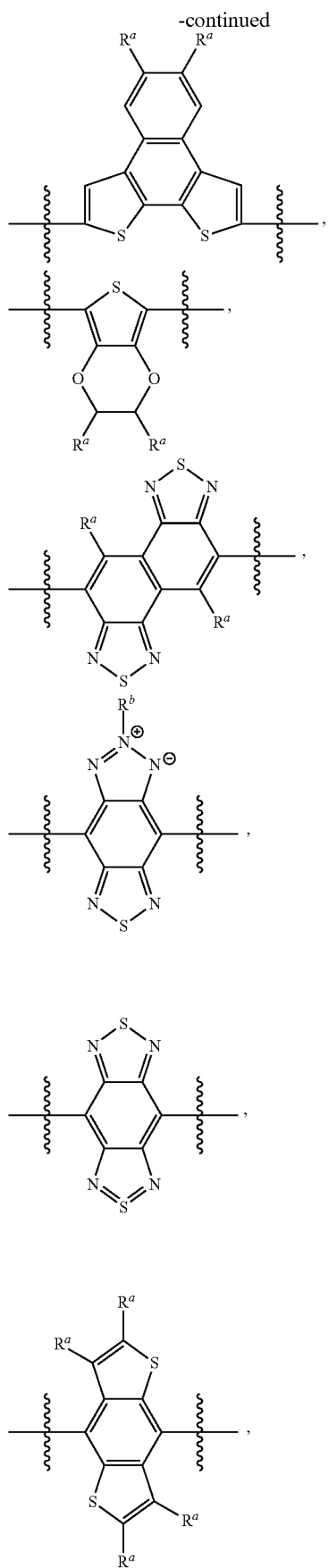
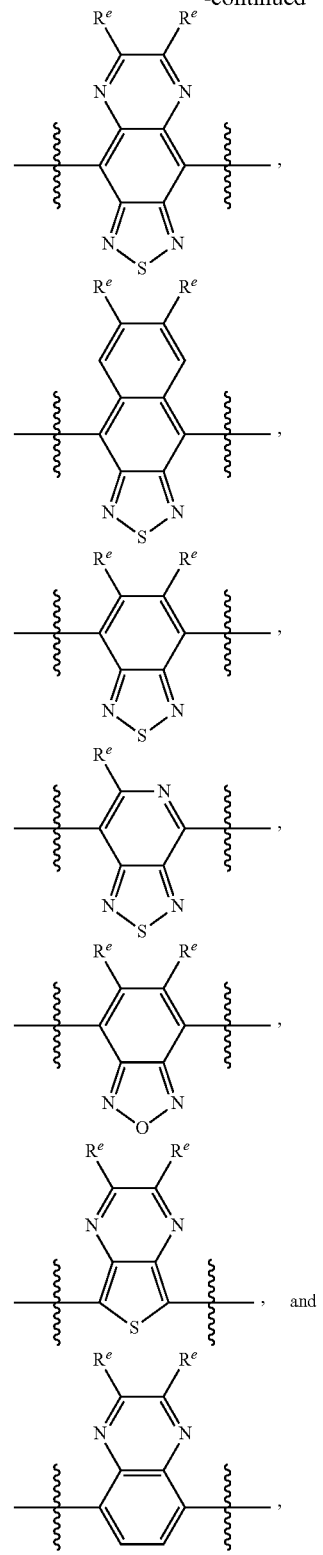
, and
wherein:
R$^a$ is selected from the group consisting of H, F, Cl, —CN, R, —OR, —SR, —C(O)R, —OC(O)R, and —C(O)OR;
R$^b$ is selected from the group consisting of H, R, and -L'-R$^f$;

$R^o$ is H or R;

$R^d$ is selected from the group consisting of H, F, Cl, —CN, R, —OR, —SR, —C(O)R, —OC(O)R, —C(O)OR, and -L'-$R^f$;

$R^e$ is selected from the group consisting of H, F, Cl, —CN, R, —OR, —SR, —C(O)R, —OC(O)R, —C(O)OR, and $R^f$;

$R^f$ is a $C_{6-20}$ aryl group or a 5-20-membered heteroaryl group, each optionally substituted with 1-8 groups independently selected from the group consisting of F, Cl, —CN, R, —OR, and —SR;

L' is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group.

12. The compound of claim 1, wherein Ar in $(Ar)_m$, $(Ar)_{m'}$, and $(Ar)_{m''}$ in the first repeating unit $M_1$ and any additional repeating unit $M_2$ is represented by:

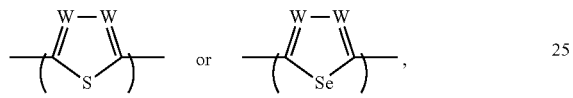

wherein each W independently is selected from the group consisting of N, CH, and $CR^4$, wherein $R^4$ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

13. The compound of claim 12, wherein $(Ar)_m$, $(Ar)_{m'}$, and $(Ar)_{m''}$ if present in either the first repeating unit $M_1$ or any additional repeating unit $M_2$ independently are selected from the group consisting of:

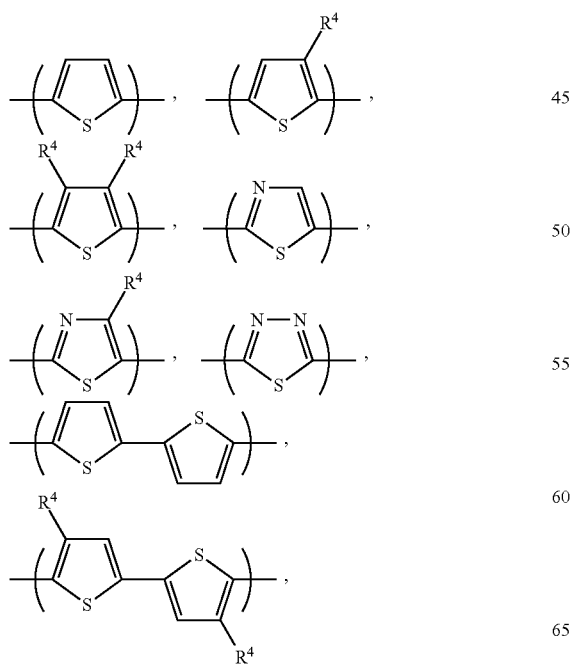

-continued

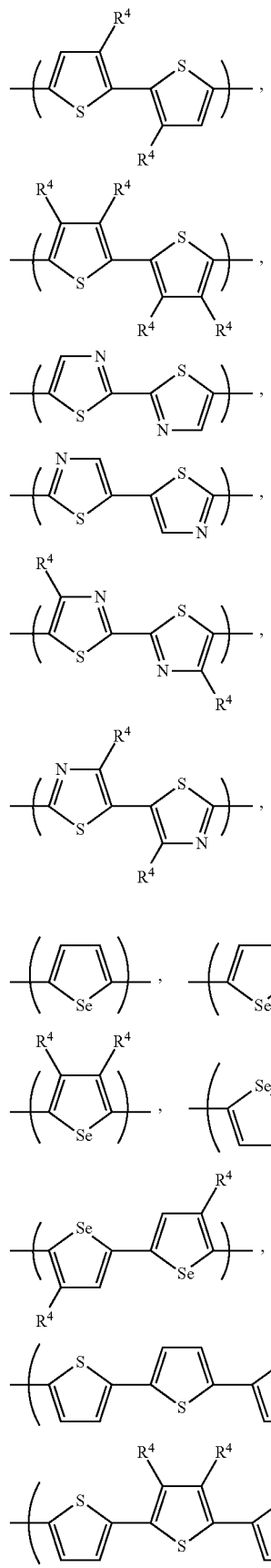

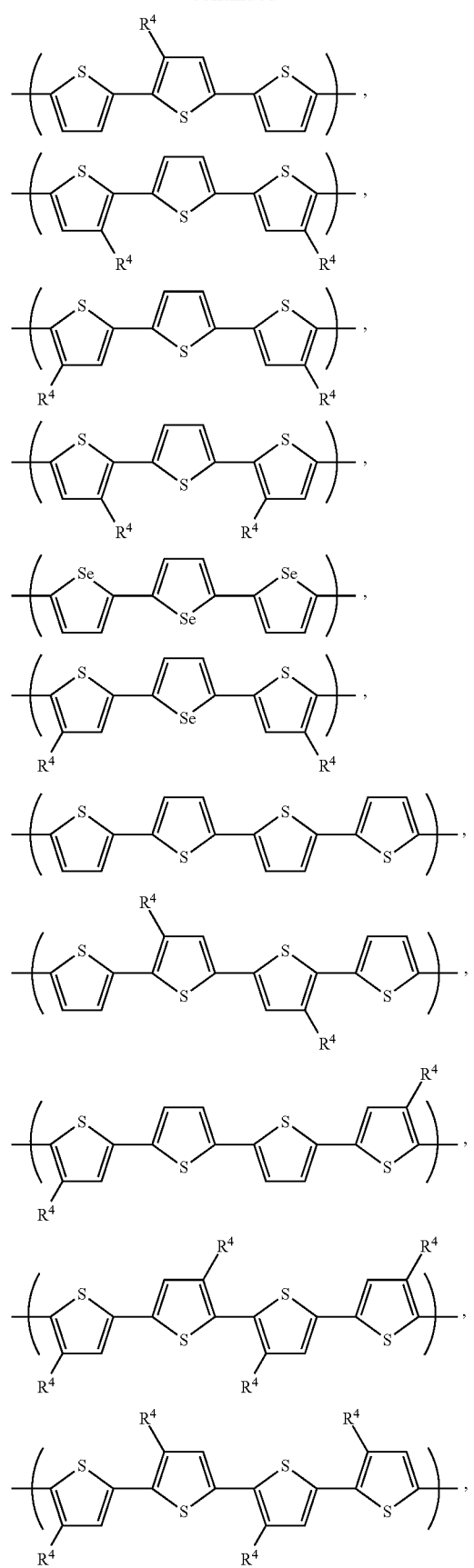
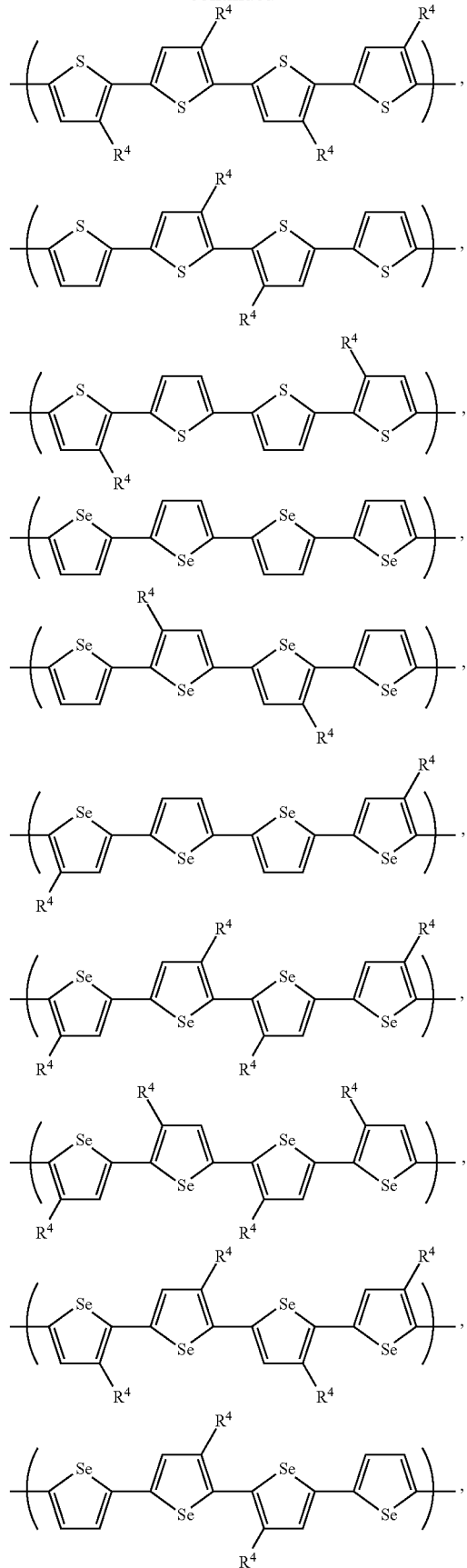

-continued

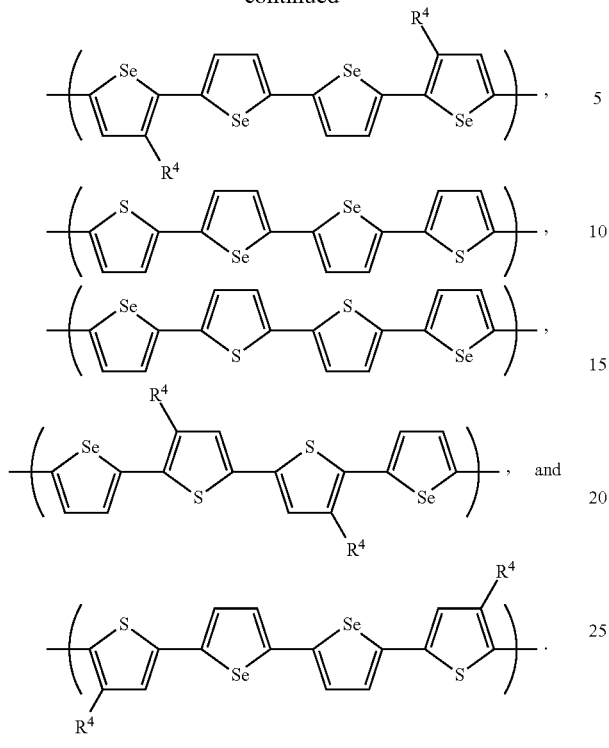

14. The compound of claim 1, wherein each Z if present in either the first repeating unit $M_1$ or any additional repeating unit $M_2$ is independently selected from the group consisting of:

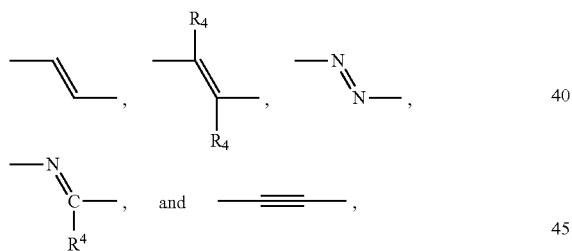

wherein $R^4$ is selected from the group consisting of F, Cl, —CN, $R^2$, $OR^2$, $SR^2$, $C(O)R^2$, $OC(O)R^2$, and $C(O)OR^2$, and wherein $R^2$ is selected from the group consisting of a $C_{1-40}$ alkyl group, a $C_{2-40}$ alkenyl group, a $C_{2-40}$ alkynyl group, and a $C_{1-40}$ haloalkyl group.

15. A compound comprising one or more moieties represented by formula (I):

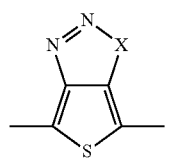

(I)

wherein X is a chalcogen; and one or more linear conjugated moieties and/or one or more cyclic conjugated moieties other than the moieties represented by formula (I), wherein the compound is a small molecule represented by formula (VII) or (VIII):

(VII)

(VIII)

wherein:
$R^1$, at each occurrence, independently is selected from the group consisting of H, halogen, —CN, $NO_2$, $R^2$, -L-$R^3$, OH, $OR^2$, $OR^3$, $NH_2$, $NHR^2$, $N(R^2)_2$, $NHR^3$, $NR^2R^3$, $N(R^3)_2$, SH, $SR^2$, $SR^3$, $S(O)_2OH$, —$S(O)_2OR^2$, —$S(O)_2OR^3$, C(O)H, $C(O)R^2$, $C(O)R^3$, C(O)OH, $C(O)OR^2$, $C(O)OR^3$, $C(O)NH_2$, $C(O)NHR^2$, $C(O)N(R^2)_2$, $C(O)NHR^3$, $C(O)NR^2R^3$, $C(O)N(R^3)_2$, $SiH_3$, $SiH(R^2)_2$, $SiH_2(R^2)$, and $Si(R^2)_3$, wherein L is selected from the group consisting of a divalent $C_{1-40}$ alkyl group, a divalent $C_{2-40}$ alkenyl group, a divalent $C_{1-40}$ haloalkyl group, and a covalent bond; $R^2$ is selected from the group consisting of a $C_{1-40}$ alkyl group, a $C_{2-40}$ alkenyl group, a $C_{2-40}$ alkynyl group, and a $C_{1-40}$ haloalkyl group; and $R^3$ is selected from the group consisting of a $C_{3-10}$ cycloalkyl group, a $C_{6-14}$ aryl group, a $C_{6-14}$ haloaryl group, a 3-12 membered cycloheteroalkyl group, and a 5-14 membered heteroaryl group, each of which optionally is substituted with 1-5 substituents selected from the group consisting of a halogen, —CN, $NO_2$, $R^2$, $OR^2$, and $SR^2$;

$R^5$ and $R^6$ independently are selected from the group consisting of H, $R^2$, $OR^2$, $SR^2$, $C(O)R^2$, $OC(O)R^2$, and $C(O)OR^2$;

$Q^1$ and $Q^2$ independently are selected from the group consisting of:

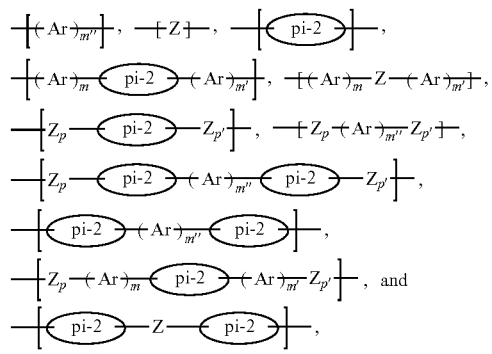

wherein:
pi-2 is an optionally substituted conjugated polycyclic moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0;

m" is 1, 2, 3, 4, 5 or 6; and p and p' independently are 0 and 1, provided that at least one of p and p' is 1.

16. A compound comprising one or more moieties represented by formula (I):

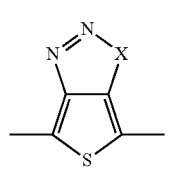

(I)

wherein X is a chalcogen; and one or more linear conjugated moieties and/or one or more cyclic conjugated moieties other than the moieties represented by formula (I), wherein the compound is a small molecule represented by formula (IX) or (X):

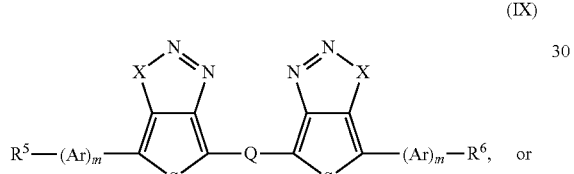

(IX)

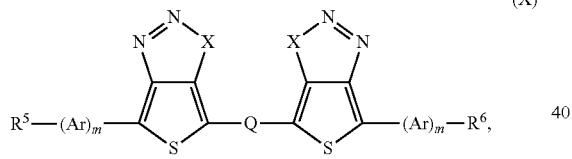

(X)

wherein:

Ar, at each occurrence, is independently an optionally substituted 5- or 6-membered aryl or heteroaryl group;

m and m' independently are 0, 1, 2, 3, 4, 5 or 6, provided that at least one of m and m' is not 0;

$R^5$ and $R^6$ independently are selected from the group consisting of H, $R^2$, $OR^2$, $SR^2$, $C(O)R^2$, $OC(O)R^2$, and $C(O)OR^2$;

Q is absent or selected from the group consisting of:

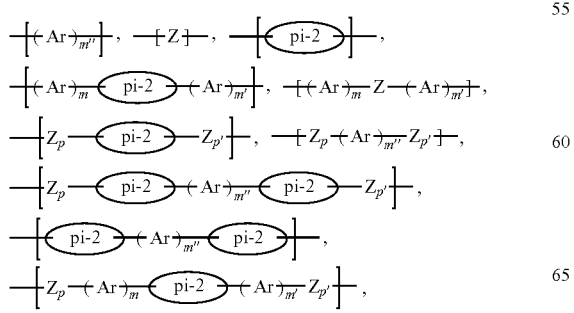

and a covalent bond, wherein:

pi-2 is an optionally substituted conjugated polycyclic moiety;

Ar, at each occurrence, is independently an optionally substituted 5- or 6-membered aryl or heteroaryl group;

Z is a conjugated noncyclic linker;

m and m' independently are 0, 1, 2, 3, 4, 5 or 6, provided that at least one of m and m' is not 0;

m" is 1, 2, 3, 4, 5 or 6; and p and p' independently are 0 and 1, provided that at least one of p and p' is 1.

17. The compound of claim 16, wherein the compound is a small molecule represented by formula (XI), (XII), (XIII), (XIV), (XV), or (XVI):

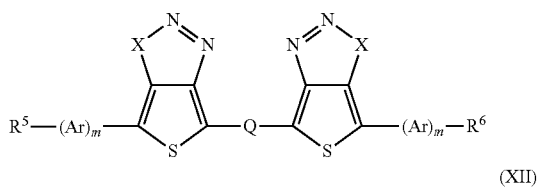

(XI)

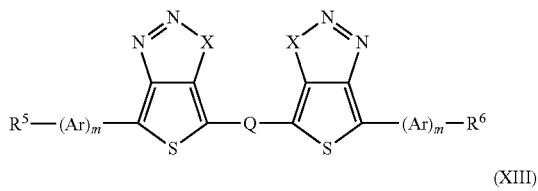

(XII)

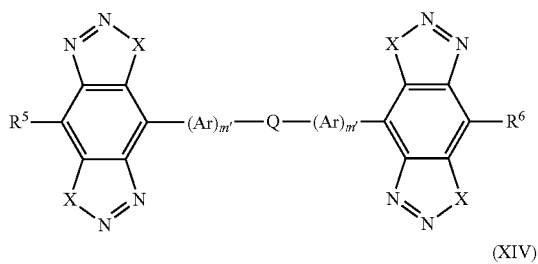

(XIII)

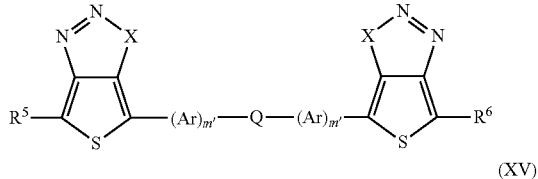

(XIV)

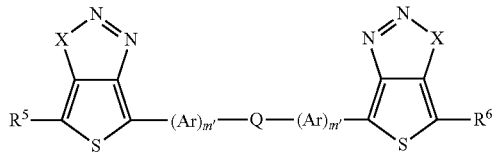

(XV)

-continued

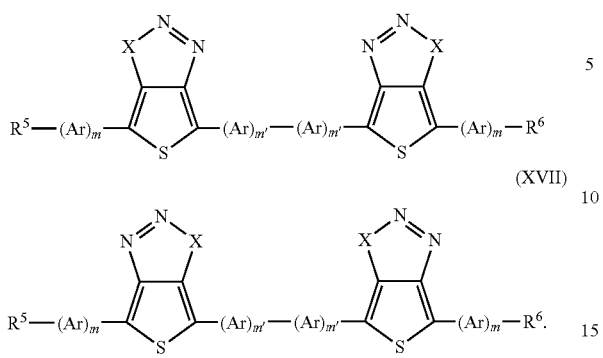

18. The compound of 16, wherein X is S, and wherein one of m and m' is 0 and the other of m and m' is 1, 2, 3, 4, 5 or 6.

19. An electronic device, an optical device, or an opto-electronic device comprising a thin film semiconductor component, the thin film semiconductor component comprising one or more compounds of claim 1.

20. The compound of claim 15, wherein X is selected from the group consisting of O, S, and Se.

* * * * *